United States Patent [19]
Matsumoto et al.

[11] Patent Number: 5,481,009
[45] Date of Patent: Jan. 2, 1996

[54] METHODS OF PRODUCING CARBOXYLIC ACID ESTER DERIVATIVES AND INTERMEDIATES FOR USE IN THE METHODS

[75] Inventors: Masakatsu Matsumoto, Sagamihara; Nobuko Watanabe, Tokyo; Eiko Mori, Tokyo; Hisako Kobayashi, Tokyo; Hiroshi Ikawa, Tokyo, all of Japan

[73] Assignee: Fujirebio Inc., Tokyo, Japan

[21] Appl. No.: 288,197

[22] Filed: Aug. 9, 1994

[30] Foreign Application Priority Data

Aug. 9, 1993 [JP] Japan .................................... 5-214812
Aug. 25, 1993 [JP] Japan .................................... 5-230769

[51] Int. Cl.[6] ...................... C07D 319/06; C07C 69/616
[52] U.S. Cl. .......................... 549/375; 549/333; 556/437; 560/59; 560/60
[58] Field of Search .................................... 549/375, 333; 560/60, 59; 556/437

[56] References Cited

U.S. PATENT DOCUMENTS 5,049,577 9/1991 Varma et al. .

FOREIGN PATENT DOCUMENTS 0617000 9/1994 European Pat. Off. .
WO89/05639 6/1989 WIPO .

OTHER PUBLICATIONS

J. Med. Chem., 1987, vol. 30, pp. 1858–1873, Clayton N. Heathcock, et al., "Total Synthesis and Biological Evaluation of Structural Analogues of Compactin and Dihydromevinolin".
Tetrahedron Letters, vol. 28, No. 13, pp. 1385–1388, 1987, J. E. Lynch, et al., "Synthesis of an HMG–CoA Reductase Inhibitor; A Diastereoselective Aldol Approach".
Tetrahedron Letters, vol. 33,. No. 49, pp. 7525–7526, 1992, Tatsuya Mimani, et al., "A Novel Enantioselective Synthesis of HMG Co–A Reductase Inhibitor NK–104 and a Related Compound".
Tetrahedron Letters, vol. 31, No. 18, 1990, G. Wess, et al., "Stereoselective Synthesis of HR 780 A New Highly Potent HMG–CoA Reductase Inhibitor", pp. 2545–2548.

*Primary Examiner*—Nicky Chan
*Attorney, Agent, or Firm*—Oblon, Spivak, McClelland, Maier & Neustadt

[57] ABSTRACT

Methods of producing carboxylic acid ester derivatives of formulae (I) and (II), which are useful, for instance, as intermediates for producing an anti-hypercholesterolemic agent having an inhibitory effect on HMG-CoA Reductase:

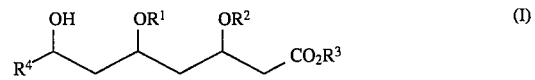

(I)

wherein $R^1$ and $R^2$ are independently a protective group for hydroxyl group, or $R^1$ and $R^2$ integrally constitute a protective group for hydroxyl groups; $R^3$ is an alkyl group, or an aryl group; and $R^4$ is a substituted aryl group, a substituted heterocyclic group, a substituted vinyl group, or a substituted cycloalkenyl group; and

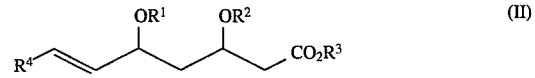

(II)

wherein $R^1$, $R^2$, $R^3$ and $R^4$ are respectively the same as defined in the above formula (I), are disclosed. In addition, intermediates for use in these methods of producing the carboxylic acid ester derivatives are disclosed.

11 Claims, No Drawings

METHODS OF PRODUCING CARBOXYLIC ACID ESTER DERIVATIVES AND INTERMEDIATES FOR USE IN THE METHODS

BACKGROUND OF THE INVENTION

1. Field of the Invention

The present invention relates to methods of producing carboxylic acid ester derivatives of formulae (I) and (II), which are useful, for instance, as intermediates for producing an anti-hypercholesterolemic agent having an inhibitory effect on 3-hydroxy-3-methylgulary-CoA Reductase (hereinafter referred to as HMG-CoA Reductase), in particular, through deprotection or the like. The present invention also relates to intermediates for use in the methods of producing the carboxylic acid ester derivatives:

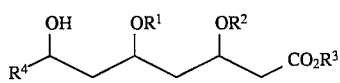

(I)

wherein $R^1$ and $R^2$ are independently a protective group for hydroxyl group, or $R^1$ and $R^2$ integrally constitute a protective group for hydroxyl groups; $R^3$ is an alkyl group having 1 to 12 carbon atoms, or an aryl group; and $R^4$ is a substituted aryl group, a substituted heterocyclic group, a substituted vinyl group, or a substituted cycloalkenyl group.

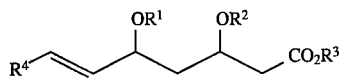

(II)

wherein $R^1$, $R^2$, $R^3$ and $R^4$ are respectively the same as defined in the above formula (I).

2. Discussion of Background

Compounds having as a substituent an (E)-3,5-dihydroxy-6-heptenoic acid moiety which is bonded thereto at the 7-position thereof, which are hereinafter referred to as 7-position-substituted (E)-3,5-dihydroxy-6-heptenoic acid compounds, serve as HMG-CoA Reductase inhibitors. Many methods of synthesizing such 7-position-substituted (E)-3,5-dihydroxy-6-heptenoic acid compounds, including the methods of synthesizing optical active compounds thereof, have been reported.

The substituent at the 7-position of the (E)-3,5-dihydroxy-6-heptenoic acid moiety of the above-mentioned 7-position-substituted (E)-3,5-dihydroxy-6-heptenoic acid compounds (hereinafter referred to the 7-position substituent) is a key substituent for the generation of the inhibitory activity against the HMG-CoA Reductase. Examples of such a 7-position substituent include a substituted aryl group, a substituted heterocyclic group, a substituted vinyl group, and a substituted cycloalkenyl group.

Methods of introducing the 3,5-dihydroxy-6-heptenoic acid unit into this 7-position substituent can be roughly classified into the following three methods:

(I) A method of introducing a C3 carbon chain into the 7-position substituent, followed by the introduction of a C4 carbon chain. As the C3 carbon chain, 2-propenal or a 2-propene acid derivative is employed in this method.

This method includes, for instance, the following specific methods:

(I-1) A method of introducing as the C4 carbon chain a β-keto ester (J. Med. Chem. 1986, 29, 170, J. Org. Chem. 1991, 56, 5752).

(I-2) A method of introducing as the C4 carbon chain a C2 carbon chain for asymmetric induction, followed by the introduction of a C2 carbon chain (Tetrahedron Lett, 1984, 25, 5031).

(I-3) A method of introducing as the C4 carbon chain an optical active C4 carbon chain which is derived from isoascorbic acid through complicated steps (Tetrahadron Lett, 1985, 26, 2951).

(II) A method of introducing a C1 carbon chain into the 7-position substituent structure, followed by the introduction of a C6 carbon chain.

This method includes, for instance, the following specific methods:

(II-1) A method of allowing a formyl group introduced into the 7-position substituent to react with an optically active Horner-Emmons Reagent having a C6 carbon chain (J. Med. Chem. 1987, 30, 1858).

(II-2) A method of utilizing a substituted sulfinylmethyl group introduced into the 7-position substituent (Tetrahadron Lett. 1985, 25, 2947).

(II-3) A method of utilizing the Witrig reagent or Horner-Emmons reagent converted from the halomethyl group introduced into the 7-position substituent (Tetrahadron Lett. 1982, 23, 4305, Tetrahadron Lett. 1990, 31, 2545).

(III) A method of directly introducing a C7 carbon chain in the 7-position substituent or utilizing a halide compound serving as the 7-position substituent.

This method includes, for instance, the following specific methods:

(III-1) A method of utilizing Heck-Reaction employing a C7 carbon chain having a carbon-carbon unsaturated bond at the terminal thereof (J. Med. Chem. 1990, 33, 31).

(III-2) A method of utilizing the reaction between a silyl-substituted epoxy compound having a C7 carbon chain and an anion species prepared from a halide compound (Tetrahedron Lett. 1992, 33, 4183).

(III-3) A method of utilising a Heck type reaction between a tin-olefin compound synthesized from the above-mentioned silyl-substituted epoxy compound having a C7 carbon chain and a halide compound (Tetrahadron Lett. 1992, 33, 4183).

None of the above-mentioned methods, however, is suitable for industrial production of the 7-position-substituted (E)-3,5-dihydroxy-6-heptenoic acid compounds because of the following respective shortcomings:

In the methods (I-1), (I-2) and (I-3), and (II-1), a reduction reaction which is apt to cause problems with respect to the reproducibility thereof is required at a stage close to the final stage of the synthesis of the desired product.

The method (II-2) is complicated because it includes a number of steps after the introduction of the C6 carbon chain.

The method (II-3) not only requires multi-stage steps for synthesizing Witig reagent and Horner-Emmons reagent, but also has the problems with respect to the yields of the products obtained by witig reaction and Horner-Emmons reaction.

The methods (III-1) and (III-3) require an expensive palladium catalyst.

The method (III-2) requires complicated steps for producing the silyl-substituted epoxy compound to be employed therein.

SUMMARY OF THE INVENTION

It is therefore a first object of the present invention to provide a method of producing carboxylic acid ester derivatives of formulae (I) and (II) easily and with high yield:

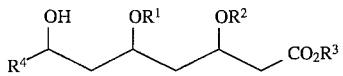

wherein $R^1$ and $R^2$ are independently a protective group for hydroxyl group, or $R^1$ and $R^2$ integrally constitute a protective group for hydroxyl groups; $R^3$ is an alkyl group having 1 to 12 carbon atoms, or an aryl group; and $R^4$ is a substituted aryl group, a substituted heterocyclic group, a substituted vinyl group, or a substituted cycloalkenyl group; and

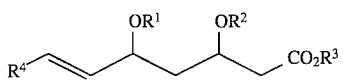

wherein $R^1$, $R^2$, $R^3$ and $R^4$ are respectively the same as defined in the above formula (I).

This object of the present invention can be achieved by allowing a heptenoate derivative of formula (III) to react with an organometallic reagent derived from a halogenated compound having formula (IV) to produce the carboxylic acid ester derivative of formula (I), and then dehydrating the carboxylic acid derivative of formula (I) to produce the carboxylic acid ester derivative of formula (II) in accordance with the following reaction scheme

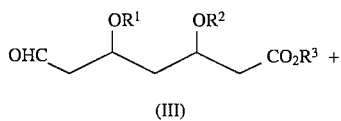

Organometallic reagent derived from $R^4$—$X^1$ ⟶
(IV)

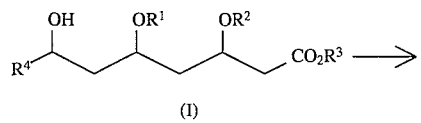

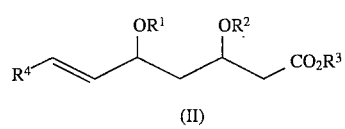

In the above reaction scheme, $R^1$, $R^2$, $R^3$ and $R^4$ are respectively the same as defined in the above formula (I), and $X^1$ in formula (IV) is a halogen atom such as chlorine, bromine or iodine.

A second object of the present invention is to provide intermediates for producing the above carboxylic acid eater derivatives of formulae (I) and (II).

DESCRIPTION OF THE PREFERRED EMBODIMENTS

In the heptanoate derivative of formula (III) for use in the present invention,

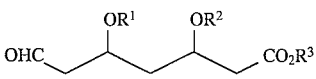

wherein $R^1$ and $R^2$ are independently a protective group for hydroxyl group, or $R^3$ and $R^2$ integrally constitute a protective group for hydroxyl groups; and $R^3$ is an alkyl group having 1 to 12 carbon atoms, or an aryl group, specific examples of the protective group for hydroxyl group represented by $R^1$ or $R^2$ are an alkyl group having a substituent, such as methoxymethyl group, ethoxymethyl group, methoxyethyl group and benzyl group; an alkenyl group having 2 to 6 carbon atoms, such as allyl group and methallyl group; a heterocyclic group such as 2-tetrahydropyranyl group, 2-tetrahydrothiopyranyl group and 2-tetrahydrofuranyl group; a substituted silyl group such as trimethylsilyl group, t-butyldimethylsilyl group and dimethylphenylsilyl group; an acyl group such as formyl group, acetyl group and benzoyl group; a substituted oxycarbonyl group such as t-butoxycarbonyl group, methoxycarbonyl group and benzyloxycarbonyl group; and a substituted carbamoyl group such as N-phenylcarbamoyl group.

Furthermore, in the heptanoate derivative of formula (III), examples of the protective group formed integrally by $R^1$ and $R^2$ include methylene group, an alkylidene group having 2 to 10 carbon atoms, such as ethylidene group, propylidene group, isopropylidene group, benzylidene group, cyclopentylidene group and cyclohexylidene group; and a carbonyl group.

In the heptenoate derivative of formula (III), the alkyl group represented by $R^3$ is, for example, a straight, branched or cyclic alkyl group having 1 to 12 carbon atoms, preferably 1 to 4 carbon atoms.

Specific examples of such an alkyl group include methyl group, ethyl group, propyl group, butyl group, pentyl group, hexyl group, heptyl group, octyl group, nonyl group, decyl group, undecyl group, dodecyl group, isopropyl group, s-butyl group, t-butyl group, cyclopentyl group and cyclohexyl group.

The alkyl group represented by $R^3$ may have a substituent. Examples of such a substituted alkyl group include benzyl group, phenethyl group, and naphthylmethyl group.

In the heptanoate derivative of formula (III), $R^3$ may be an aryl group. Examples of the aryl group represented by $R^3$ include phenyl group and naphthyl group.

Specific examples of the heptanoate derivative of formula (III) are as follows;
methyl 3,5-bis(methoxymethoxy)-7-oxoheptanoate,
methyl 3,5-bis(ethoxymethoxy)-7-oxoheptanoate,
methyl 3,5-bis(2-methoxyethoxy)-7-oxoheptanoate,
methyl 3,5-dibenzyloxy-7-oxoheptanoate,
methyl 7-oxo-3,5-bis(2-propenyloxy)heptanoate,
methyl 3,5-bis(2-methyl-2-propenyloxy)-7-oxoheptanoate,
methyl 7-oxo-3,5-bis(tetrahydropyran-2-yloxy)heptanoate,
methyl 3,5-bis(trimethylsllyloxy)-7-oxoheptanoate,
methyl 3,5-bis(t-butyldimethylsilyloxy)-7-oxoheptanoate,
methyl 3,5-bis(dimethylphenylsilyloxy)-7-oxoheptanoate,
methyl 3,5-bis(formyloxy)-7-oxoheptenoate,
methyl 3,5-diacetoxy-7-oxoheptanoate,
methyl 3,5-bis(benzoyloxy)-7-oxoheptenoate,
methyl 3,5-bis(t-butoxycarbonyloxy)-7-oxoheptanoate, methyl 3,5-bis(methoxycarbonyloxy)-7-oxoheptanoate,
methyl 3,5-bis(benzyloxycarbonyloxy)-7-oxoheptanoate,
methyl 3,5-bis(N-phenylcarbamoyloxy)-7-oxoheptanoate,
methyl 7-oxo-3,5-O-methylidene-3,5-dihydroxyheptanoate,
methyl 7-oxo-3,5-O-ethylidene-3,5-dihydroxyheptanoate,
methyl 7-oxo-3,5-O-isopropylidene-3,5-dihydroxyheptanoate,
methyl 7-oxo-3,5-O-benzylidene-3,5-dihydroxyheptanoate,
methyl 7-oxo-3,5-O-cyclopentylidene-3,5-dihydroxyheptanoate,
methyl 7-oxo-3,5-O-cyclohexylidene-3,5-dihydroxyheptanoate,
methyl 7-oxo-3,5-O-carbonyl-3,5-dihydroxyheptenoate,
ethyl 7-oxo-3,5-O-isopropylidene-3,5-dihydroxyheptanoate,
propyl 7-oxo-3,5-O-isopropylidene-3,5-dihydroxyheptanoate,
t-butyl 7-oxo-3,5-O-isopropylidene-3,5-dihydroxyheptanoate, and
phenyl 7-oxo-3,5-O-isopropylidene-3,5-dihydroxyheptanoate.

The heptanoate derivative of formula (III) can be produced in accordance with the following reaction scheme:

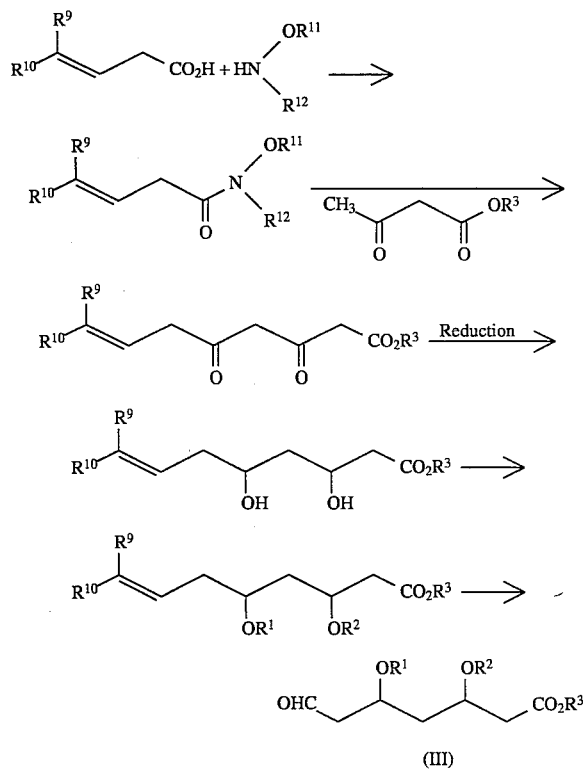

wherein $R^1$, $R^2$, and $R^3$ are respectively the same as defined in the previously mentioned formula (1), $R^9$ and $R^{10}$ each is a hydrogen atom, an alkyl group, an aryl group, or a heterocyclic group, and $R^9$ and $R^{10}$ may integrally form a cycloalkylidene group, and $R^{11}$ and $R^{12}$ each is an alkyl group.

As mentioned previously, in the carboxylic acid ester derivatives of formulae (I) and (II), the substituent $R^4$ is a substituted aryl group, a substituted heterocyclic group, a substituted vinyl group or a substituted cylcoakenyl group.

Of heptenoic acid derivatives which include any of the above-mentioned substituents $R^4$ and which also include a 4-fluorophenyl group as a substituent for the substituent $R^4$, there are compounds represented by formula $R^4$—$X^1$ that can be used as starting materials for producing compounds having an inhibitory effect on HMG-CoA Reductase.

A method of producing such a starting material of formula $R^4$—$X^1$, in which $R^4$ is an aryl group having as a substituent a 4-fluorophenyl group, will now be explained as follows:

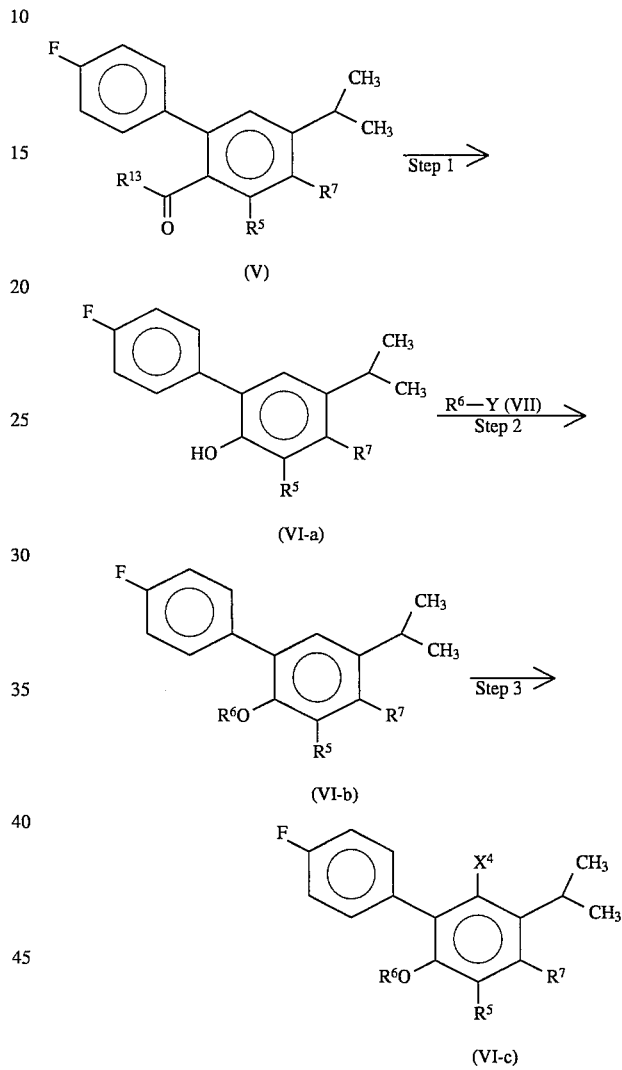

In the above reaction scheme, $R^5$ is a halogen atom, an alkyl group having 1 to 6 carbon atoms, or a group represented by $R^8O$—, in which $R^8$ is a hydrogen atom, or an alkyl group having 1 to 6 carbon atoms; $R^6$ is an alkyl group having 1 to 6 carbon atoms, but is not a hydrogen atom in the above reaction scheme; as starting materials represented by formula (VI-b) or (VI-c), however, $R^6$ and $R^7$ each is a hydrogen atom, or an alkyl group having 1 to carbon atoms; $R^8$ and $R^6$ may form a five- or six-membered ring in combination with the oxygen atom to which each of $R^8$ and $R^6$ is bonded; $R^8$ and $R^7$ may form a five- or six-membered ring in combination with the oxygen atom to which $R^8$ is bonded; $X^4$ is a halogen atoms $R^{13}$ is an alkyl group having 1 to 6 carbon atoms, or an alkoxyl group having 1 to 6 carbon atoms; and Y is a halogen atom or a substituted sulfonyloxy group.

The compounds in the above reaction scheme will now be explained in detail.

As mentioned above, $R^5$ is a halogen atom, an alkyl group having 1 to 6 carbon atoms, or a group represented by $R^8O—$, in which $R^8$ is a hydrogen atom, or an alkyl group having 1 to 6 carbon atoms.

Examples of the halogen atom represented by $R^3$ are fluorine, chlorine, bromine and iodine.

Examples of the alkyl group having 1 to 6 carbon atoms represented by $R^5$ include methyl group, ethyl group, n-propyl group, 2-propyl group, n-butyl group, sec-butyl group, t-butyl group, n-pentyl group, and n-hexyl group.

The alkyl group having 1 to 6 carbon atoms represented by $R^5$ may have a substituent.

Examples of the substituent of the alkyl group having 1 to 6 carbon atoms represented by $R^3$ are a hydroxyl group, an alkoxyl group having 1 to 6 carbon atoms, which may have a substituent, an aryl group, and a heterocyclic group.

Specific examples of the alkyl group having 1 to 6 carbon atoms represented by $R^3$ which has a hydroxyl group as a substituent are hydroxyethyl group, 3-hydroxypropyl group, 4-hydroxybutyl group, 5-hydroxypentyl group, and 6-hydroxyhexyl group.

Specific examples of the above-mentioned alkoxyl group having 1 to 6 carbon atoms, which may have a substituent, are methoxy group, ethoxy group, propoxy group, butoxy group, pentyloxy group, hexyloxy group, methoxymethoxy group, methoxyethoxy group, methoxypropoxy group, ethoxyethoxy group, and ethoxypropoxy group.

Specific examples of the alkyl group having 1 to 6 carbon atoms represented by $R^3$ which has as a substituent an alkoxyl group having 1 to 6 carbon atoms, which may have a substituent, are methoxymethyl group, methoxyethyl group, methoxypropyl group, ethoxyethyl group, ethoxypropyl group, methoxymethoxyethyl group, methoxyethoxyethyl group, ethoxyethoxymethyl group, methoxymethoxypropyl group, and methoxyethoxymethyl group.

Specific examples of the aryl group are phenyl group and naphthyl group.

Specific examples of the alkyl group having 1 to 6 carbon atoms represented by $R^5$ which has an aryl group as a substituent are benzyl group, phenetyl group, 3-phenylpropyl group, 4-phenylbutyl group, 5-phenylbutyl group, 6-phenylhexyl group, 1-naphthylmethyl group, 2-naphthylmethyl group, 1-naphthylethyl group, and 2-naphthylethyl group.

Specific examples of the heterocyclic group are furyl group, thienyl group and pyridyl group.

Specific examples of the alkyl group having 1 to 6 carbon atoms represented by $R^5$ which has a heterocyclic group as a substituent are 2-pyridylmethyl group, 3-pyridylmethyl group, 4-pyridylmethyl group, 2-pyridylethyl group, 3-pyridylethyl group, 4-pyridylethyl group, 2-pyridylpropyl group, 2-pyridylbutyl group, furfuryl group, 2-furylmethyl group, 2-thenyl group, 3-thienylmethyl group, 2-thienylethyl group, and 2-thienylpropyl group.

As mentioned previously, $R^6$ and $R^7$ each is a hydrogen atom, or an alkyl group having 1 to 6 carbon atoms. The alkyl group represented by $R^6$ or $R^7$ is the same alkyl group as represented by $R^5$ and may have the same substituent as for the alkyl group represented by $R^5$.

$R^8$ and $R^6$ may form a five- or six-membered ring in combination with the oxygen atom to which each of $R^8$ and $R^6$ is bonded.

Specific examples of the five-membered ring are a dioxolan ring, and a dioxolan ring having a methyl group or ethyl group as a substituent.

Specific examples of the six-membered ring are a dioxane ring and a dioxane ring having a methyl group or ethyl group as a substituent.

$R^8$ and $R^7$ may form a five- or six-membered ring in combination with the oxygen atom to which $R^8$ is bonded. Specific examples of such a ring are a dihydrofuran ring, a dihydrofuran ring, a methyldihydrofuran ring, a dimethyldihydrofuran ring, a methyldihydropyran rang, and a dimethyldihydropyran ring.

$R^{13}$ is an alkyl group having 1 to 6 carbon which is the same alkyl group as represented by $R^5$, or an alkoxyl group having 1 to 6 carbon atoms. $X^4$ is a halogen atom such as chlorine, bromine, and iodine; and Y is a halogen atom or a substituted sulfonyloxy group.

[Step 1]

In this step, a ketone derivative of formula (V) is oxidized, so that a 4-fluorobiphenyl derivative of formula (VI-a) is produced.

This step can be carried out by the conventionally known Dakin Reaction or Baeyer-Villiger Reaction. Examples of an oxidizing agent for use in this step are hydrogen peroxide, peracetic acid, trifluoroperacetic acid, perbenzoic acid, and m-chloroperbenzoic acid.

Peracetic acid or trifluoroperacetic acid can be produced in a reaction system in which hydrogen peroxide is used in the presence of acetic acid or trifluoroacetic acid.

The reaction in this step can be carried out in the presence of a solvent. Examples of a solvent for use in this step include alcohols such as methanol, ethanol, butanol, and trifluoroethanol; ethers such as diethyl ether, 1,2-dimethoxyethane (DME), tetrahydrofuran (THF) and 1,4-dioxane; halogenated hydrocarbons such as dichloromethane, chloroform, carbon tetrachloride, and 1,2-dichloroethane; hydrocarbons such as hexane, octane, benzene, and toluene; and water. These solvents can be employed alone or in combination.

When the reaction is carried out in the presence of a base, alkali metal hydroxides and alkaline earth metal hydroxides such as sodium hydroxide, potassium hydroxide, calcium hydroxide, and barium hydroxide can be employed as such a base.

The reaction can be usually carried out at temperatures in the range of −30° C. to 100° C.

In the case where an acyloxy compound is produced in the above reaction, the step of hydrolyzing the acyloxy compound is required after the oxidation step. Such hydrolysis can be easily carried out by conventionally known methods.

The ketone derivative of formula (V) used as the starting material in this step can be produced in accordance with the following reaction scheme:

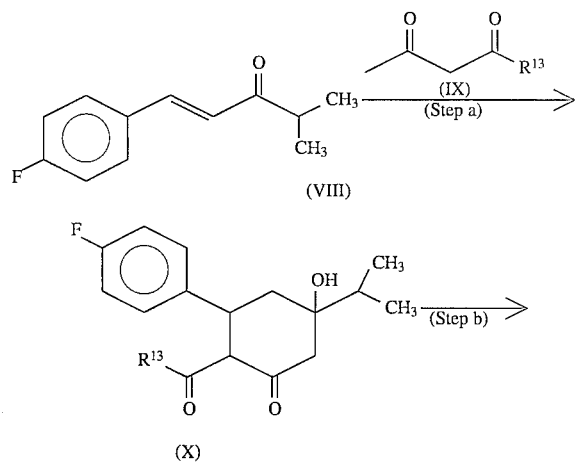

-continued

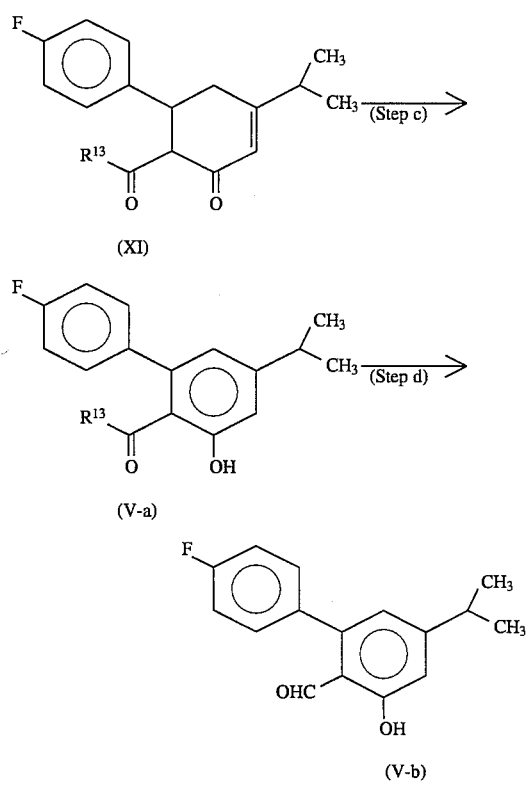

In the above reaction scheme, $R^{13}$ is an alkyl group having 1 to 6 carbon atoms, or an alkoxyl group having 1 to 6 carbon atoms in the formulae (IX), (X), (XI) and (V-a). However, the step d proceeds when $R^{13}$ is the alkoxyl group.

[Step a]

In this step, 1-(4-fluorophenyl)-4-methyl-1-penten- 3-on of formula (VIII) is allowed to react with an acetone derivative of formula (IX) in the presence of a base to carry out a cyclic addition reaction, whereby a cyclohexanone derivative of formula (X) is produced.

It is preferable to use a base in the cyclic addition reaction. Examples of a base for use in the addition reaction are alkali metal alkoxides such as sodium methoxide, sodium ethoxide, sodium t-butoxide, and potassium t-butoxide; alkali metal carbonates such as sodium hydrogencarbonate, sodium carbonate, and potassium carbonate; alkali metal hydrides such as sodium hydride, potassium hydride, and calcium hydride; alkali metal hydroxides and alkaline earth metal hydroxides such as sodium hydroxide, potassium hydroxide, calcium hydroxide, and barium hydroxide; and organic bases such as pyridine, picoline, collidine, triethylamine, 1,8-diazabicyclo[5,4,0]undec-7-ene (DBU), 1,5-diazobicyclo[4,3,0]nona-5-ene (DBN), 1,4-diazabicyclo[2,2,2]octane (DABCO), and 4-(dimethylamino)pyridine (DMAP).

The reaction is carried out in a solvent which is inert to the reaction. Examples of such a solvent include alcohols such as methanol, ethanol, propanol, and butanol; ethers such as diethyl ether, DME, THF, and 1,4 -dioxane; and aromatic hydrocarbons such as benzene, toluene, and xylene.

The reaction can be usually carried out at temperatures in the range of –78° C. to 120° C.

[Step b]

In this step, the cyclohexanone derivative of formula (X) is subjected to a dehydration reaction to produce a cyclohexenone derivative-of formula (XI). This dehydration reaction can be carried out in the presence of a basic catalyst or acid catalyst.

Examples of the acid catalyst are mineral acids such as hydrochloric acid, sulfuric acid, and phosphoric acid; organic acids such as acetic acid and trifluoro-acetic acid; organic sulfonic acid and salts thereof such as pyridinium p-toluenesulfonate, p-toluenesulfonic acid, and benzenesulfonic acid.

It is preferable that the reaction be carried out within a solvent. Examples of such a solvent for use in the reaction are alcohols such as methanol, ethanol and propanol; aromatic hydrocarbons such as benzene, toluene and xylene; halogenated hydrocarbons such as dichloromethane, chloroform, carbon tetrachloride, and 1,2-dichloroethane; and water. These solvents can be used alone or in combination.

When the reaction is carried out under nonaqueous conditions, the reaction is carried out in the presence of a dehydrating agent such anhydrous magnesium sulfate or calcium chloride in the reaction system.

The reaction can be usually carried out at temperatures in the range of 0° C. to 160° C.

When the dehydration reaction is carried out in the presence of a basic catalyst, the same bases as employed in Step a can be employed as such a basic catalyst. Therefore, Step b can be carried out without isolating the compound of formula (X), whereby a compound of formula (XI) can be produced.

[Step c]

In this step, the cyclohexenone derivative of formula (XI) is subjected to an aromatic cyclization reaction, whereby a phenol derivative of formula (V-a) is produced.

For this reaction, a method utilizing a dehydrogenation-oxidation reaction in the presence of a metallic catalyst or a method utilizing an oxidative dehalogenation reaction can be employed.

Examples of a metallic catalyst for use in the dehydrogenation-oxidation reaction are platinum, palladium, iridium, rhodium, and nickel. The reaction can be appropriately carried out within a solvent. Examples of a solvent for use in this reaction are ethers such as diethyleneglycol dimethyl ether, diethyleneglycol diethyl ether; aromatic hydrocarbons such as cumene, p-cymene, naphthalene, and nitrobenzene; and heterocyclic aromatic hydrocarbons such as quinoline.

A hydrogen acceptor may be placed in the reaction system in order to eliminate the hydrogen generated during the course of the dehydrogenation reaction. Examples of such a hydrogen acceptor are unsaturated ketones such as isophorone; and unsaturated carboxylic acids such as cinnamic acid and maleic acid, and esters thereof.

The above reaction can be usually carried out at temperatures in the range of 100° C. to 200° C.

For the purpose of the oxidative dehalogenation reaction, a halogenating agent, for instance, copper (II) chloride, copper (II) bromide, and pyridinium bromide perbromide can be employed, and after the elimination of a halogenated compound which is generated in the course of the halogenation reaction, a hydrogen halide elimination reaction may be carried out. This reaction can be carried out in a solvent which is inert to the reaction. Examples of such a solvent are halogenated hydrocarbons such as dichloromethane, chloroform, carbon tetrachloride, and 1,2-dichloroethane; esters such as methyl acetate and ethyl acetate; and carboxylic acids such as acetic acid and propionic acid.

This reaction can be usually carried out at temperatures in the range of −30° C. to 160° C.

[Step d]

In this step, the phenol derivative of formula (V-a) is allowed to react with a reducing agent, whereby an aldehyde derivative of formula (V-b) is produced, provided that in this step, $R^{13}$ in formula (V-a) is an alkoxyl group, preferably an alkoxyl group having 1 to 6 carbon atoms. Therefore, the phenol derivative of formula (V-a) may be referred to as the ester derivative. The aldehyde derivative of formula (V-b) may also be referred to as the phenol derivative since it includes a hydroxyl group bonded to the phenyl group.

In this step, any reducing agent can be employed so long as it is capable of converting ester to aldehyde. Specific examples of such a reducing agent are disobutyl aluminum hydride (DIBAL), sodium bis (2-methoxyethoxy)aluminum hydride (SBMEA), and sodium aluminum hydride.

It is preferable that the reaction be carried out in a solvent in an atmosphere of an inert gas.

Examples of the solvent for use in this reaction are aromatic hydrocarbons such as benzene, toluene and xylene; ethers such as diethyl ether, DME, THF, 1,4-dioxane; and saturated hydrocarbons such as pentane, hexane and heptane. These solvents can be used alone or in combination.

The reaction can be usually carried out at temperatures in the range of −78° C. to room temperature.

When the aldehyde derivative of formula (V-b) is produced from the ester derivative of formula (V-a), a method comprising the steps of reducing the ester derivative of formula (V-a) an alcohol derivative, and then oxidizing the thus formed alcohol derivative to the aldehyde derivative of formula (V-b) by use of an oxidizing agent can be employed.

Specific examples of such an oxidizing agent include chrome compounds such as pyridinium chlorochromate, and pyridinium dichromate; dimethylsulfoxide (DMSO)-pyridinium sulfur trioxide;DMSO-oxalyl chloride; and DISO-acetic anhydride.

In the phenol derivative of formula (V-a) obtained in the previously mentioned Step c, and the phenol derivative of formula (V-b) obtained in the above-mentioned Step d, a substituent can be easily introduced into the hydroxyl group thereof by allowing those phenol derivatives to react with an alkyl halide or a substituted alkyl halide.

[Step 2]

In this step, 4-fluorobiphenyl derivative of formula (VI-a) obtained in 1st Step is allowed to react with an alkylating agent of formula (VII) in the presence of a base, whereby a 4-fluorobiphenyl derivative of formula (VI-b) is produced.

Examples of Y in formula (VII) include a halogen atom such as chlorine, bromine and iodine; a substituted sulfonyloxy group such as methanesulfonyloxy group, p-toluenesulfonyloxy group, and an alkoxysulfonyloxy group.

Examples of the base for use in the above reaction are alkali metal carbonates such as sodium hydrogencarbonate, potassium hydrogencarbonate, sodium carbonate, and potassium carbonate; alkali metal hydrides such as sodium hydride, potassium hydride, and calcium hydride; alkali metal hydroxides and alkaline earth metal hydroxides such as sodium hydroxide, potassium hydroxide, calcium hydroxide, and barium hydroxide; and organic bases such as pyridine, picoline, collidine, triethylamine, DBU, DBN, DABCO, and DMAP.

The reaction can be carried out in a solvent which is inert to the reaction. Examples of such a solvent are alcohols such as methanol, ethanol, propanol and butanol; ethers such as diethyl ether, DME,.THF, 1.4-dioxane; amides such as N,N-dimethylformamide, and N,N-dimethylacetamide; and ketones such as acetone, and 2-butanone. These solvents can be used alone or in combination.

This reaction can be usually carried out at temperatures in the range of −30° C. to 150° C.

[Step 3]

In this step, 4-fluorobiphenyl derivative of formula (VI-b) obtained in Step 2 is allowed to react with a halogenating agent to produce a 4-fluorobiphenyl derivative of formula (VI-c).

Specific examples of such a halogenating agent are chlorine, bromine, N-bromosuccinimide, N-chlorosuccinimide, and pyridinium bromide perbromide.

This reaction can be carried out in a solvent which is inert to the reaction. Examples of such a solvent are halogenated hydrocarbons such as dichloromethane, chloroform, carbon tetrachloride, and 1,2-dichloroethane; ethers such as diethyl ether, DME, THF, and 1,4-dioxane; organic carboxylic acids such as acetic acid and trifluoroacetic acid; and water. These solvents can be used alone or in combination.

This reaction can be used usually carried out at temperatures in the range of −30° C. to 160° C.

In the 4-fluorobiphenyl derivative of formula (VI-c) produced in Step 3, as mentioned previously, $R^5$ is a halogen atom, an alkyl group having 1 to 6 carbon atoms, or a group represented by $R^8O—$, in which $R^8$ is a hydrogen atom or an alkyl group having 1 to 6 carbon atoms.

The 4-fluorobiphenyl derivative of formula (VI-c), in which $R^3$ is a halogen atom or an alkyl group having 1 to 6 carbon atoms, can be produced by a method comprising the steps of:

(i) subjecting the following compound of formula (XII) to a halogenation or alkylation reaction,

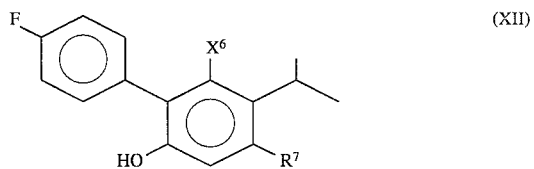

wherein $R^1$ is the same as defined in formula (VI-c), and $X^6$ is a hydrogen atom, a halogen atom or a formyl group;

and (ii) performing the previously mentioned Step 2 under the same conditions as mentioned previously.

The above halogenation reaction can be carried out by use of the same halogenating agents as employed in Step 3 under the same conditions as in Step 3.

The alkylation reaction can be carried out by use of the previously mentioned compound of formula (VII) in the presence of a base, preferably in a non-polar solvent.

Examples of the base for use in the above reaction include alkali metal hydroxides such as lithium hydroxide, sodium hydroxide, and potassium hydroxide; and alkyl lithiums such as methyl lithium and butyl lithium.

Examples of the non-polar solvent for use in the above reaction include hydrocarbons such as benzene, toluene and xylene.

The reaction can be usually carried out at temperatures in the range of 0° C. to 150° C.

Specific examples of the 4-fluorobiphenyl derivatives of formulae (VI-a), (VI-b) and (VX-c) synthesized in the above-mentioned Steps 1, 2 and 3 are as follows:

2-bromo-4'-fluoro-5,6-dimethoxy-3-(propan-2-yl)biphenyl,
2-bromo-5,6-diethoxy-4'-[fluoro-3-(propan-2-yl)biphenyl,
5,6-dibenzyloxy-2-bromo-4'-fluoro-3-(propan-2-yl)biphenyl,
2-bromo-4'-fluoro-5,6-methylenedioxy-3-(propan-2-yl)biphenyl, 2-bromo-4'-fluoro-5,6-(dimethylmethylene)dioxy-3-(propan-2-yl)biphenyl,
2-bromo-4'-fluoro-5,6-bis(2-methoxyethoxy)-3-(propan-2-yl)biphenyl,
6-benzyloxy-2-bromo-4'-fluoro-5-methoxy-3-(propan-2-yl)biphenyl,
2-bromo-4'-fluoro-5-methoxy-6-(2-methoxyethoxy)-3-(propan-2-yl)biphenyl,
2-bromo-4'-[fluoro-5-methoxy-6-[2-(2-methoxyethoxy)ethoxy]-3-(propan-2-yl)biphenyl,
6-bromo-5-(4'-fluorophenyl)-7-(propan-2-yl)-1,4 -benzodioxane,
5-bromo-6-(4'-fluorophenyl)-2,3-dihydro-7-methoxy-2,2-dimethyl-4-(propan-2-yl)benzo[b]furan,
5-bromo-7-ethoxy-6-(4'-fluorophenyl)-2,3-dihydro-2,2 -dimethyl-4-(propan-2-yl)benzo[b]furan,
5-bromo-6-(4'-fluorophenyl)-2,3-dihydro-7-(2-methoxyethoxy)-2,2-dimethyl-4-(propan-2-yl)benzo[b]furan,
7-benzyloxy-5-bromo-6-(4'-fluorophenyl)-2,3-dihydro-2,2 -dimethyl-4-(propan-2-yl)benzo[b]furan,
5-bromo-6-(4'-fluorophenyl)-2,3-dihydro-7-[2-(2-methoxyethoxy)ethoxy] -2,2-dimethyl-4-(propan-2-yl)benzo[b]furan,
4'-fluoro-2,3-dimethoxy-5-(propan-2-yl)biphenyl,
2,3-diethoxy-4'-fluoro-5-(propan-2-yl)biphenyl,
2,3-dibenzyloxy-4'-fluoro-5-(propan-2-yl)biphenyl,
4'-fluoro-2,3-methylenedioxy-5-(propan-2-yl)biphenyl,
4'-fluoro-2,3-(dimethylmethylene)dioxy-5-(propan-2-yl)biphenyl,
4'-fluoro-2,3-bis(2-methoxyethoxy)-5-(propan-2-yl)biphenyl,
4'-fluoro-3-methoxy-2-(2-methoxyethoxy)-5-(propan-2-yl)biphenyl,
4'-fluoro-3-methoxy-2-[2-(2-methoxyethoxy)ethoxy]-5 -(propan-2-yl)biphenyl,
5-(4'-fluorophenyl)-7-(propan-2-yl)-1,4-bentodioxane,
6-(4'-fluorophenyl)-2,3-dihydro-7-methoxy-2,2-dimethyl-4 -(propan-2-yl)benzo[b]furan,
7-ethoxy-6-(4'-fluorophenyl)-2,3-dihydro-2,2-dimethyl-4 -(propan-2-yl)benzo[b]furan,
6-(4'-fluorophenyl)-2,3-dihydro-7-(2-methoxyethoxy)-2,2 -dimethyl-4-(propan-2-yl)benzo[b]furan,
7-benzyloxy-6-(4'-fluorophenyl)-2,3-dihydro-2,2-dimethyl-4-(propan-2-yl)benzo[b]furan,
6-(4'-fluorophenyl)-2,3-dihydro-7-[2-(2-methoxyethoxy)ethoxy]-2,2-dimethyl-4-(propan-2-yl)benzo[b]furan,
4'-fluoro-5-(propan-2-yl)biphenyl-2,3-diol,
4'-fluoro-3-methoxy-5-(propan-2-yl)biphenyl-2-ol,
6-(4'-fluorophenyl)-2,3-dihydro-2,2-dimethyl-4-(propan-2-yl)benzo[b]furan-7-ol,
4'-fluoro-6-methoxy-5-methyl-3-(propan-2-yl)biphenyl,
5-ethyl-4'-fluoro-6-methoxy-3-(propan-2-yl)biphenyl,
4',5-difluoro-6-methoxy-3-(propan-2-yl)biphenyl,
5-chloro-4'-fluoro-6-methoxy-3-(propan-2-yl)biphenyl,
5-bromo-4'-fluoro-6-methoxy-3-(propan-2-yl)biphenyl,
4'-fluoro-5-iodo-6-methoxy-3-(propan-2-yl)biphenyl,
2-bromo-4'-fluoro-6-methoxy-5-methyl-3-(propan-2 -yl)biphenyl,
2-bromo-5-ethyl-4'-fluoro-6-methoxy-3-(propan-2 -yl)biphenyl,
2-bromo-4',5-difluoro-6-methoxy-3-(propan-2-yl)biphenyl,
2-bromo-5-chloro-4'- fluoro-6-methoxy-3-(propan-2 -yl)biphenyl,
2,5-dibromo-4'-fluoro-6-methoxy-3-(propan-2-yl)biphenyl, and
2-bromo-4'-fluoro-5-iodo-6-methoxy-3-(propan-2 -yl)biphenyl.

The reaction between the heptenoate derivative of formula (III) and the organometallic reagent derived from the halogenated compound of formula (Iv) can be carried out by mixing the heptenoate derivative of formula (III) and the organometallic reagent, whereby the carbonic acid ester derivative of formula (I) can be obtained.

It is preferable that this reaction be carried out in an inert solvent. Examples of the inert solvent for use in this reaction are ethers such as diethyl ether, dimethoxyethane (DHE), tetrahydrofuran (THF), 1,4 -dioxane, and diglyme. These ethers can be used alone or in combination.

This reaction can be usually carried out at temperatures in the range of −78° C. to 100° C. Furthermore, it is preferable that this reaction be carried out under nonaqueous conditions in an atmosphere of an inert gas such as nitrogen or argon in order to obtain the carboxylic acid ester derivative of formula (I) in a high yield.

The above-mentioned organometallic reagent can be produced by allowing the halogenated compound of formula (IV) to react with an alkali metal or alkaline earth metal, such as lithium and magnesium.

The carboxylic acid ester derivative of formula (II) can be obtained by subjecting the carboxylic acid ester derivative of formula (I) to a dehydration reaction. Such a dehydration reaction is well known and can be performed by use of any of a halogenating agent such as thionyl chloride, thionyl bromide, phosphorous pentachloride, and phosphorous pentabromide; a sulfonating agent such as methanesulfonyl chloride, p-toluenesulfonyl chloride, and benzenesulfonyl chloride; or an esterification agent such as acetyl chloride, and bentoyl chloride, in combination with a base.

Examples of the above-mentioned base are organic bases such as pyridine, picoline, collidine, 4,4 -dimethylaminopyridine (DMAP), triethylamine, 1,5-diazabicyclo[4,3,0]non-5-ene (DBN), 1,8-diazobicyclo[5,4,0]undec-7-ene (DBU), and 1,4-diazabicyclo[2,2,2] -octane (DABCO); and inorganic bases such as sodium hydrogencarbonate, potassium hydrogencarbonate, sodium carbonate, and potassium carbonate.

It is preferable that this reaction be carried out in an inert solvent. Examples of the inert solvent for use in this reaction are aromatic hydrocarbons such as benzene, toluene and xylene; halogenated hydrocarbons such as dichloromethane, 1,2-dichloroethane, chloroform and carbon tetrachloride;esters such as methyl acetate end ethyl acetate.

When an organic base is employed as the above-mentioned base, the organic base may be used in such an amount as to be used as the solvent for this reaction.

The above reaction can be usually carried out at temperatures in the range of −30° C. to 160° C.

The carboxylic acid ester derivative of formula (II) can be converted into the following heptenoic acid derivative which has an inhibitory effect on the HMG-CoA Reductase, by deprotecting the hydroxyl groups protected by $R^1$ and $R^2$, or if necessary, by hydrolyzing the moiety of $—COOR^3$ in the carboxylic acid eater derivative of formula (II):

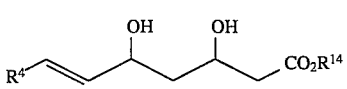

wherein $R^4$ is the same as defined in formula (II), and $R^{14}$ is a hydrogen atom, an alkyl group, an aryl group, or an alkali metal or alkaline earth metal.

In a 4-fluorobiphenyl derivative of formula (VI),

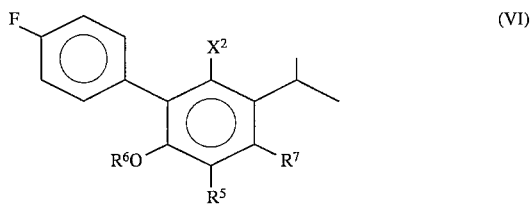

wherein $R^5$, $R^6$, and $R^7$ are respectively as defined previously, and $X^2$ is a hydrogen atom, a formyl group, or a group of formula $X^3$—$CH_2$—, in which $X^3$ is a halogen atom or a hydroxyl group, when $X^2$ is a formyl group, a halogenomethyl group or a hydroxymethyl group, such a 4-fluorobiphenyl derivative of formula (VI) is also useful as an intermediate for producing compounds having an inhibitory effect on HMG-CoA Reductase. By introducing a C6 carbon chain into the above intermediate, the desired compounds can be obtained (refer to Reference Examples described later).

The 4-fluorobiphenyl derivative of the following formula (VI-d), which is the 4-fluorobiphenyl derivative of formula (VI) in which,

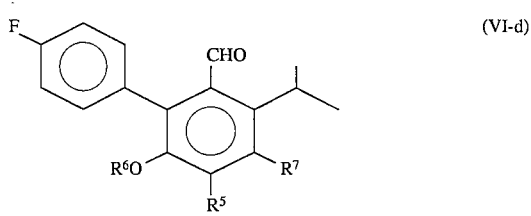

$R^5$ $R^6$ and $R^7$ are respectively as defined previously, and $X^2$ is a formyl group, can be produced by allowing the previously mentioned 4-fluorobiphenyl derivative of formula (VI-c) to react with an alkali metal such as lithium or an alkaline earth metal such as magnesium to prepare an organometallic reagent, and then by allowing this organometallic reagent to react with a formamide, such as N-methylformamide, N,N-dimethyl-formamide, N-formylmorpholine, and N-formylpiperidine; an orthoformic ester, such as methyl orthoformate, and ethyl orthoformate; or ethoxymethylene aniline.

When the above-mentioned organometellic reagent is produced and the produced organometallic reagent is allowed to react with the orthoformic ester or ethoxymethylene aniline, the reaction conditions therefor are the same as those under which the previously mentioned heptenoate derivative of formula (III) is allowed to react with the organometallic reagent derived from the halogenated compound of formula (IV).

The previously mentioned 4-fluorobiphenyl derivative of formula (VI-d) having a formyl group can also be produced by subjecting the 4-fluorobiphenyl derivative of formula (VI-b) to any of Gartermann reaction, Gettermann-Koch reaction, and Vilemeier reaction, or by allowing the 4-fluorobiphenyl derivative of formula (VI-b) to react with a dichloromethyl alkyl ether such as dichloromethyl methyl ether, or dichloromethyl ethyl ether, in the presence of a Lewis acid such as titanium (IV) chloride, or aluminum chloride, and hydrolyzing the product of this reaction.

Furthermore, the following 4-fluorobiphenyl derivative of formula (VI-e), which is the 4-fluorobiphenyl derivative of formula (VI), in which $X^2$ is a halogenomethyl group,

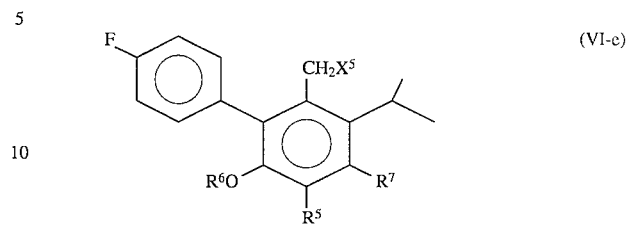

wherein $R^3$, $R^6$, and $R^7$ are respectively as defined previously, and $X^5$ is a halogen atom such as chlorine, bromine or iodine, can be produced by subjecting the previously mentioned 4-fluorobiphenyl derivative of formula (VI-b) to a halogenomethylation reaction.

This halogenomethylation reaction can be carried out, for instance, by allowing the 4-fluorobiphenyl derivative of formula (VI-b) to react with a reagent which comprises a mineral acid such as hydrochloric acid, hydrobromic acid or hydroiodic acid, and formaldehyde, paraformaldehyde, trioxane, dimethoxymethane, halogenomethyl ether or bis(halogenomethyl) ether in combination.

This reaction can be carried out in a solvent. Examples of a solvent for use in this reaction are organic carboxylic acids such as acetic acid and propionic acid; halogenated hydrocarbons such as dichloromethane, chloroform, and carbon tetrachloride; ethers such as 1,4-dioxane, THF and DME; and water. These solvents can be used alone or in combination.

This reaction can be carried out in the presence of a catalyst. Examples of such a catalyst are Lewis acids such as zinc chloride, aluminum chloride, and tin (IV) chloride: and mineral acids such as sulfuric acid and phosphoric acid.

The reaction can be usually performed at temperatures in the range of 0° C. to 150° C.

The 4-fluorobiphenyl derivative of formula (VI-d), which is a 4-fluorobiphenyl derivative of formula (VI), in which $X^2$ is a formyl group, can also be produced by oxidizing the 4-fluorobiphenyl derivative of formula (VI-e) having the halogenomethyl group, which is obtained by the above-mentioned halogenomethylation reaction.

This oxidation reaction can be carried out by use of a reagent which comprises, for instance, a base and DMSO in combination, as an oxidizing agent.

Examples of the above-mentioned base are alkali metal carbonates such as sodium hydrogencarbonate and potassium hydrogencarbonate; and organic bases such as triethylamine and diethylisopropylamine.

It is preferable that this oxidation reaction be carried out in a solvent. Examples of a solvent for use in this oxidation reaction are ethers such as diethyl ether, DME, THF, and 1,4-dioxane; and aromatic hydrocarbons such as benzene, toluene and xylene.

This oxidation reaction can be usually carried out at temperatures in the range of 0° C. to 150° C.

Alternatively, Sommelet reaction using tetramethylhexamine, Hass reaction using a sodium salt of a nitroalkane such as 2-nitropropane, and other oxidation reactions can also be employed for the conversion of the halogenomethyl group in the 4-fluorobiphenyl derivative of formula (IV-e) to the formyl group.

Furthermore, the following 4-fluorobiphenyl derivative of formula (VI-f), which is the 4-fluorobiphenyl derivative of formula (VI), in which $X^2$ is a hydroxymethyl group,

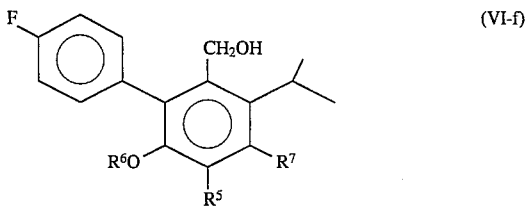

wherein $R^5$, $R^6$, and $R^7$ are respectively as defined previously, can be produced by subjecting the previously mentioned 4-fluorobiphenyl derivative of formula (VI-b) to a hydroxymethylation reaction.

This hydroxymethylation reaction can be carried out by allowing the 4-fluorobiphenyl derivative of formula (VI-b) to react with formaldehyde, paraformaldehyde, trioxane, dimethoxymethane, halogenomethyl ether or bis(halogenomethyl) ether which is employed in the previously mentioned halogenomethylation reaction, in the presence of an acid catalyst such as a Lewis acid or a mineral acid that is employed in the previously mentioned halogenomethylation reaction.

The previously mentioned 4-fluorobiphenyl derivative of formula (VI-d) having the formyl group can be produced by the previously-mentioned two methods.

Furthermore, the 4-fluorobiphenyl derivative of formula (VI-d) can also be produced by oxidizing the 4-fluorobiphenyl derivative of formula (VI-f).

This oxidation reaction can be carried out by use of an oxidizing agent, for example, a chromium compound such as pyridinium chlorochromate, or pyridinium dichromate; manganese dioxide; DMSO-pyridinium sulfur trioxide; DMSO-oxalyl chloride; and DMSO-acetic anhydride.

Specific examples of the 4-fluorobiphenyl derivative of formula (VI) are as follows:

4'-fluoro-5,6-dimethoxy-3-(propan-2-yl)biphenyl-2-carbaldehyde,
5,6-diethoxy-4'-fluoro-3-(propan-2-yl)biphenyl-2-carbaldehyde,
5,6-dibenzyloxy-4'-fluoro-3-(propan-2-yl)biphenyl-2-carbaldehyde,
4'-fluoro-5,6-methylenedioxy-3-(propan-2-yl)biphenyl-2-carbaldehyde,
4'-fluoro-5,6-(dimethylmethylene)dioxy-3-(propan-2-yl)biphenyl-2-carbaldehyde,
4'-fluoro-5,6-bis(2-methoxyethoxy)-3-(propan-2-yl)biphenyl-2-carbaldehyde,
6-benzyloxy-4'-fluoro-5-methoxy-3-(propan-2-yl)biphenyl-2-carbaldehyde,
4'-fluoro-5-methoxy-6-(2-methoxyethoxy)-3-(propan-2-yl)biphenyl-2-carbaldehyde,
4'-fluoro-5-methoxy-6-[2-(2-methoxyethoxy)ethoxy]-3-(propan-2-yl)biphenyl-2-carbaldehyde,
5-(4'-fluorophenyl)-7-(propan-2-yl)-1,4-benzodioxane-6-carbaldehyde,
6-(4'-fluorophenyl)-2,3-dihydro-7-methoxy-2,2-dimethyl-4-(propan-2-yl)benzo[b]furan-5-carbaldehyde,
7-ethoxy-6-(4'-fluorophenyl)-2,3-dihydro-2,2-dimethyl-4-(propan-2-yl)benzo[b]furan-5-carbaldehyde,
6-(4'-fluorophenyl)-2,3-dihydro-7-(2-methoxyethoxy)-2,2-dimethyl-4-(propan-2-yl)benzo[b]furan-5-carbaldehyde,
7-benzyloxy-6-(4'-fluorophenyl)-2,3-dihydro-2,2-dimethyl-4-(propan-2-yl)benzo[b]furan-5-carbaldehyde,
6-(4'-fluorophenyl)-2,3-dihydro-7-[2-(2-methoxyethoxy)ethoxy]-2,2-dimethyl-4-(propan-2-yl)benzo[b]furan-5-carbaldehyde,
2-chloromethyl-4'-fluoro-5,6-dimethoxy-3-(propan-2-yl)biphenyl,
2-chloromethyl-5,6-diethoxy-4'-fluoro-3-(propen-2-yl)biphenyl,
5,6-dibenzyloxy-2-chloromethyl-4'-fluoro-3-(propan-2-yl)biphenyl,
2-chloromethyl-4'-fluoro-5,6-methylenedioxy-3-(propan-2-yl)biphenyl,
2-chloromethyl-4'-fluoro-5,6-(dimetylmethylene)dioxy-3-(propan-2-yl)biphenyl,
2-chloromethyl-4'-fluoro-5,6-bis(2-methoxyethoxy)-3-(propan-2-yl)biphenyl,
6-benzyloxy-2-chloromethyl-4'-fluoro-5-methoxy-3-(propan-2-yl)biphenyl,
2-chloromethyl-4'-fluoro-5-methoxy-6-(2-methoxyethoxy)-3-(propan-2-yl)biphenyl,
2-chloromethyl-4'-fluoro-5-methoxy-6-[2-(2-methoxyethoxy)ethoxy]-3-(propan-2-yl)biphenyl,
6-chloromethyl-5-(4'-fluorophenyl)-7-(propan-2-yl)-1,4-benzodioxane,
5-chloromethyl-6-(4'-fluorophenyl)-2,3-dihydro-7-methoxy-2,2-dimethyl-4-(propan-2-yl)benzo[b]furan,
5-chloromethyl-7-ethoxy-6-(4'-fluorophenyl)-2,3-dihydro-2,2-dimethyl-4-(propan-2-yl)benzo[b]furan,
5-chloromethyl-6-(4'-fluorophenyl)-2,3-dihydro-7-(2-methoxyethoxy)-2,2-dimethyl-4-(propan-2-yl)benzo[b]furan,
7-benzyloxy-5-chloromethyl-6-(4'-fluorophenyl)-2,3-dihydro-2,2-dimethyl-4-(propan-2-yl)benzo[b]furan,
5-chloromethyl-6-(4'-fluorophenyl)-2,3-dihydro-7-[2-(2-methoxyethoxy)ethoxy]-2,2-dimethyl-4-(propan-2-yl)benzo[b]furan,
4'-fluoro-5,6-dimethoxy-3-(propan-2-yl)biphenyl-2-methanol,
5,6-diethoxy-4'-fluoro-3-(propan-2-yl)biphenyl-2-methanol,
5,6-dibenzyloxy-4'-fluoro-3-(propan-2-yl)biphenyl-2-methanol,
4'-fluoro-5,6-methylenedioxy-3-(propan-2-yl)biphenyl-2-methanol,
4'-fluoro-5,6-(dimethylmethylene)dioxy-3-(propan-2-yl)biphenyl-2-methanol,
4'-fluoro-5,6-bis(2-methoxyethoxy)-3-(propan-2-yl)biphenyl-2-methanol,
6-benzyloxy-4'-fluoro-5-methoxy-3-(propan-2-yl)biphenyl-2-methanol,
4'-fluoro-5-methoxy-6-(2-methoxyethoxy)-3-(propan-2-yl)biphenyl-2-methanol,
4'-fluoro-5-methoxy-6-[2-(2-methoxyethoxy)ethoxy]-3-(propan-2-yl)biphenyl-2-methanol,
5-(4'-fluorophenyl)-7-(propan-2-yl)-1,4-benzodioxane-6-methanol,
6-(4'-fluorophenyl)-2,3-dihydro-7-methoxy-2,2-dimethyl-4-(propan-2-y)benzo[b]furan-5-methanol,
7-ethoxy-6-(4'-fluorophenyl)-2,3-dihydro-2,2'-dimethyl-4-(propan-2-yl)benzo[b]furan-5-methanol,
6-(4'-fluorophenyl)-2,3-dihydro-7-(2-methoxyethoxy)-2,2-dimethyl-4-(propan-2-yl)benzo[b]furan-5-methanol,
7-benzyloxy-6-(4'-fluorophenyl)-2,3-dihydro-2,2-dimethyl-4-(propan-2-yl)benzo[b]furan-5-methanol, and
6-(4'-fluorophenyl)-2,3-dihydro-7-[2-(2-methoxyethoxy)ethoxy]-2,2-dimethyl-4-(propan-2-yl)benzo[b]furan-5-methanol.

REFERENCE EXAMPLE 1

(E)-N-Methoxy-N-methyl-4-phenyl-3-butenamide (Compound (2)):

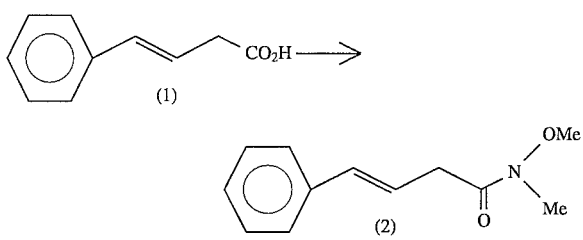

In a stream of nitrogen, 2.70 ml (37.0 mmol) of thionly chloride and one drop of N, N-dimethylformamide (DMF) were added to a solution of 3.00 g (18.5 mmol) of 4-phenyl-3-butenoic acid in 15 ml of dichloromethane at room temperature, and this reaction mixture was refluxed for 50 minutes.

From this reaction mixture, dichloromethane and excessive thionyl chloride were distilled, and 50 ml of 1,2-dichloroethane, 2.00 g (20.5 mmol) of N,O-dimethylhydroxylamine hydrochloride and 3.50 ml (43.3 mmol) of pyridine were successively added to this reaction mixture in a stream of nitrogen at room temperature. This reaction mixture was then stirred for 1.5 hours.

The reaction mixture was then added to a saturated aqueous solution of sodium chloride and the mixture was extracted with ethyl acetate.

The ethyl acetate extract layer was successively washed with 1N hydrochloric acid, a saturated aqueous solution of sodium chloride, an aqueous solution of sodium hydrogencarbonate and a saturated aqueous solution of sodium chloride, dried over magnesium sulfate, and then concentrated.

The residue was chromatographed on silica gel and eluted with a mixed solvent of hexane and ethyl acetate (1:1), whereby (E)-N-methoxy-N-methyl-4-phenyl-3-butenamide (compound (2)) was obtained in the form of a red oil in a yield of 3.32 g (87.5%).

$^1$HNMR (300 MHz, CDCl$_3$) δ3.21 (s, 3H), 3.39 (d, J=6.7 Hz, 2H), 3.73 (s, 3H), 6.37 (dt, J=15.9 and 6.7 Hz, 1H), 6.52 (d, 15.9 Hz, 1H), 7.18–7.42 (m, 5H)ppm.

IR (liquid film): 2972, 2940, 1668 cm$^{-1}$.

Mass (m/z, %): 205 (M$^+$, 32), 149 (55), 144 (35), 117 (100), 115 (38), 91 (25), 69 (24).

Reference Example 2

Ethyl (E)-3,5-dioxo-8-phenyl-7-octenoate (Compound (3)):

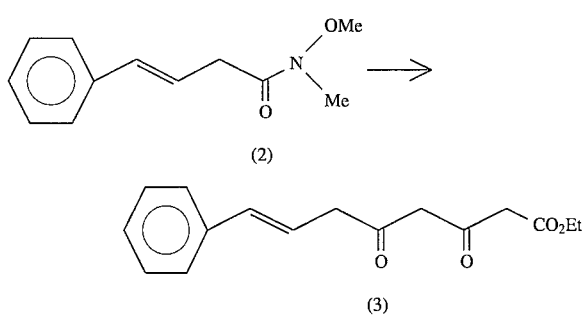

In a stream of argon, 3.21 g (80.3 mmol) of a 60% sodium hydride was suspended in 80 ml of anhydrous tetrahydrofuran (TMF), and 10.8 ml (84.7 mmol) of ethyl acetoacetate was added to this suspension at 0° C., and the mixture was stirred at room temperature for 30 minutes.

This solution was cooled to 0° C., and 52.0 ml of butyllithium (1.66M hexane solution) was added thereto. The mixture was stirred at room temperature for 20 minutes and was then cooled to −78° C., and a solution of 10.9 g (52.9 mmol) of (E)-N-methoxy-N-methyl-4-phenyl-3-butenamide (Compound (2)) synthesized in Reference Example 1 in 50 ml of anhydrous THF was added dropwise over a period of 10 minutes, and the mixture was stirred for 1 hour.

This reaction mixture was then poured into diluted hydrochloric acid. The mixture was extracted with ethyl acetate.

The ethyl acetate extract layer was washed with a saturated aqueous solution of sodium chloride, dried over magnesium sulfate, and then concentrated.

The residue was chromatographed on silica gel and eluted with a mixed solvent of hexane and ethyl acetate (3:1), whereby ethyl (E)-3,5-dioxo-8-phenyl-7-octenoate (Compound (3)) was obtained in the form of a colorless oil in a yield of 9.76 g (67.3%).

$^1$HNMR (300 MHz, CDCl$_3$) Keto:enol 12:88 mixture δ1.27 (t, J=7.1 Hz, 3H), 3.24 (dd, J=7.1 and 1.2 Hz, 1.76H), 3.34 (s, 1.76H), 3.41–3.46 (m, 0.24H), 3.56 (s, 0.24H), 3.81 (s, 0.24H), 4.18 (q, J=7.1 Hz, 0.24H), 4.19 (q, J=7.1 Hz, 1.76H), 5.67 (s, 0.88H), 6.24 (dt, J=15.8 and 7.2 Hz, 0.88H), 6.18–6.32 (m, 0.12H), 6.52 (d, J=15.8 Hz, 1H), 7.20–7.42 (m, 5H)ppm.

IR (liquid film): 2988, 1740, 1600 cm$^{-1}$.

Mass (m/z, %): 274 (M$^+$, 10), 187 (12), 157 (100), 144 (26), 117 (34), 115 (80), 91 (13).

Reference Example 3

Ethyl (E)-3,5-dihydroxy-8-phenyl-7-octenoate (Compound (4)):

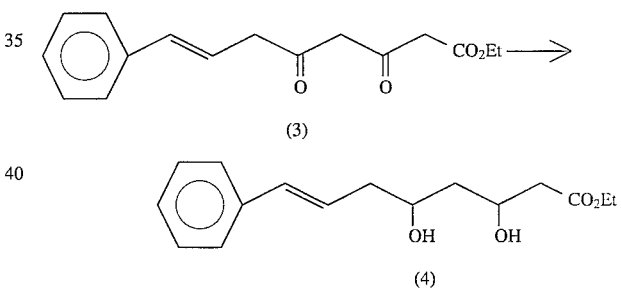

In a stream of argon, 9.48 g (34.6 mmol) of Compound (3) synthesized in Reference Example 2 was added to a mixed solvent of 50 ml of anhydrous THF and 18 ml of methanol. To this solution, 40.0 ml (40.0 mmol) of diethylmethoxyborane (1.0M THF solution) was added at −78° C. by use of a cooling bath. The cooling bath was removed and the reaction mixture was then stirred at room temperature for 30 minutes. The reaction mixture was again cooled to −78° C., and 2.67 g (70.6 mmol) of sodium borohydride was added in three portions to the reaction mixture. The mixture was stirred for 2 hours and 15 minutes.

The reaction mixture was gradually added to 400 ml a 30% aqueous solution of hydrogen peroxide at 0° C. This mixture was then stirred at room temperature overnight.

This reaction mixture was then poured into a saturated aqueous solution of sodium chloride. The mixture was extracted with ethyl acetate.

The ethyl acetate extract layer was successively washed with a saturated aqueous solution of sodium chloride, an aqueous solution of sodium thiosulfate, and a saturated aqueous solution of sodium chloride, dried over magnesium sulfate, and then concentrated.

The residue was chromatographed on silica gel and eluted with a mixed solvent of hexane and ethyl acetate (1:1), whereby ethyl (E)-3,5-dihydroxy-8-phenyl-7-octenoate (Compound (4)) was obtained in a yield of 7.56 g (79.2%).

Melting point: 44.0°–45.0° C. (colorless, fine particles, recrystallized from a mixed solvent of ethyl acetate and hexane)

$^1$HNMR (300 MHz, CDCl$_3$) δ1.27 (t, J=7.2 Hz, 3H), 1.56–1.72 (m, 2H), 2.41 (t with fine coupling, J=6.7 Hz, 2H), 2.38–2.56 (m, 2H), 3.34 (d, J=1.9 Hz, 1H), 3.78 (d, J=2.4 Hz, 1H), 3.97–4.07 (m, 1H), 4.17 (q, J=7.2 Hz, 2H), 4.24–4.35 (m, 1H), 6.23 (dt, J=15.8 and 7.3 Hz, 1H), 6.47 (d, J=15.8 Hz, 1H), 7.18–7.39 (m, 5H) ppm.

IR (KBr): 3456, 2952, 1724, 1598 cm$^{-1}$.

Mass (FAB-positive, m/z, %): 279 ([H+H]$^+$, 100)

Mass (m/z, %): 242 (M$^+$-36, 37), 143 (59), 118 (35), 117 (76), 115 (73), 97 (100), 91 (33), 73 (37).

Reference Example 4

Ethyl (E)-8-phenyl-3,5-O-isopropyliden-3,5-dihydroxy-7-octenoate (Compound (5)):

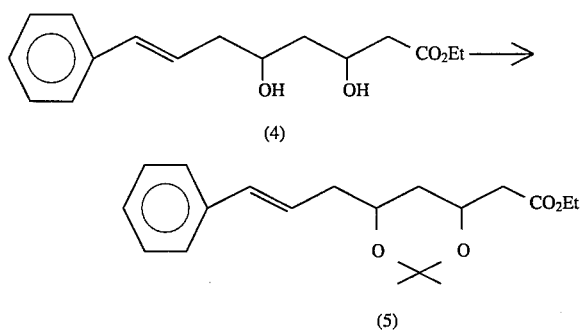

In a stream of argon, 2.00 g (7.19 mmol.) of Compound (4) synthesized in Reference Example 3 was dissolved In 7.0 ml of 2,2-dimethoxypropane at room temperature. To this solution, 18 mg (0.09 mmol) of p-toluenesulfonic acid monohydrate was added, and the mixture was stirred for 2 hours.

This reaction mixture was then poured into an aqueous solution of sodium hydrogencarbonate. This mixture was extracted with ethyl acetate.

The ethyl acetate extract layer was washed with a saturated aqueous solution of sodium chloride, dried over magnesium sulfate, and then concentrated.

The residue was chromatographed on silica gel and eluted with a mixed solvent of hexane and ethyl acetate (3:1), whereby ethyl (E)-8-phenyl-3,5-O-isopropylidene- 3,5-dihydroxy-7-octenoate (Compound (5)) was obtained in the form of a colorless oil in a yield of 2.18 g (95.4%).

$^1$HNMR (300 MHz, CDCl$_3$) δ1.25 (t, J=7.1 Hz, 3H), 1.17–1.31 (m, 1M), 1.40 (s, 3H), 1.4 (s, 3H), 1.64 (dt, J=12.8 and 2.5 Hz, 1H), 2.25–2.53 (m, 2H), 2.37 (dd, J=15.4 and 6.1 Hz,1H), 2.53 (dd, J=15.4 and 7.0 Hz, 1H), 3.98 (dtd, J=11.4, 6.2 and 2.5 Hz, 1H), 4.06–4.22 (m, 2H), 4.26–4.37 (m, 1H), 6.20 (dt, J=15.9 and 7.1 Hz, 1H), 6.44 (d, J=15.9 Hz, 1H), 7.16–7.40 (m, 5H)ppm.

IR (liquid film): 2992, 2944, 1740, 1600 cm$^{-1}$.

Mass (FAB-positive, m/z, %); 319 ([M+H]$^+$,6).

Mass (m/z, %): 303 (M$^+$-15, 26), 201 (75), 183 (34), 155 (39), 143 (100), 129 (38), 115 (49), 97 (56).

Reference Example 5

Ethyl 7-oxo-3,5-O-isopropyliden-3,5-dihydroxyheptenoate (Compound (6)):

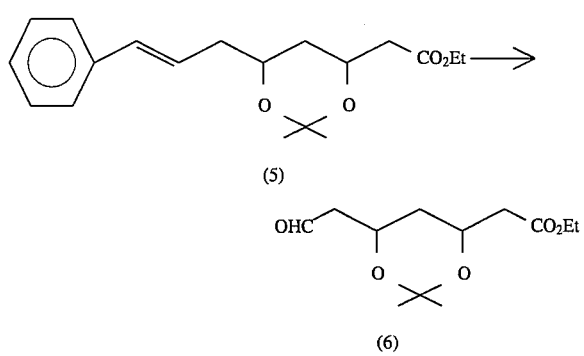

1.50 g (4.72 mmol) of Compound (5) synthesized in Reference Example 4 was added to 100 ml of dichloromethane. Ozone was passed through this solution at −78° C. for 1 hour. Excessive ozone was then removed from this reaction mixture by purging it with argon until the bluish reaction mixture became colorless.

To this reaction mixture, 1.50 g (5.72 mmol) of triphenylphosphine was added, and the reaction mixture was stirred at −78° C. for 30 minutes, and then at room temperature for 1 hour.

This reaction mixture was concentrated, and the residue was chromatographed on silica gel and eluted with a mixed solvent of hexane and ethyl acetate (2:1), whereby ethyl 7-oxo-3,5-O-isopropylidene-3,5-dihydroxyheptanoate (Compound (6)) was obtained in the form of a colorless oil in a yield of 1.10 g (95.4%).

$^1$HNMR (300 MHz, CDCl$_3$) δ1.27 (t, J=7.1 Hz, 3H), 1.22–1.35 (m, 1H), 1.37 (s, 3H), 1.50 (s, 3H), 1.69 (dt, J=12.7 and 2.5 Hz, 1H), 2.39 (dd, J=15.5 and 6.1 Hz, 1H), 2.49 (ddd, J=16.6, 5.0 and 1.6 Hz, 1H), 2.55 (dd, J=15.5 and 7.1 Hz, 1H), 2.63 (ddd, J=16.6, 7.3 and 2.3 Hz, 1H), 4.08–4.25 (m, 2H), 4.32–4.51 (m, 2H), 9.79 (dd, J=2.3 and 1.6 Hz, 1H)ppm.

IR (liquid film): 2996, 1734 cm$^{-1}$.

Mass (FAB-positive, m/z, %): 245 ([M+H]$^+$, 82).

Mass (m/s, %): 229 (M$^+$-15, 100), 201 (19).

Reference Example 6

1-(4-fluorophenyl)-4-methyl-1-penten-3-one (Compound (9)):

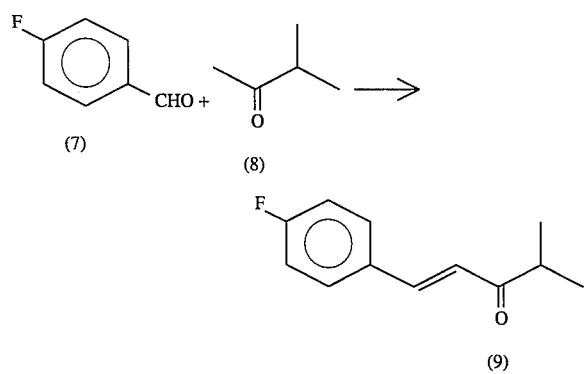

50.0 ml (466 mmol) of 3-methyl-2-butanone (Compound (8)) was added to a mixed solution of 130 ml of ethanol, 100 ml of water and 7.78 ml (15.5 mmol) of a 2N aqueous solution of sodium hydroxide. To this mixture, 33.3 ml (311 mmol) of 4-fluorobenzaldehyde (Compound (7)) was added at 0° C. This mixture was stirred in an atmosphere of argon at room temperature overnight.

This reaction mixture was poured into diluted hydrochloric acid, and the mixture was extracted with ethyl acetate.

The ethyl acetate extract layer was successively washed with water and a saturated aqueous solution of sodium chloride, dried over magnesium sulfate, and then concentrated, whereby 50.4 g crude 1-(4-fluorophenyl)-4-methyl-1-penten-3-one (Compound (9)) was obtained in the form of a pale yellow oil in a yield of 50.4 g (90.1%).

$^1$HNMR (300 MHz, CDCl$_3$) δ1.18 (d, J=6.9 Hz, 6H ), 2.92 (hept, J=6.9 Hz, 1H ), 7.75 (d with fine coupling, J=16.0 Hz, 1H), 7.04–7.13 (m, 2H), 7,51–7.62 (m, 3H)ppm.

IR (liquid film): 2976, 2936, 1692, 1666, 1616, 1600 cm$^{-1}$.

Mass (m/z, %): 192 (M$^+$, 13), 149 (100), 121 (21), 101 (16).

Reference Example 7

6-acetyl-5-(4-fluorophenyl)-3-(propan-2-yl)-2-cyclohexene-1-one (Compound (11)):

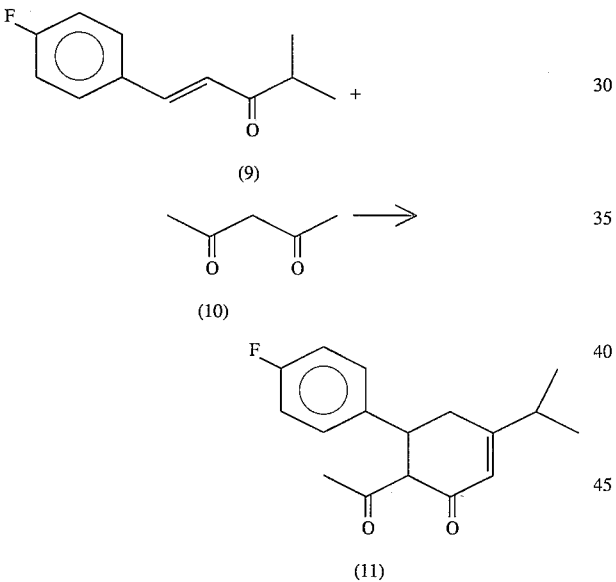

4.11 ml (40.0 mmol) of 2,4-pentanedione (Compound (10)) was added to 20 ml of toluene, and 0.60 ml (4.0 mmol) of DBU was then added, and the mixture was stirred. To this solution, 3.84 g (20.0 mmol) of 1-(4-fluorophenyl)-4-methyl-1-penten-3-one (Compound (9)) synthesized in Reference Example 6 was added, and the mixture was stirred in an atmosphere of argon at room temperature for 2 days.

The reaction mixture was poured into 1N hydrochloric acid. The mixture was extracted with ethyl acetate.

The extract layer was successively washed with water and then with a saturated aqueous solution of sodium chloride, dried over magnesium sulfate, and then concentrated.

The residue was crystallized from a mixed solvent of ethyl acetate and hexane.

The filtrate obtained in the crystallization was concentrated, chromatographed on silica gel, eluted with a mixed solvent of ethyl acetate and hexane (1:3), and crystallized from a mixed solvent of ethyl acetate and hexane.

Thus, a crystalline product was obtained in an amount of 4.31 g in total.

3.98 g of the crystalline product was dissolved in 25 ml of toluene, and 2 ml of phosphoric acid (85%) was added thereto. This mixture was refluxed in an atmosphere of argon for 3 hours. The reaction mixture was then poured into a saturated aqueous solution of sodium hydrogencarbonate. The mixture was extracted with ethyl acetate. The ethyl acetate exact layer was successively washed with a saturated aqueous solution of sodium hydrogencarbonate, water, and a saturated aqueous solution of sodium chloride, dried over magnesium sulfate, and then concentrated. The residue was chromatographed on silica gel and eluted with a mixed solvent of ethyl acetate and hexane (1:4), whereby 6-acetyl-5-(4-fluorophenyl)-3-(propan-2-yl)-2-cyclohexene-1-one (Compound (11)) was obtained in the form of a pale yellow oil in a yield of 2.44 g.

$^1$HNMR (300 MHz, CDCl$_3$) Keto:enol 1:9 mixture δ0.84 (d, J=6.8 Hz, 2.7H), 0.87 (d, J=6.8 Hz, 2.7H), 1.12 (d, J=6.8 Hz, 0.6H), 1.93 (s, 2.7H), 2.10 (s, 0.3H), 2.22 (hept, J=6.8 Hz, 0.9H), 2.38 (dd, J=17.0 and 1.7 Hz, 0.9H), 2.41–2.51 (m, 0.1H), 2.51 (ddd, J=18.0, 10.0 and 2.0 Hz, 0.1H), 2.61 (dd, J=18.0 and 5.1 Hz, 0.1H), 2.88 (ddd, J=17.0, 8.0 and 2.7 Hz, 0.9H), 3.66 (ddd, J=12.1, 10.0 and 5.1 Hz, 0.1H), 3.77 (d, J=12.1 Hz, 0.1H), 3.97 (d with fine coupling, J=8.0 Hz, 0.9 Hz), 5.94 (dd, J=2.7 and 1.0 Hz, 0.9H), 5.99 (s with fine coupling, 0.1H), 6.90–7.05 (m, 2H), 7.09–7.24 (m, 2H)ppm.

IR (liquid film): 2936, 1722, 1660, 1630, 1606 cm$^{-1}$.

Mass (m/z, %): 274 (M$^+$, 55), 231 (100), 189 (38), 43 (34).

Reference Example 8

6-(4-fluorophenyl)-2-hydroxy-4-(propan-2-yl)acetophenone (Compound (12)):

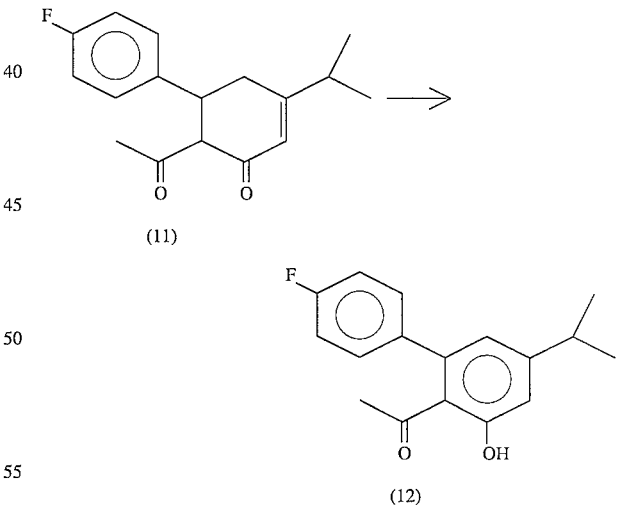

1.78 g (6.50 mmol) of 6-acetyl-5-(4-fluorophenyl)-3-(propan-2-yl)-2-cyclohexene-1-one (Compound (11)) synthesized in Reference Example 7 was dissolved in 15 ml of diethylene glycol dimethyl ether. To this solution, 0.97 ml (6.50 mmol) of isophorone and 356 mg of 10% Pd—C were successively added. This reaction mixture was then refluxed, with a nitrogen gas being bubbled therethrough, for 30 minutes.

The reaction mixture was diluted with ethyl acetate, and faltered through Celite, and concentrated.

Diethylene glycol dimethyl ether was removed by distillation under reduced pressure from the reaction mixture, and the residue was chromatographed on silica gel and eluted with a mixed solvent of ethyl acetate and hexane (1:10), whereby 6-(4-fluorophenyl)-2-hydroxy-4 -(propan-2-yl)acetophenone (Compound (12)) was obtained in a yield of 1.25 g (70.7%).

Melting point 52.5°–53.5° C. (colorless columns, recrystallized from hexane)

$^1$HNMR (300 MHz, CDCl$_3$) δ1.26 (d, J=6.9 Hz, 6H), 1.84 (s, 3H), 2.89 (hept, J=6.9 Hz, 1H), 6.65 (d, J=1.7 Hz, 1H), 6.87 (d, J=1.7 Hz, 1H), 7.09–7.18 (m, 2H), 7.27–7.36 (m, 2H), 11.91 (s, 1H)ppm.

IR (KBr): 2964, 2876, 1630, 1608 cm$^{-1}$.

Mass (m/z, %): 272 (M$^+$, 82), 257 (100), 229 (26), 215 (36), 183 (13), 149 (18), 43 (16).

EXAMPLE 1

4'-fluoro-5-(propan-2-yl)biphenyl-2,3-diol (Compound (13)):

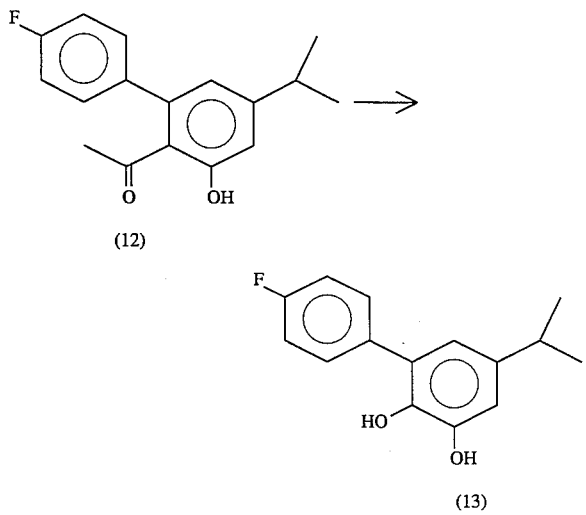

973 mg (3.58 mmol) of 6-(4-fluorophenyl)-2-hydroxy-4-(propan-2-yl)acetophenone (Compound (12)) synthesized in Reference Example 8 was dissolved in 5 ml of THF. In an atmosphere of argon, to this solution, 10.7 ml (10.7 mmol) of 1N sodium hydroxide and 2.03 ml (17.9 mmol) of a 30% aqueous solution of hydrogen peroxide were added at 0° C. This reaction mixture was stirred for 2 hours and 45 minutes.

The reaction mixture was then poured into a saturated aqueous solution of ammonium chloride, and the mixture was extracted with ethyl acetate to obtain a first ethyl acetate extract layer. The pH of the water layer was adjusted to pHI by adding 1N hydrochloric acid, and the water layer was extracted with ethyl acetate to obtain a second ethyl acetate extract layer. Both ethyl acetate extract layers were combined, and the combined extract layer was successively washed with water, a saturated aqueous solution of sodium thiosulfate, water and a saturated aqueous solution of sodium chloride, dried over magnesium sulfate, and concentrated.

The residue was crystallized from a mixed solvent of ethyl acetate and hexane, whereby 4'-fluoro-5-(propan-2 -yl)biphenyl-2,3-diol (Compound (13)) was obtained in a yield of 523 mg (59.4%).

The filtrate was concentrated, chromatographed on silica gel, and eluted with a mixed solvent of ethyl acetate and hexane (1:3), whereby 4'-fluoro-5-(propan- 2-yl)biphenyl-2, 3-diol (Compound (13)) was further obtained in a yield of 227 mg (25.8%).

Melting point: 106.0°–107.0° C. (colorless columns, recrystallized from a mixed solvent of ethyl acetate and hexane)

$^1$HNMR (300 MHz, CDCl$_3$) δ1.23 (d, J=6.9 Hz, 6H), 2.83 (hept, J=6.9 Hz, 1H), 5.04 (broad s, 1H), 5.31 (broad s, 1H), 6.66 (d, J=2.1H, 1H), 6.80 (d, J=2.1 Hz, 1H), 7.12–7.21 (m, 2H), 7.44–7.53 (m, 2H)ppm.

IR (KBr): 3496, 3368, 2964, 2872, 1606 cm$^{-1}$.

Mass (m/z, %): 246 (M$^+$, 57), 231 (100), 149 (23), 57 (10).

EXAMPLE 2

4'-fluoro-2,3-dimethoxy-5-(propan-2-yl)biphenyl (Compound (14)):

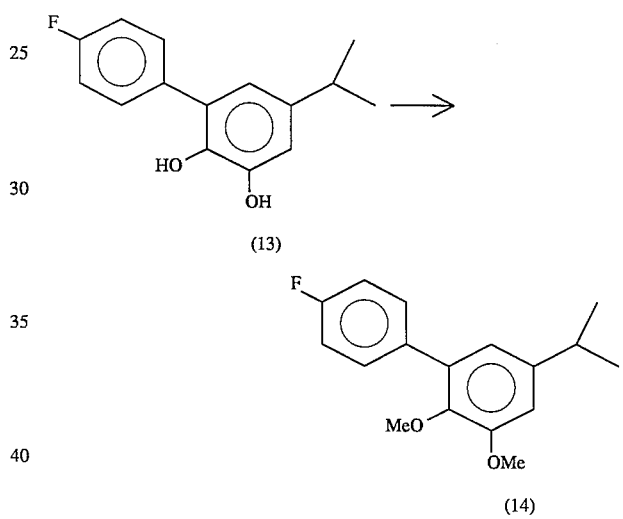

695 mg (2.83 mmol) of 4'-fluoro-5-(propan-2 -yl)biphenyl-2,3-diol (Compound (13)) synthesized in Example 1 was dissolved in 7 ml of DMF, and 0.71 ml (11.3 mmol) of methyl iodide and 1.56 g (11.3 mmol) of potassium carbonate were added thereto. This reaction mixture was stirred in an atmosphere of argon for 3 hours.

The reaction mixture was then poured into water, and the mixture was extracted with ethyl acetate. The extract layer was washed with a saturated aqueous solution of sodium chloride, dried over magnesium sulfate, and concentrated. The residue was chromatographed on silica gel, and eluted with a mixed solvent of ethyl acetate and hexane (1:6), whereby 4'-fluoro-2,3-dimethoxy-5-(propan-2-yl)biphenyl (Compound (14)) was obtained in a yield of 746 mg (96.2%).

Melting point: 59.0°–60.0° C. (colorless fine particles, recrystallized from hexane)

$^1$HNMR (300 MHz, CDCl$_3$) δ1.27 (d, J=6.9 Hz, 6H), 2.90 (hept, J=6.9 Hz, 1H ), 3.55 (s, 3H), 3.91 (s, 3H), 6.76 (d, J=2.1 Hz, 1H), 6.77 (d, J=2.1 Hz, 1H), 7.06–7.15 (m, 2H), 7.49–7.57 (m, 2H)ppm.

IR 2964, 2880, 1600, 1580 cm$^{-1}$.

Mass (m/z, %) 274 (M$^+$, 98), 259 (100), 217 (20), 202 (14), 149 (34), 57 (17).

EXAMPLE 3

2-Bromo-4'-fluoro-5,6-dimethoxy-3-(propan-2-yl)biphenyl (Compound (15)):

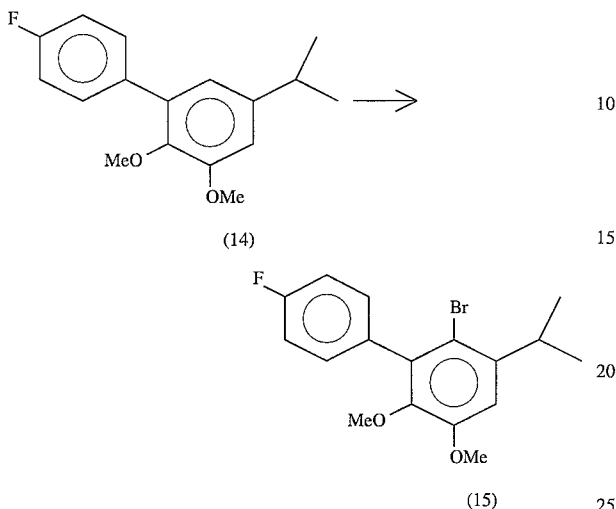

30.1 g (110 mmol) of 4'-fluoro-2,3-dimethoxy-5 -(propan-2-yl)biphenyl (Compound (14)) synthesized in Example 2 was dissolved in a mixed solvent of 300 ml of THF and 30 ml of water. To this solution, 20.5 g (115 mmol) of N-bromosuccinimide was added at 0° C. This reaction mixture was stirred in an atmosphere of argon at room temperature for 2 hour and 45 minutes.

The reaction mixture was poured into water, and the mixture was extracted with ethyl acetate. The extract layer was successively washed with a saturated aqueous solution of sodium thiosulfate, water, and a saturated aqueous solution of sodium chloride, dried over magnesium sulfate, and concentrated. The residue was crystallized from a mixed solvent of ethyl acetate and hexane, whereby 2-bromo-4'-fluoro-5,6-dimethoxy-3-(propan-2-yl)biphenyl (Compound (15)) was obtained in a yield of 37.0 g (95.7%).

The filtrate obtained in the above crystallization was concentrated, chromatographed on silica gel, and eluted with a mixed solvent of dichloromethane and hexene (1:1), whereby Compound (15) was further obtained in a yield of 1.15 g (3.0%).

Melting points: 127.0°–127.5° C. (colorless fine particles, recrystallized from hexane)

$^1$HNMR (300 MHz, CDCl$_3$) δ1.27 (d, J=6.8 Hz, 6H), 3.45 (hept, J=6.8 Hz, 1H), 3.50 (8, 3H), 3.91 (s, 3H), 6.89 (s, 1H), 7.08– 7.16 (m, 2H), 7.20–7.29 (m, 2H)ppm.

IR (KBr): 2972, 2936, 1604, 1580 cm$^{-1}$.

Mass (m/z, %): 354 (M$^+$, 99), 352 (M$^+$, 100), 339 (81), 337 (82), 324 (23), 322 (24), 243 (28), 149 (26), 69 (17).

EXAMPLE 4

Ethyl 7-[4'-fluoro-5,6-dimethoxy-3-(propan-2-yl)-biphenyl-2-yl]-3,5-O-isopropyliden-3,5,7-trihydroxyheptanoate (Compound (16):

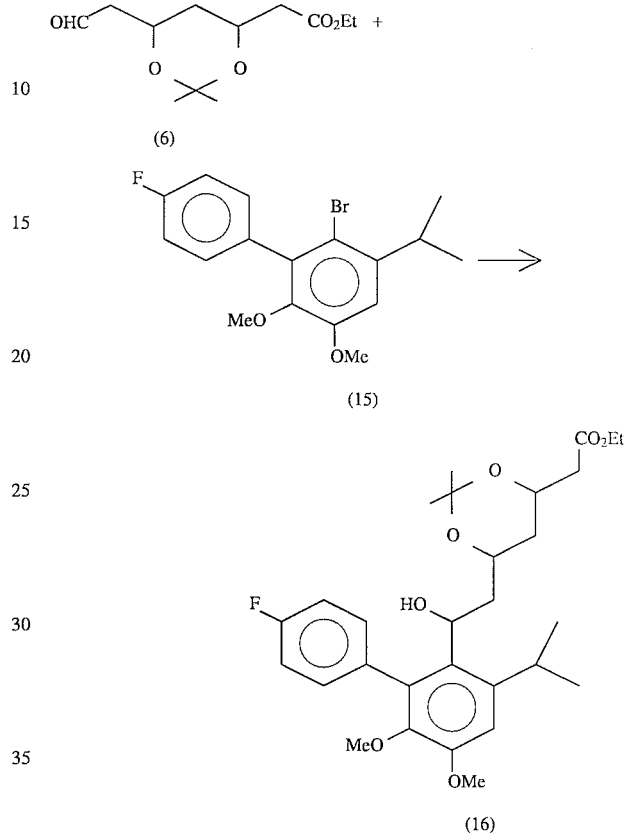

In an atmosphere of argon, 750 mg (2.11 mmol) of 2-bromo-4'-fluoro-5,6-dimethoxy-3-(propan-2-yl)biphenyl (Compound (15)) synthesized in Example 3 and 207 mg (8.52 mmol) of magnesium turnings were added to 4 ml of anhydrous THF, and the mixture was refluxed. To this mixture, a solution of 0.27 ml (2.10 mmol) of 1,2 -diboromoethane in 4 ml of anhydrous THF was added dropwise over a period of 10 minutes, and the mixture was refluxed for 1 hour.

To this solution, a solution of 620 mg (2.54 mmol) of ethyl 7-oxo-3,5-O-isopropylidene-3,5-dihydroxyheptanoate Compound (6) synthesized in Reference Example 5 in 2 ml of anhydrous THF was added, and the mixture was stirred at room temperature for 1 hour.

This reaction mixture was poured into a saturated aqueous solution of ammonium chloride. The mixture was then extracted with ethyl acetate. The ethyl acetate extract layer was washed with a saturated aqueous solution of sodium chloride, dried over magnesium sulfate, and concentrated.

The residue was chromatographed on silica gel and eluted with a mixed solvent of hexane and ethyl acetate (2:1), whereby ethyl 7-[4'-fluoro-5,6-dimethoxy-3 -(propan-2-yl)-biphenyl-2-yl]-3,5-O-isopropylidene-3,5,7 -trihydroxyheptanoate (Compound (16)) was obtained in the form of a colorless amorphous solid in a yield of 694 mg (63.3%).

Mixture of 1:1 stereoisomers $^1$HNMR (300 MHz, CDCl$_3$) δ0.97 (dd, J=24.3 and 11.8 Hz, 0.5H), 1.10 (dd, J=24.3 and 11.8 Hz, 0.5H), 1.22–1.31 (m, 15H), 1.37–1.44 (m, 0.5H), 1.48–1.60 (m, 0.5H), 2.04–2.54 (m, 4H), 2.87 (broad s, 0.5H), 3.46 (s, 1.5H), 3.47 (s, 1.5H), 3.75–3.92 (m, 1H), 3.89 (s, 3H), 3.98–4.28 (m, 4H), 4.68–4.75 (m, 0.5H), 4.87–4.94 (m, 0.5H), 6.91 (s, 1H), 7.00–7.30 (m, 4H)ppm.

IR (KBr): 3532, 2992, 2956, 1738, 1590 cm$^{-1}$.

Mass (m/z, %): 518 (M$^+$, 20), 442 (100), 424 (85), 327 (91), 285 (77), 283 (81), 183 (20), 43 (37).

EXAMPLE 5

Ethyl (E)-7-[4'-fluoro-5,6-dimethoxy-3-(propan-2-yl)biphenyl-2-yl]-3,5-O-isopropylidene-3,5-dihydroxy-6-heptenoate (Compound (17)):

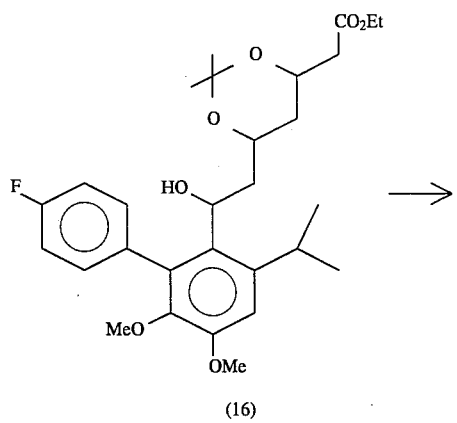

(16)

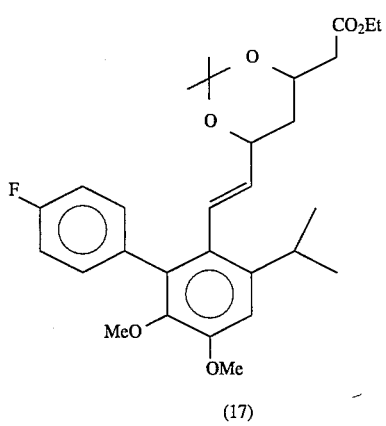

(17)

225 mg (0.43 mmol) of Compound (16) synthesized in Example 4 was dissolved in 4 ml of 1,2-dichloroethane. To this solution, 0.11 ml (1.30 mmol) of anhydrous pyridine and then 0.04 ml (0.49 mmol) of thionyl chloride were added, and the mixture was stirred in an atmosphere of argon for 50 minutes.

This reaction mixture was poured into water, and the mixture was then extracted with ethyl acetate.

The ethyl acetate extract layer was washed with an aqueous solution of sodium hydrogencarbonate and a saturated aqueous solution of sodium chloride, dried over magnesium sulfate, and then concentrated.

The residue was dissolved in 5 ml of 1,2-dichloroethane, and to this solution, 0.10 ml (1.24 mmol) of anhydrous pyridine was added, and the mixture was refluxed in an atmosphere of argon for 5 hours.

This reaction mixture was poured into water, and the mixture was extracted with ethyl acetate. The ethyl acetate extract layer was successively washed with a saturated aqueous solution of sodium chloride, an aqueous solution of sodium hydrogencarbonate, and a saturated aqueous solution of sodium chloride, dried over magnesium sulfate, and concentrated.

The residue was crystallized from a mixed solvent of ethyl acetate and hexane, whereby ethyl (E)-7-[4'-fluoro-5,6-dimethoxy-3-(propan-2-yl)biphenyl-2-yl]-3,5-O-isopropylidene- 3,5-dihydroxy-6-heptenoate (compound (17)) was obtained in a yield of 129 mg (59.4%).

The filtrate was concentrated and the residue was chromatographed on silica gel and eluted with a mixed solvent of ethyl acetate and hexane (1:4), whereby Compound (17) was obtained in a yield of 42 mg (19.4%).

Melting point: 120.0°–121.0° C. (colorless needles, recrystallized from a mixed solvent of ethyl acetate and hexane)

$^1$HNMR (300 MHz, CDCl$_3$) δ0.88 (dd, J=24.5 and 11.7 Hz, 1H), 1.20–1.30 (m, 1H), 1.23 (d, J=6.8 Hz, 6H), 1.27 (t, J=7.2 Hz, 3H), 1.34 (s, 3H), 1.43 (s, 3H), 2.30 (dd, J=15.5 and 6.2 Hz, 1H), 2.49 (dd, J=15.5 and 7.0 Hz, 1H), 3.25 (hept, J=6.8 Hz, 1H), 3.47 (s, 3H), 3.91 (s, 3H), 4.09–4.30 (m, 4H), 5.13 (dd, J=16.2 and 6.2 Hz, 1H), 6.22 (dd, J=16.2 and 0.9 Hz, 1H), 6.85 (s, 1H), 6.98–7.07 (m, 2H), 7.10–7.20 (m, 1H)ppm.

IR (KBr); 2964, 2944, 1738, 1602 cm$^{-1}$.

Mass (m/z, %): 500 (M$^+$, 13), 442 (71), 424 (100), 381 (36), 327 (74), 285 (76), 283 (95), 183 (24), 43 (45).

Reference Example 9

Ethyl (E)-7-[4'-fluoro-5,6-dimethoxy-3-(propan-2-yl)biphenyl-2-yl]-3,5-dihydroxy-6-heptenoate (Compound (18)):

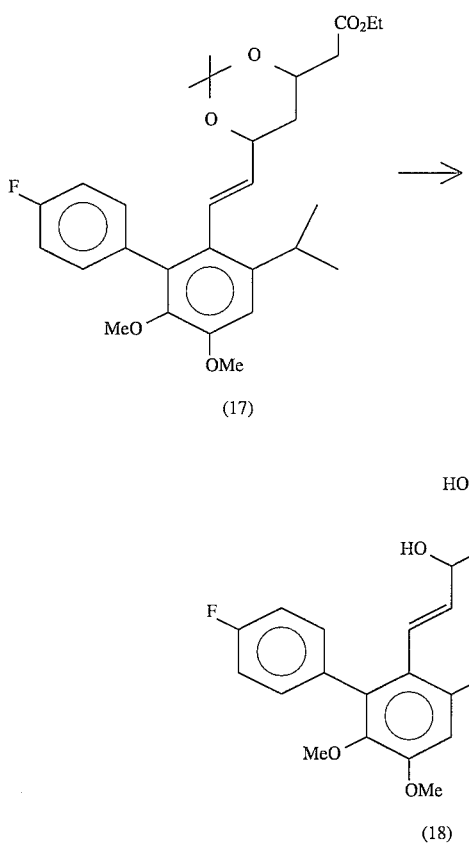

51 mg (0.10 mmol) of Compound (17) synthesized in Example 5 was dissolved in a mixed solvent of 2 ml of THF and 1 ml of water. To this solution, 18 mg (0.10 mmol) of p-toluenesulfonic acid monohydrate was added, and the mixture was stirred in an atmosphere of argon at room temperature for 4 days.

The reaction mixture was poured into water, and the mixture was then extracted with ethyl acetate. The ethyl acetate extract layer was successively washed with water, a saturated aqueous solution of sodium hydrogencarbonate, and a saturated aqueous solution of sodium chloride, dried over magnesium sulfate, and concentrated.

The residue was chromatographed on silica gel and eluted with a mixed solvent of ethyl acetate and hexane (1:1), whereby ethyl (E)-7-[4'-fluoro-5,6-dimethoxy-3-(propan-2-yl)biphenyl-2-yl]-3,5-dihydroxy-6-heptenoate (compound (18)) was obtained in a yield of 34 mg (72.5%).

Melting 77.0°–78.5° C. (colorless needles, recrystallized from a mixed solvent of ethyl acetate and hexane)

$^1$HNMR (300 MHz, CDCl$_3$) δ1.22 (d, J=6.8 Hz, 3H), 1.23 (d, J=6.8 Hz, 3H), 1.15–1.30 (m, 1H), 1.29 (t, J=7.2 Hz, 3M), 1.34–1.49 (m, 1H), 2.32–2.48 (m, 2H), 2.75–2.79 (m, 1H), 3.22 (hept, J=6.8 Hz, 1H), 3.48 (s, 3H), 3.58 (s with fine coupling, 1H), 3.91 (s, 3H), 4.00–4.12 (m, 1H), 4.18 (q, J=7.2 Hz, 2H), 4.22–4.34 (m, 1H), 5.16 (dd, J=16.1 and 6.5 Hz, 1H), 6.34 (dd, J=16.1 and 1.1 Hz, 1H), 6.86 (s, 1H), 7.00–7.09 (m, 2H), 7.10–7.20 (m, 2H)ppm.

IR (KBr): 3435, 1724 cm$^{-1}$.

Mass (m/z, %), 460 (M$^+$, 100), 442 (88), 327 (51), 285 (56), 273 (65), 243 (28), 183 (17).

Reference Example 10

Sodium (E)-7-[4'-fluoro-5,6-dimethoxy-3-(propan-2-yl)biphenyl-2-yl]-3,5-dihydroxy-6-heptenoate (Compound (19)):

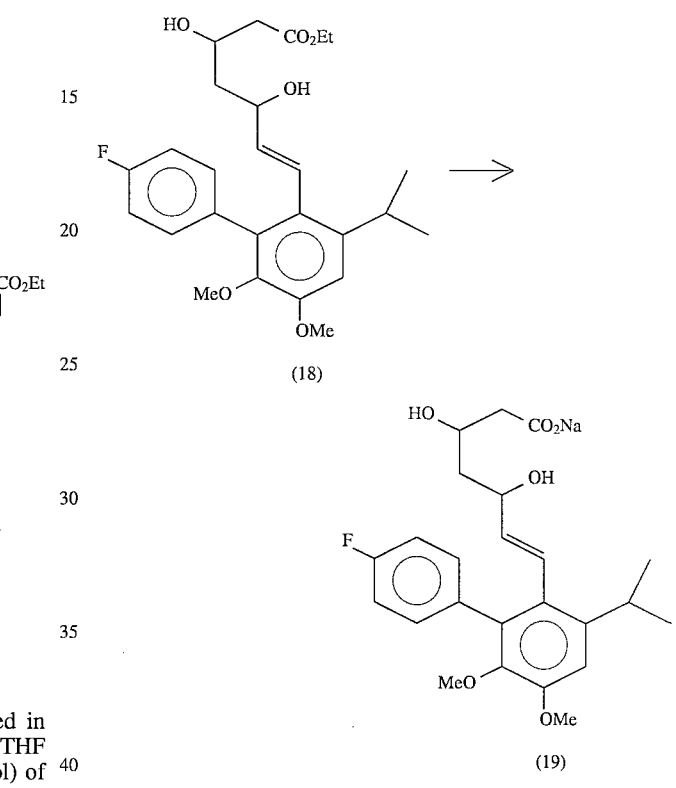

122 mg (0.265 mmol) of Compound (18) synthesized in Reference Example 9 was dissolved in 3 ml of ethanol. To this solution, 0.530 ml (0.265 mmol) of a 0.5N aqueous solution of sodium hydroxide was added, and the mixture was stirred in an atmosphere of argon at room temperature for 1 hour and 25 minutes.

The reaction mixture was concentrated, and the residue was dissolved in water and then subjected to freeze-drying, whereby sodium (E)-7-[4'-fluoro-5,6-dimethoxy-3-(propan-2-yl)biphenyl-2-yl]-3,5-dihydroxy-6-heptenoate (compound (19)) was obtained in the form of a colorless amorphous solid in a yield of 117 mg (97.2%).

$^1$HNMR (300 MHz, CDCl$_3$) δ1.24 (d, J=6.8 Hz, 6H), 1.20–1.31 (m, 1H), 1.45–1.57 (m, 1H), 2.16 [dd, J=15.4 and 7.9 Hz, 1H), 2.28 (dd, J=15.4 and 4.5 Hz, 1H), 3.35 (hept, J=6.8 Hz, 1H), 3.45 (s, 3H), 3.71–3.82 (m, 1H), 3.89 (s, 3H), 4.12–4.22 (m, 1H), 5.21 (dd, J=16.1 and 6.7 Hz, 1H), 6.29 (dd, J=16.1 and 1.1 Hz, 1H), 6.95 (s, 1H), 7.04–7.20 (m, 4H)ppm.

IR (KBr): 3456, 2968, 1574 cm$^{-1}$.

Mass (FAB-negative, m/z, %): 453 ([M–H]$^-$, 7), 431 (100).

Reference Example 11

Ethyl (E)-8-phenyl-3,5-O-cyclohexylidene-3,5-dihydroxy-7-octenoate (Compound (20)):

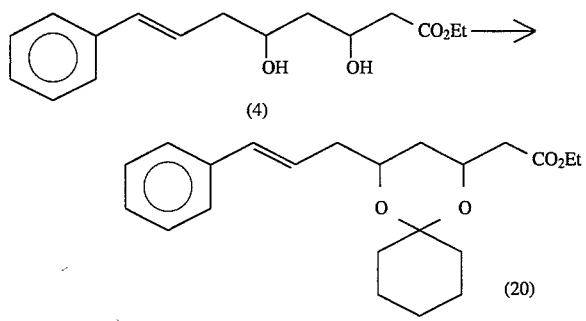

In an atmosphere of argon, 1.09 g (3.92 mmol) of Compound (4) synthesized in Reference Example 3 was dissolved in 3 ml of cyclohexanone dimethylacetal, and the mixture was stirred at room temperature. To this reaction mixture, 35 mg (0.18 mmol) of p-toluenesulfonic acid monohydrate was added, and the mixture was stirred for 4 hours and 25 minutes.

This reaction mixture was poured into water, and the mixture was then extracted with ethyl acetate. The ethyl acetate extract layer was successively washed with an aqueous solution of sodium hydrogencarbonate, water, and a saturated aqueous solution of sodium chloride, dried over magnesium sulfate, and concentrated.

The residue was chromatographed on silica gel and eluted with a mixed solvent of hexene and ethyl acetate (6:1). The eluant was concentrated and the residue was again chromatographed on silica gel, and then eluted with a mixed solvent of hexane and ethyl acetate (10:1), whereby ethyl (E)-8-phenyl-3,5-O-cyclohexylidene-3,5 -dihydroxy-7-octenoate (compound (20)) was obtained in the form of a colorless oil in a yield of 1.14 g (81.2%).

$^1$HNMR (300 MHz, CDCl$_3$) δ1.18–1.32 (m, 1H), 1.26 (t, J=7.1 Hz, 3H), 1.32–1.50 (m, 4H), 1.50–1.67 (m, 5H), 1.72–1.86 (m, 1H), 1.94–2.08 (m, 1H), 2.25–2.47 (m, 2H), 2.37 (dd, J=15.3 and 5.3 Hz, 1H), 2.52 (dd, J=15.3 and 7.7 Hz, 1H), 3.94–4.07 (m, 1H), 4.10–4.20 (m, 2H), 4.27–4.38 (m, 1H), 6.23 (ddd, J=15.9, 7.4 and 6.6 Hz, 1H), 6.44 (d, J=15.9 Hz, 1H), 7.17–7.38 (m, 5H)ppm.

IR (liquid film): 2932, 2860, 1734, 1598 cm$^{-1}$.

Mass (m/z, %): 358 (M$^+$, 14), 241 (100), 155 (64), 143 (74), 129 (38), 99 (48), 91 (3H), 55 (16).

Reference Example 12

Ethyl 7-oxo-3,5-O-cyclohexylidene-3,5-dihydroxyheptanoate (Compound (21)):

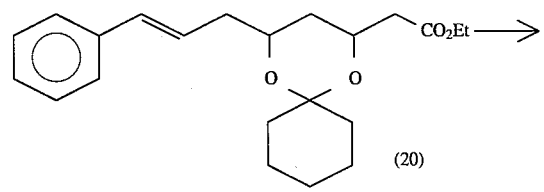

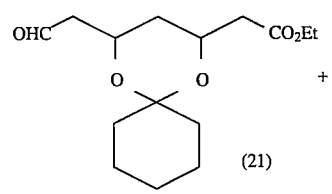

275 mg (0.77 mmol) of Compound (20) synthesized in Reference Example 11 was added to 7 ml of dichloromethane, and this solution was stirred at −78° C. Ozone was passed through this solution for 25 minutes. Excessive ozone was then purged from this reaction mixture with oxygen until the bluish reaction mixture became colorless.

To this reaction mixture, 241 mg (0.92 mmol) of triphenylphosphine was added, and the reaction mixture was stirred at room temperature for 1 hour and 35 minutes.

This reaction mixture was concentrated, and the residue was chromatographed on silica gel and eluted with a mixed solvent of hexane and ethyl acetate (2:1), whereby ethyl 7-oxo-3,5-O-cyclohexylidene-3,5-dihydroxyheptanoate (compound (21)) was obtained in the form of a colorless oil in a yield of 199 mg (91.2%).

$^1$HNMR (300 MHz, CDCl$_3$) δ1.22–1.36 (m, 1H), 1.27 (t, J=7.1 Hz, 3H), 1.34–1.50 (m, 4H), 1.50–1.63 (m, 4H), 1.66 (d with fine coupling, J=12.7 Hz, 1H), 1.82–2.05 (m, 2H), 2.38 (dd, J=15.3 and 5.5 Hz, 1H), 2.42–2.50 (m, 1H), 2.52 (dd, J=15.3 and 7.7 Hz, 1H), 2.62 (ddd, J=16.5, 7.8 and 2.3 Hz, 1H), 4.08–4.22 (m, 2H), 4.32–4.53 (m, 2H), 9.80 (s with fine coupling, 1H)ppm.

IR (liquid film): 2940, 2864, 1740 cm$^{-1}$.

Mass (m/z, %): 284 (M$^+$, 53), 241 (100), 39 (29), 81 (53), 55 (27).

EXAMPLE 6

Ethyl 7-[4'-fluoro-5,6-dimethoxy-3-(propan-2-yl)-biphenyl-2-yl]-3,5-O-cyclohexylidene-3,5,7-trihydroxyheptanoate (Compound (22)):

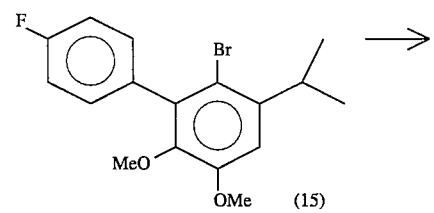

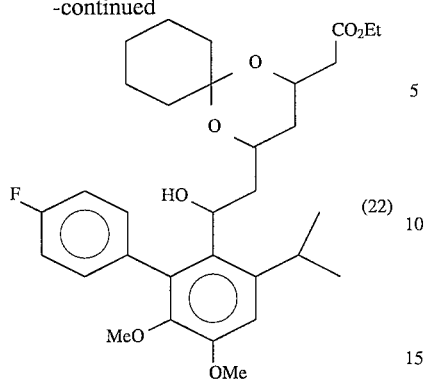

(22)

102 mg (4.90 mmol) of magnesium turnings was suspended in 1 ml of anhydrous THF. To this suspension, a solution of 0.12 ml (1.40 mmol) of 1,2-dibromoethene and 495 mg (1.40 mmol) of 2-bromo-4'-fluoro-5,6-dimethoxy-3-(propan-2-yl)biphenyl (Compound (15)) synthesized in Example 3 in 8 ml of anhydrous THF was added dropwise in a stream of argon over a period of 10 minutes.

This reaction mixture was refluxed for 30 minutes, and then cooled to room temperature.

To this reaction mixture, a solution of 333 mg (1.17 mmol) of Compound (21) synthesized in Reference Example 12 in 4 ml of anhydrous THF was added, and the mixture was stirred for 3 hours and 15 minutes.

This reaction mixture was then poured into 1N hydrochloric acid, and the mixture was then extracted with ethyl acetate. The ethyl acetate extract layer was successively washed with water, a saturated aqueous solution of sodium hydrogencarbonate, water, and a saturated aqueous solution of sodium chloride, dried over magnesium sulfate, and concentrated.

The residue was chromatographed on silica gel and eluted with a mixed solvent of ethyl acetate and hexane (1:6 to 1:2), whereby ethyl 7-[4'-fluoro-5,6-dimethoxy-3-(propan-2-yl)biphenyl-2-yl]-3,5-O-cyclohexylidene-3,5,7-trihydroxyheptanoate (compound (22)) was obtained in the form of a colorless amorphous solid in a yield of 242 mg (37.1%).

Mixture of 7:3 stereoisomers $^1$HNMR (300 MHz, CDCl$_3$) δ0.96–1.09 (m, 0.7H), 1.10–1.22 (m, 0.3H), 1.23–1.39 (m, 15H), 1.39–1.62 (m, 4H), 1.69–1.90 (m, 2H), 2.07–2.23 (m, 1H), 2.24–2.37 (m, 1H), 2.40–2.52 (m, 1H), 3.13–3.16 (m, 0.3H), 3.47 (s, 3H), 3.72–3.98 (m, 1H), 3.89 (s, 3H), 4.03–4.20 (m, 3H), 4.20–4.32 (m, 1H), 4.70–4.76 (m, 0.3H), 4.93–5.02 (m, 0.7H), 6.91 (s, 1H), 7.00–7.34 (m, 4H)ppm.

IR (KBr): 3532, 2940, 2868, 1740, 1592 cm$^{-1}$.

Mass (m/z, %): 558 (M$^+$, 16), 540 (40), 442 (100), 424 (76), 327 (76), 285 (75), 283 (86), 55 (34).

EXAMPLE 7

Ethyl (E)-7-[4'-fluoro-5,6-dimethoxy-3-(propan-2-yl)biphenyl-2-yl]-3,5-O-cyclohexylidene-3,5-dihydroxy-6-heptenoate (Compound (23)):

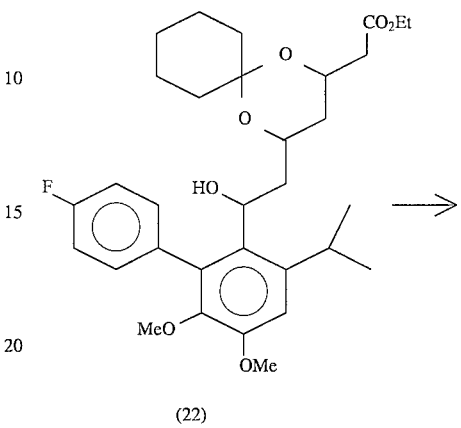

(22)

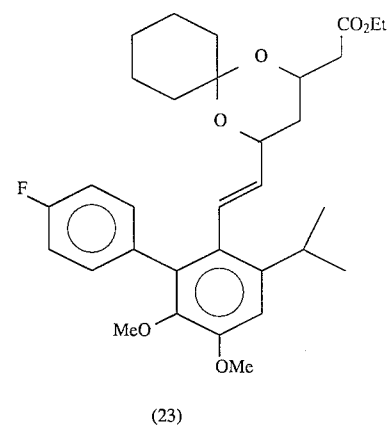

(23)

77 mg (0.14 mmol) of Compound (22) synthesized in Example 6 was dissolved in 2 ml of 1,2-dichloroethane. To this solution, at 0° C., 0.03 ml (0.37 mmol) of anhydrous pyridine and then 0.01 ml (0.15 mmol) of thionyl chloride were added, and the mixture was stirred in an atmosphere of argon for 30 minutes.

This reaction mixture was poured into water, and the mixture was extracted with ethyl acetate.

The ethyl acetate extract layer was successively washed with an aqueous solution of sodium hydrogencarbonate and a saturated aqueous solution of sodium chloride, dried over magnesium sulfate, and then concentrated.

The residue was dissolved in 3 ml of 1,2-dichloroethane, and 0.03 ml (0.37 mmol) of anhydrous pyridine was added thereto. This mixture was refluxed in an atmosphere of argon for 2 hours.

This reaction mixture was then added to water, and the mixture was then extracted with ethyl acetate. The ethyl acetate extract layer was washed with a saturated aqueous solution of sodium chloride, dried over magnesium sulfate, and concentrated.

The residue was chromatographed on silica gel and eluted with a mixed solvent of ethyl acetate and hexane (1:4), whereby ethyl (E)-7-[4'-fluoro-5,6-dimethoxy-3-(propan-2-yl)biphenyl- 2-yl]-3,5-O-cyclohexylidene-3,5-dihydroxy-6-heptenoate (compound (23)) was obtained in a yield of 53 mg (71.1%).

Melting point 118.0°–118.5° C. (colorless, fine particles, recrystallized from a mixed solvent of ethyl acetate and hexane)

$^1$HNMR (300 MHz, CDCl$_3$) δ0.97 (dd, J=24.4 and 11.7 Hz, 1H), 1.22 (d, J=6.8 Hz, 3H ), 1.22 (d, J=6.8 Hz, 3H), 1.27 (t, J=7.2 Hz, 3H), 1.27–1.46 (m, 5H), 1.46–1.57 (m, 4H), 1.75–1.95 (m, 2H), 2.32 (dd, J=15.4 and 5.6 Hz, 1H), 2.47 (dd, J=15.4 and 7.6 Hz, 1H), 3.25 (hept, J=6.8 Hz, 1H), 3.48 (s, 3H), 3.91 (s, 3H), 4.15 (q, J=7.2 Hz, 2H), 4.20–4.33 (m, 2H), 5.15 (dd, J=16.2 and 6.2 Hz, 1H), 6.23 (dd, J=16.2 and 1.1 Hz, 1H), 6.85 (s, 1H), 6.97–7.05 (m, 2H), 7.10–7.18 (m, 2H)ppm.

IR (KBr) 2948, 2856, 1740, 1606, 1588 cm$^{-1}$.

Mass (m/z, %): 540 (M$^+$, 100), 442 (72), 399 (31), 285 (48), 283 (31), 55 (8).

Reference Example 13 t-Butyl (E)-3,5-dioxo-8-phenyl-7-octenoate (Compound (24)):

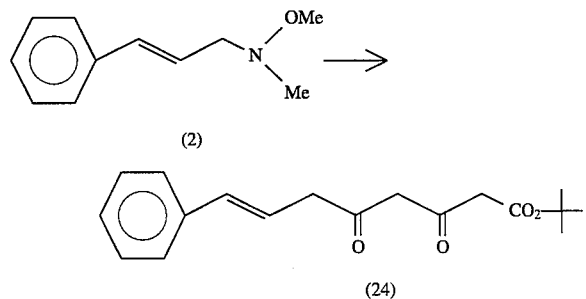

In a stream of argon, 8.10 ml (48.8 mmol) of t-butyl acetoacetate was added to a suspension of 1.78 g (44.5 mmol) of a 60% sodium hydride in 70 ml of anhydrous THF at 0° C., and the mixture was stirred at room temperature for 30 minutes.

This reaction mixture was cooled to 0° C., and 28.5 ml (47.3 mmol) of butyllithium (1.66M hexane solution) was added, and the mixture was stirred for 20 minutes.

The reaction mixture was cooled to −78° C., and a solution of 5.88 g (28.7 mmol) of Compound (2) synthesized in Reference Example 1 in 30 ml of anhydrous THF was added to the reaction mixture over a period of 15 minutes. This mixture was stirred for 1 hour and 35 minutes.

This reaction mixture was poured into diluted hydrochloric acid, and the mixture was extracted with ethyl acetate.

The ethyl acetate extract layer was washed with a saturated aqueous solution of sodium chloride, dried over magnesium sulfate, and then concentrated.

The residue was chromatographed on silica gel and eluted with a mixed solvent of hexane and ethyl acetate (5:1), whereby a crude product was obtained.

This crude product was chromatographed on silica gel and eluted with a mixed solvent of dichloromethane and ethyl acetate (100:1), whereby t-butyl (E)-3,5-dioxo-8-phenyl-7-octenoate (compound (24)) was obtained in the form of a colorless oil in a yield of 5.05 g (58.3%).

$^1$HNMR (300 MHz, CDCl$_3$) Keto:enol 15:85 mixture, δ1.45 (s, 7.65H), 1.46 (s, 1.35H), 3.10–3.18 (m, 1.7H), 3.25 (s, 1.7H), 3.44 (dd, J=7.1 and 1.2 Hz, 0.3H), 3.47 (s, 0.3H), 3.79 (s, 0.3H), 5.66 (s, 0.85H), 6.25 (dt, J=15.8 and 7.2 Hz, 0.85H), 6.19–6.32 (m, 0.15H), 6.51 (d, J=15.8 Hz, 1H), 7.20–7.41 (m, 5H) ppm.

IR (liquid film): 2984, 2936, 1732, 1604 cm$^{-1}$.

Mass (m/z, %): 302 (M$^+$, 1), 246 (14), 229 (11), 185 (26), 129 (100), 117 (25), 57 (35).

Reference Example 14 t-Butyl (E)-3,5-dihydroxy-8-phenyl-7-octenoate (Compound (25)):

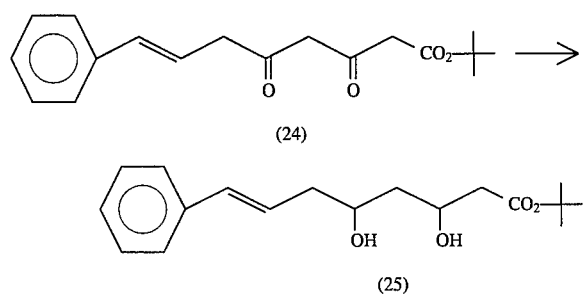

4.67 g (15.5 mmol) of Compound (24) synthesized in Reference Example 13 was dissolved in 20 ml of anhydrous THF and 10 ml of methanol. To this solution, 18.5 ml (18.5 mmol) of diethylmethoxyborane (1.0M THF solution) was added at −78° C. by use of a cooling bath in a stream of argon. The cooling bath was removed and the reaction mixture was stirred at room temperature for 30 minutes.

This reaction mixture was again cooled to −78° C., and 1.20 g (31.7 mmol) of sodium borohydride was added in two portions to the reaction mixture. The mixture was stirred for 5 hours.

This reaction mixture was then gradually added, with stirring at 0° C., to 180 ml of a 30% aqueous solution of hydrogen peroxide, and the mixture was stirred at room temperature overnight.

This reaction mixture was poured into a saturated aqueous solution of sodium chloride, and the mixture was extracted with ethyl acetate.

The ethyl acetate extract layer was successively washed with a saturated aqueous solution of sodium chloride, an aqueous solution of sodium thiosulfate, and a saturated aqueous solution of sodium chloride, dried over magnesium sulfate, and then concentrated.

The residue was chromatographed on silica gel and eluted with a mixed solvent of hexane and ethyl acetate (1:1), whereby t-butyl (E)-3,5-dihydroxy-8-phenyl-7-octenoate (compound (25)) was obtained in the form of a colorless oil in a yield of 3.80 g (80.8%).

$^1$HNMR (300 MHz, CDCl$_3$) δ1.46 (s, 9H), 1.54–1.68 (m, 2H), 2.35–2.46 (m, 4H), 3.48 (s, 1H), 3.82 (d, J=2.4 Hz, 1H), 3.94–4.08 (m, 1H), 4.18–4.31 (m, 1H), 6.24 (dt, J=15.9 and 7.2 Hz, 1H), 6.46 (d, J=15.9 Hz, 1–1H), 7.17–7.39 (m, 5H) ppm.

IR (liquid film): 3448, 2980, 2936, 1728, 1600 cm$^{-1}$.

Mass (FAB-positive, m/z, %): 307 ([M+H]$^+$, 5).

Mass (m/z, %): 270 (M$^+$-36, 25), 133 (45), 118 (44), 117 (42), 115 (100), 57 (60).

Reference Example 15 t-Butyl (E)-8-phenyl-3,5-O-isopropylidene-3,5-dihydroxy-7-octenoate (Compound (26)):

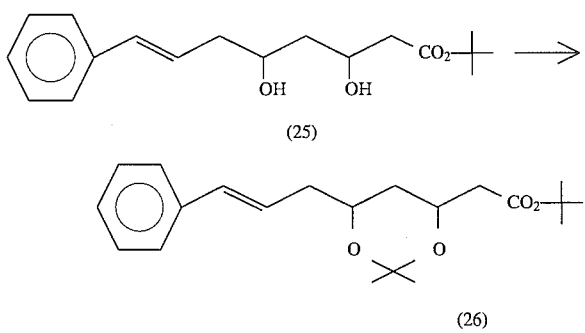

740 mg (2.43 mmol) of Compound (25) synthesized in Reference Example 14 was dissolved in 7.0 ml of 2,2-dimethoxypropane, and the mixture was stirred at room temperature in a stream of argon. To this solution, 5 mg (0.03 mmol) of p-toluenesulfonic acid monohydrate was added, and the mixture was stirred for 1 hour.

This reaction mixture was then poured into an aqueous solution of sodium hydrogencarbonate, and the mixture was then extracted with ethyl acetate. The ethyl acetate extract layer was washed with a saturated aqueous solution of sodium chloride, dried over magnesium sulfate, and concentrated.

The residue was chromatographed on silica gel and eluted with a mixed solvent of hexane and ethyl acetate (3:1), whereby t-butyl (E)-8-phenyl-3,5-O-isopropylidene-3,5-dihydroxy-7-octenoate (compound (26)) was obtained in the form of a colorless oil in a yield of 784 mg (93.6%).

$^1$HNMR (300 MHz, CDCl$_3$) δ1.16–1.30 (m, 1H), 1.40 (s, 3H), 1.43 (s, 9H), 1.47 (s, 3H), 1.62 (dt, J=12.8 and 2.4 Hz, 1H), 2.30 (dd, J=15.0 and 6.0 Hz, 1H), 2.25–2.52 (m, 2H), 2.43 (dd, J=15.0 and 7.2 Hz, 1H), 3.97 (dtd, J=11.5, 6.2 and 2.4 Hz, 1H), 4.20–4.32 (m, 1H), 6.14–6.28 (m, 1H), 6.43 (d, J=15.9 Hz, 1H), 7.17–7.38 (m, 5H) ppm.

IR (liquid film): 2984, 2940, 1732 cm$^{-1}$.

Mass (FAB-positive, m/z, %): 347 ([M+H]$^+$, 2).

Mass (m/z, %): 331 (M$^+$-15, 9), 215 (32), 173 (100), 155 (26), 115 (57), 57 (30).

Reference Example 16 t-Butyl 7-oxo-3,5-O-isopropylidene-3,5-dihydroxyheptanoate (Compound (27):

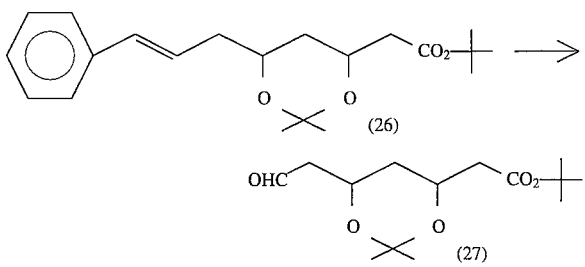

734 mg (2.13 mmol) of Compound (26) synthesized in Reference Example 15 was added to 40 ml of dichloromethane, and this solution was stirred at −78° C. Ozone was passed through this solution for 30 minutes. Excessive ozone was then purged from this reaction mixture with oxygen until the bluish reaction mixture became colorless.

To this reaction mixture, 670 mg (2.55 mmol) of triphenylphoephine was added, and the reaction mixture was stirred at for 2 hours and allowed to stand at 0° C. overnight.

This reaction mixture was concentrated, and the residue was chromatographed on silica gel and eluted with a mixed solvent of hexane and ethyl acetate (2:1), whereby t-butyl 7-oxo-3,5-O-isopropylidene-3,5-dihydroxyheptanoate (compound (27)) was obtained in the form of a colorless oil in a yield of 495 mg (85.3%).

$^1$HNMR (300 MHz, CDCl$_3$) δ1.20–1.34 (m, 1H), 1.36 (s, 3H), 1.45 (s, 9H), 1.48 (s, 3H), 1.66 (dt, J=12.7 and 2.5 Hz, 1H), 2.31 (dd, J=15.1 and 6.1 Hz, 1H), 2.43 (dd, J=15.1 and 7.1 Hz, 1H), 2.47 (ddd, J=16.7, 5.0 and 1.7 Hz, 1H), 2.62 (ddd, J=16.7, 7.3 and 2.3 Hz, 1H), 4.25–4.36 (m, 1H), 4.38–4.48 (m, 1H), 9.78 (dd, J=2.3 and 1.7 Hz, 1H) ppm.

IR (liquid film): 2988, 2944, 1726 cm$^{-1}$.

Mass (FAB-positive, m/z, %): 273 ([M+H]$^+$, 19).

Mass (m/z, %): 257 (M$^+$-15, 62), 201 (42), 149 (61), 141 (46), 59 (34), 57 (70).

EXAMPLE 8 t-Butyl 7-[4'-fluoro-5,6-dimethoxy-3-(propan-2-yl)biphenyl-2-yl]- 3,5-O-isopropylidene-3,5,7-trihydroxyheptanoate (Compound (28)):

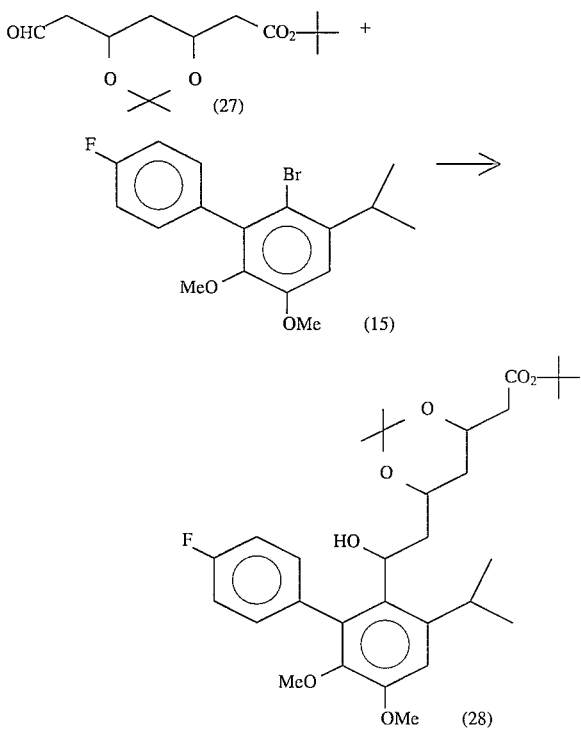

750 mg (2.11 mmol) of 2-bromo-4'-fluoro-5,6-dimethoxy-3-(propan-2-yl)biphenyl (compound (15)) synthesized in Example 3 and 213 mg (8.76 mmol) of magnesium turnings were added to 4 ml of anhydrous THF, and the mixture was refluxed in a stream of argon. To this suspension, a solution of 0.27 ml (2.10 mmol) of 1,2-dibromoethane in 4 ml of anhydrous THF was added dropwise over a period of 5 minutes. This reaction mixture was refluxed for 1 hour.

To this reaction mixture, a solution of 460 mg (1.69 mmol) of Compound (27) synthesized in Reference Example 16 in 2 ml of anhydrous THF was added, and the mixture was stirred at room temperature for 1 hour.

This reaction mixture was then poured into a saturated aqueous solution of ammonium chloride, and the mixture was then extracted with ethyl acetate. The ethyl acetate extract layer was washed with a saturated aqueous solution of sodium chloride, dried over magnesium sulfate, and concentrated.

The residue was chromatographed on silica gel and eluted with a mixed solvent of hexane and ethyl acetate (2:1), whereby t-butyl 7-[4'-fluoro-5,6-dimethoxy-3-(propan-2-yl)biphenyl-2-yl]-3,5-O-isopropylidene-3,5,7-trihydroxyheptanoate (compound (28)) was obtained in the form of a colorless amorphous solid in a yield of 670 mg (72.4%).

Mixture of 1:1 stereoisomers $^1$HNMR (CDCl$_3$, 300 MHz) δ0.84–1.18 (m, 1H), 1.20–1.48 (m, 13M), 1.43 (s, 4.5H), 1.45 (s, 4.5H), 2.04–2.44 (m, 4H), 2.92 (d, J=1.6 Hz, 0.5H), 3.46 (s, 1.5H), 3.47 (s, 1.5H), 3.89 (s, 3H), 3.70–4.25 (m, 3H), 4.68–4.78 (m, 0.5H), 4.87–4.97 (m, 0.5H), 6.91 (s, 1H), 7.00–7.23 (m, 4H) ppm.

IR (KBr): 3524, 2960, 1732, 1590 cm$^{-1}$.

Mass (m/z, %): 546 (M$^+$, 36), 528 (20), 470 (28), 414 (69), 371 (28), 303 (100), 302 (49), 301 (39), 285 (77), 57 (32).

EXAMPLE 9 t-Butyl 7-[4'-fluoro-5,6-dimethoxy-3-(propan-2-yl)biphenyl-2-yl]-3,5-O-isopropylidene-6-hetenoate (Compound (29)):

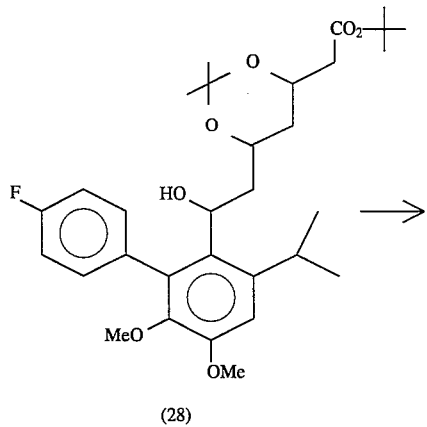

(28)

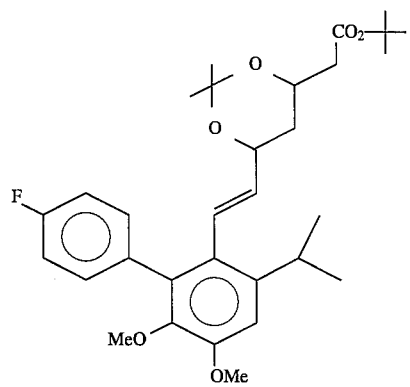

(29)

208 mg (0.38 mmol) of t-butyl 7-[4'-fluoro-5,6-dimethoxy-3-(propan-2-yl)biphenyl-2-yl]-3,5-O-isopropylidene-3,5,7-trihydroxyheptanoate (Compound (28)) synthesized in Example 8 was dissolved in 2.5 ml of 1,2-dichloroethane. To this solution, in a stream of argon at 0° C., 0.10 ml (1.24 mmol) of anhydrous pyridine and then 0.03 ml (0.41 mmol) of thionyl chloride were added, and the mixture was stirred for 1 hour.

This reaction mixture was poured into a saturated aqueous solution of sodium chloride, and the mixture was extracted with ethyl acetate.

The ethyl acetate extract layer was washed with an aqueous solution of sodium hydrogencarbonate and a saturated aqueous solution of sodium chloride, dried over magnesium sulfide, and then concentrated.

The residue was dissolved in 3 ml of 1,2-dichloroethane, and 0.10 ml (1.24 mmol) of anhydrous pyridine was added thereto. This mixture was refluxed in an atmosphere of argon for 2 hours.

This reaction mixture was then poured into a saturated aqueous solution of sodium chloride, and the mixture was then extracted with ethyl acetate. The ethyl acetate extract layer was washed with a saturated aqueous solution of sodium chloride, dried over magnesium sulfate, and concentrated.

The residue was chromatographed on silica gel and eluted with a mixed solvent of hexane and ethyl acetate (2:1), whereby t-butyl 7-[4'-fluoro-5,6-dimethoxy-3-(propan-2-yl)biphenyl-2-yl]-3,5-O-isopropylidene-6-hetenoate (compound (29)) was obtained in a yield of 157 mg (78.0%).

Melting points: 130.0°–131.0° C. (colorless needles, recrystallized from a mixed solvent of ethyl acetate and hexane)

$^1$HNMR (300 MHz, CDCl$_3$) δ0.82–0.96 (m, 1H), 1.22 (d, J=6.8 Hz, 3H), 1.23 (d, J=6.8 Hz, 3H), 1.18–1.37 (m, 1H), 1.34 (s, 3H), 1.43 (s, 3H), 1.45 (s, 9H), 2.23 (dd, J=15.3 and 6.2 Hz, 1H), 2.39 (dd, J=15.3 and 7.0 Hz, 1H), 3.25 (hept, J=6.8 Hz, 1H), 3.47 (s, 3H), 3.91 (s, 3H), 4.12–4.28 (m, 2H), 5.13 (dd, J=16.2 and 6.2 Hz, 1H), 6.22 (dd, J=16.2 and 1.1 Hz, 1H), 6.85 (s, 1H), 6.96–7.06 (m, 2H), 7.08–7.20 (m, 2H) ppm.

IR (KBr): 2968, 1728, 1604, 1588 cm$^{-1}$.

Mass (m/z, %): 528 (M$^+$, 44), 470 (33), 415 (31), 414 (100), 397 (43), 371 (56), 326 (39), 311 (38), 298 (39), 285 (84), 283 (93).

EXAMPLE 10

4'-fluoro-5,6-dimethoxy-3-(propan-2-yl)biphenyl-2-carbaldehyde (Compound (30)):

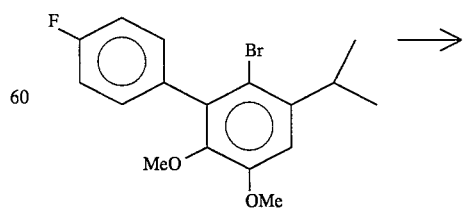

(15)

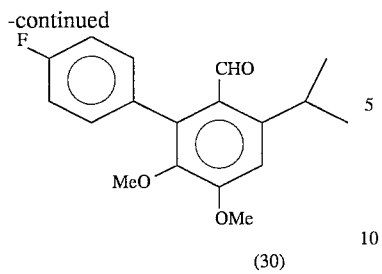

(30)

38.2 g (108 mmol) of 2-bromo-4'-fluoro-5,6-dimethoxy-3-(propan-2-yl)biphenyl (Compound (15)) synthesized in Example 3 was dissolved in 180 ml of anhydrous THF in an atmosphere of argon. To this solution, 72.2 ml (120 mmol) of butyl lithium (1.66M hexane solution) was added at −78° C., and the mixture was stirred for 20 minutes.

To this reaction mixture, 16.0 ml (130 mmol) of N-methylformanilide was added, and the mixture was stirred in an atmosphere of argon for 1 hour and 40 minutes.

To this reaction mixture, 2.0 ml (16.2 mmol) of N-methylformanilide was further added, and the mixture was stirred for 1 hour. This reaction mixture was poured into 1N hydrochloric acid, and the mixture was then extracted with ethyl acetate. The extract layer was successively washed with water and a saturated aqueous solution of sodium chloride, dried over magnesium sulfate, and concentrated. The residue was chromatographed on silica gel, and eluted with a mixed solvent of ethyl acetate and hexane (1:4). The eluant was concentrated, and the crude product was rechromatographed on silica gel, and eluted with a mixed solvent of ethyl acetate and hexane (1:4), whereby 4'-fluoro-5,6-dimethoxy-3-(propan-2-yl)biphenyl- 2-carbaldehyde (Compound (30)) was obtained in a yield 24.2 g (74.1%).

Melting point: 78.0°–79.0° C. (colorless particles, recrystallized from a mixed solvent of ethyl ace%ate and hexane)

$^1$HNMR (300 MHz, CDCl$_3$) δ1.28 (d, J=6.8 Hz, 6H), 3.50 (s, 3H), 3.98 (s, 3H), 4.05 (hept, J=6.8Hz, 1H), 7.00 (s, 1H), 7.08–7.17 (m, 2H), 7.23–7.31 (m, 2H), 9.66 (s, 1H)ppm.

IR (KBr): 2948, 2872, 1688, 1580 cm$^{-1}$.

Mass (m/z, %): 302 (M$^+$, 100), 287 (30), 269 (13), 183 (10), 149 (6).

Reference Example 17

(E)-3-[4'-fluoro-5,6-dimethoxy-3-(propan-2-yl)biphenyl-2-yl]-2-propenenitrile (Compound (31)):

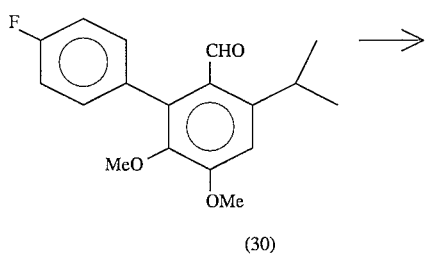

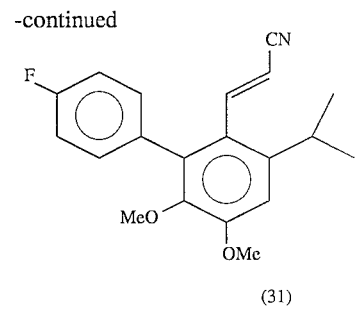

(31)

3.12 g (78.1 mmol) of a 60% sodium hydride was suspended in 190 ml of anhydrous THF, and to this suspension, 12.6 ml (78.1 mmol) of diethyl cyanomethylphosphonate was added at 0° C. in an atmosphere of argon.

To this reaction mixture, a solution of 22.5 g (74.4 mmol) of 4'-fluoro-5,6-dimethoxy-3-(propan-2-yl)biphenyl-2-carbaldehyde (Compound 30) synthesized in Example 10 in 110 ml of anhydrous THF, was added dropwise over a period of 10 minutes, and the mixture was stirred in an atmosphere of argon for 30 minutes.

The reaction mixture was then added to a 1N hydrochloric acid. This mixture was extracted with ethyl acetate. The extract layer was successively washed with water and with a saturated aqueous solution of sodium chloride, dried over magnesium sulfate, and then concentrated.

The residue was crystallized from ethyl acetate, whereby (E)-3-[4'-fluoro-5,6-dimethoxy-3-(propan-2-yl)biphenyl-2-yl]-2-propenenitrile (Compound 31) was obtained in a yield of 19.8 g (81.9%).

The filtrate obtained in the crystallization was concentrated, chromatographed on silica gel and eluted with a mixed solvent of ethyl acetate and hexane (1:4), whereby Compound 31 was further obtained in a yield of 0.88 g (3.6%).

Melting point: 167.0°–168.0° C. (colorless needles, recrystallized from ethyl acetate)

$^1$HNMR (300 MHz, CDCl$_3$) δ1.27 (d, J=6.8 Hz, 6H), 3.19 (hept, J=6.8 Hz, 1H), 3.47 (s, 3H), 3.94 (s, 3H), 4.89 (d, J=17.0 Hz, 1H), 6.90 (s, 1H), 7.07–7.19 (m, 4H), 7.30 (d, J=17.0 Hz, 1H)ppm.

IR (KBr): 2972, 2936, 2212, 1618, 1602, 1582 cm$^{-1}$.

Mass (m/z, %), 325 (M$^+$, 100), 310 (36), 285 (70), 254 (12), 196 (9), 183 (8).

Reference Example 18

(E)-3-[4'-fluoro-5,6-dimethoxy-3-(propan-2-yl)biphenyl-2-yl]-2-propenal (Compound (32)):

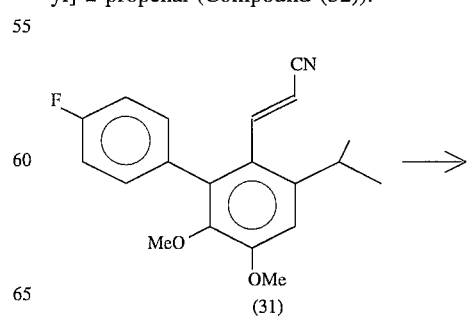

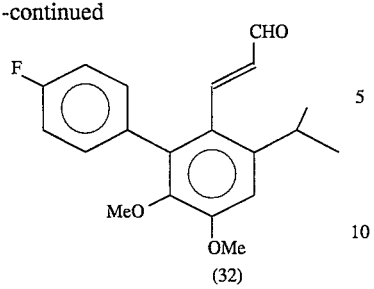

(32)

37.7 ml (66.2 mmol) of a 25% hexane solution of diisobutylaluminum hydride was dissolved in 50 ml of anhydrous toluene. This solution was cooled to −78° C.

To this solution was added dropwise a solution of 19.6 g (60.2 mmol) of (E)-3-[4'-fluoro-5,6-dimethoxy-3-(propan-2-yl)biphenyl-2-yl]-2-propenenitrile (Compound (31)) synthesized in Reference Example 17 in 300 ml of anhydrous THF in an atmosphere of argon over a period of 40 minutes.

This reaction mixture was stirred for 30 minutes, and was further stirred, with the temperature thereof raised to room temperature, overnight. With the addition of a small amount of methanol, this reaction mixture was added to a mixed solvent of a 1N hydrochloric acid and ethyl acetate at 0° C., and the mixture was stirred for 3 hours.

The ethyl acetate layer was successively washed with water and then with a saturated aqueous solution of sodium chloride, dried over magnesium sulfate, and concentrated.

The residue was crystallized from a mixed solvent of ethyl acetate and hexane, whereby (E)-3-[4'-fluoro-5,6-dimethoxy- 3-(propan-2-yl)biphenyl-2-yl]-2-propenal (Compound 32) was obtained in a yield of 13.6 g (69.1%).

The filtrate obtained in the crystallization was concentrated, chromatographed on silica gel and eluted with a mixed solvent of dichloromethane and hexane (2:1), and then with dichloromethane, whereby Compound 32 was further obtained in a yield of 3.75 g (19.0%).

Melting point 138.0°–139.0° C. (yellow, fine particles, recrystallized from a mixed solvent of ethyl acetate and hexane)

$^1$HNMR (300 MHz, CDCl$_3$) δ1.28 (d, J=6.8 Hz, 6H), 3.29 (hept, J=6.8 Hz, 1H), 3.49 (s, 3H), 3.95 (s, 3H), 5.89 (dd, J=16.4 and 7.7 Hz, 1H), 6.94 (s, 1H), 7.04–7.13 (m, 2H), 7.13–7.22 (m, 2H), 7.29 (d, J=16.4 Hz, 1H), 9.38 (d, J=7.7 Hz, 1H)ppm.

IR (KBr): 2968, 2936, 1674, 1622, 1584 cm$^{-1}$.

Mass (m/z, %), 328 (M$^+$, 27), 286 (54), 285 (100), 196 (12), 183 (17), 149 (13).

Reference Example 19

Ethyl (E)-7-[4'-fluoro-5,6-dimethoxy-3-(propan-2-yl)biphenyl- 2-yl]-5-hydroxy-3-oxo-6-heptenoate. (Compound (33):

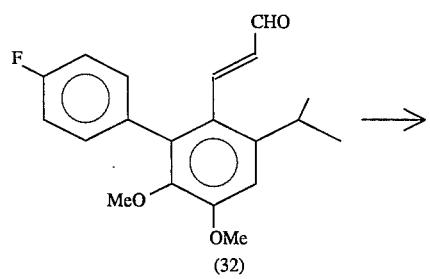

(32) →

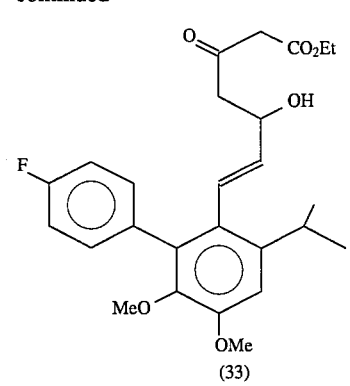

(33)

2.70 g (67.6 mmol) of a 60% sodium hydride was suspended in 100 ml of anhydrous THF in a stream of argon. To this suspension, 8.62 ml (67.6 mmol) of ethyl acetoacetate was added, and this mixture was stirred at 0° C. for 30 minutes.

With the addition of 43.3 ml (67.6 mmol) of a 1.66M hexane solution of butyllithium thereto, the reaction mixture was further stirred for 35 minutes, and then cooled to −78° C.

To this reaction mixture, a solution of 17.1 g (52.0 mmol) of (E)-3-[4'-fluoro-5,6-dimethoxy-3-(propan-2-yl)biphenyl-2-yl]-2-propenal (Compound (32)) synthesized in Reference Example 18 in 120 ml of anhydrous THF was dropwise added over a period of 20 minutes, and the reaction mixture was stirred for 55 minutes.

This reaction mixture was then added to a 1N solution of hydrochloric acid, and the mixture was extracted with ethyl acetate.

The extract layer was successively washed with water, and then with a saturated aqueous solution of sodium chloride, dried over magnesium sulfate, and concentrated.

The residue was chromatographed on silica gel and eluted with a mixed solvent of hexane and ethyl acetate (2:1), whereby ethyl (E)-7-[4'-fluoro-5,6-dimethoxy-3-(propan-2-yl)biphenyl- 2-yl]-5-hydroxy-3-oxo-6-heptenoate (Compound (33)) was obtained in a yield of 19.0 g (79.8%).

Melting point: 73.5°–74.0° C. (colorless, fine particles, recrystallized from a mixed solvent of ethyl acetate and hexane)

$^1$HNMR (300 MHz, CDCl$_3$) δ1.22 (d, J=6.8 Hz, 3H), 1.23 (d, J=6.8 Hz, 3H), 1.28 (t, J=7.1 Hz, 3H), 2.32–2.49 (m, 2H), 3.19 (hept, J=6.8 Hz, 1H), 3.40 (s, 2H), 3.48 (s, 3H), 3.91 (s, 3H), 4.20 (q, J=7.1 Hz, 2H), 4.42–4.52 (m, 1H), 5.14 (dd, J=16.1 and 6.3 Hz, 1H), 6.37 (dd, J=16.1 and 1.2 Hz, 1H), 6.86 (s, 1H), 7.01–7.10 (m, 2H), 7.10–7.19 (m, 2H)ppm.

IR (KBr): 3500, 2968, 2940, 1726, 1708 cm$^{-1}$.

Mass (m/z, %): 458 (M$^+$, trace), 440 (8), 328 (11), 285 (100), 183 (9), 43 (11).

Reference Example 20

Ethyl (E)-7-[4'-fluoro-5,6-dimethoxy-3-(propan-2-yl)biphenyl-2-yl]-3,5-dihydroxy-6-heptenoate (Compound (18)):

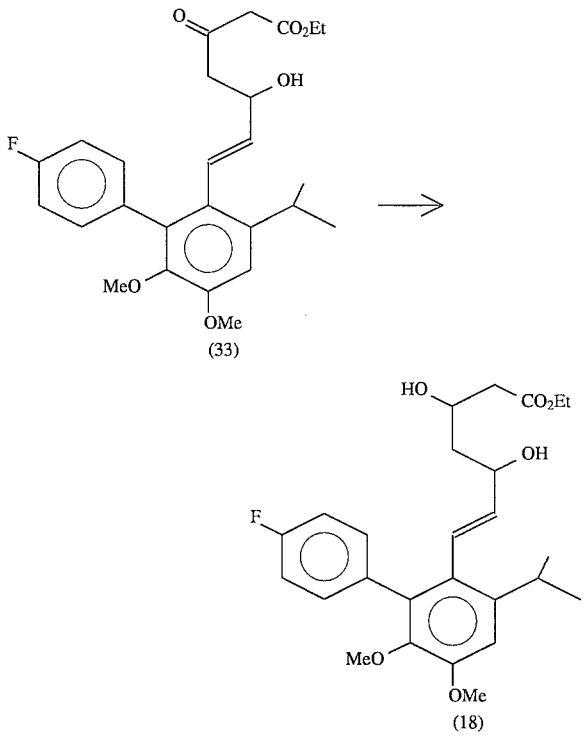

In an argon atmosphere, 45.1 ml (45.1 mmol) of triethylborane (1.0M THF solution) was added to 209 mg (2.05 mmol) of pivalic acid was added, and the mixture was stirred at room temperature for 1 hour and 15 minutes.

To this mixture, 18.8 g (41.0 mmol) of ethyl (E)-7-[4'-fluoro- 5,6-dimethoxy-3-(propan-2-yl)biphenyl-2-yl]-5-hydroxy-3-oxo-6-heptenoate (Compound (33)) synthesized in Reference Example 19, dissolved in 250 ml of anhydrous THF, was added, and the mixture was stirred for 1 hour and 10 minutes.

The reaction mixture was then cooled to −78° C., and 45 ml of methanol was added thereto. To this reaction mixture, 2.32 g (61.5 mmol) of sodium borohydride was added, with the entire amount being separated into several portions. The reaction mixture was then stirred for 1 hour and 40 minutes.

The reaction mixture was then gradually added, separated into several portions, to a mixed solution of 180 ml of a 30% aqueous solution of hydrogen peroxide and 180 ml of water at 0° C. The mixture was stirred overnight. The thus obtained reaction mixture was poured into 1N hydrochloric acid, and the mixture was then extracted with ethyl acetate.

The extract layer was successively washed with water, a saturated aqueous solution of sodium thiosulfate, water, and then a saturated aqueous solution of sodium chloride, dried over magnesium sulfate, and concentrated.

The residue was crystallized from a mixed solvent of ethyl acetate and hexane, whereby ethyl (E)-7-[4'-fluoro-5,6-dimethoxy-3-(propan-2-yl)biphenyl-2-yl]-3,5-dihydroxy-6-heptenoate (Compound (18)) synthesized in Reference Example 9 was obtained in a yield of 17.2 g (90.9%).

Reference Example 21

Methyl 6-(4-fluorophenyl)-4-hydroxy-2-oxo-4-(propan-2-yl)cyclohexane-1-carboxylate (Compound (35)):

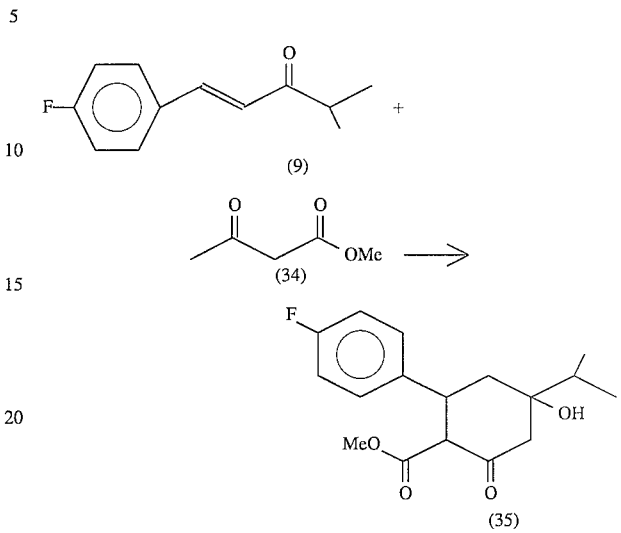

In an atmosphere of argon, 91.0 g (0.474 mol) of 1-(4-fluorophenyl)-4-methyl-1-penten-3-one (Compound (9)) synthesized in Reference Example 6 and 54.0 ml (0.500 mol) of methyl acetoacetate (Compound (34)) were added to 180 ml of t-butanol at room temperature, and the mixture was stirred. To this solution, 5.30 g (47.2 mmol) of potassium t-butoxide, and the mixture was stirred for 3 days.

A solid material which separated out from the above reaction mixture was filtered off, and washed with a mixed solvent of t-butanol and hexane, whereby methyl 6-(4-fluorophenyl)-4-hydroxy-2-oxo-4-(propan-2-yl)cyclohexane-1-carboxylate (Compound (35)) was obtained in the form of a colorless amorphous solid in a yield of 115.4 g (79.16).

$^1$HNMR (300 MHz, CDCl$_3$) δ0.98 (d, J=6.9 Hz, 3H), 0.98 (d, J=6.9 Hz, 3H), 1.76 (hept, J=6.9 Hz, 1H), 1.93 (dd, J=13.9 and 12.0 Hz, 1H), 2.01 (ddd, J=13.9, 4.8 and 2.2 Hz, 1H), 2.50 (dd, J=14.0 and 2.3 Hz, 1H), 2.60 (d, J=14.0 Hz, 1H), 3.59 (s, 3H), 3.59 (d, J=12.5 Hz, 1H), 3.84 (ddd, J=12.5, 12.0 and 4.8 Hz, 1H), 6.96–7.06 (m, 2H), 7.20–7.30 (m, 2H)ppm.

IR (KBr): 3460, 2968, 1754, 1714, 1606 cm$^{-1}$.

Mass (m/z, %): 308 (M$^+$, 8), 290 (45), 247 (50), 233 (38), 231 (35), 215 (87), 149 (100).

Reference Example 22

Methyl 6-(4-fluorophenyl)-2-oxo-4-(propan-2-yl)-3-cyclohexene-1-carboxylate (Compound (36)):

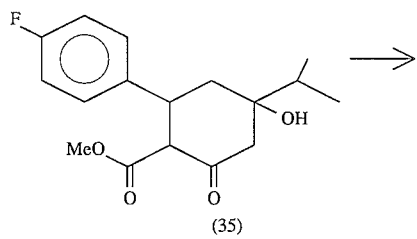

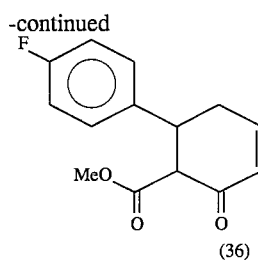

60.0 g (0.195 mol) of methyl 6-(4-fluorophenyl)-4-hydroxy- 2-oxo-4-(propan-2-yl)cyclohexane-1-carboxylate (Compound (35)) synthesized in Reference Example 21 and 20.0 (0.166 mol) of anhydrous magnesium sulfate were added to 300 ml of dichoromethane. In an atmosphere of argon, 5.0 ml (60.0 mmol) of concentrated hydrochloric acid was added dropwise, with stirring, to the above mixture at room temperature, and this mixture was stirred for 22 hours and 30 minutes.

This reaction mixture was diluted with ethyl acetate and filtered through Celite. The filtrate was successively washed with an aqueous solution of sodium hydrogencarbonate and a saturated aqueous solution of sodium chloride, dried over magnesium sulfate, and concentrated.

The residue was crystallized from a mixed solvent of ethyl acetate and hexane, whereby methyl 6-(4-fluorophenyl)- 2-oxo-4-(propan-2-yl)-3-cyclohexene-1-carboxylate (Compound (36)) was obtained in a yield of 35.6 g (63.0%).

Melting point: 102.0°–103.0° C. (colorless particles, recrystallized from ethanol)

$^1$HNMR (300 MHz, CDCl$_3$) δ1.13 (d, J=6.9 Hz, 6H), 2.47 (hept, J=6.9 Hz, 1H), 2.50–2.60 (m, 2H), 3.58 (s, 3H), 3.60–3.65 (m, 2H), 6.03 (d, J=1.2 Hz, 1H), 6.98–7.07 (m, 2H), 7.20–7.28 (m, 2H)ppm.

IR (KBr): 2972, 1748, 1668, 1620 cm$^{-1}$.

Mass (m/z, %): 290 (M$^+$, 100), 257 (30), 231 (81), 215 (32), 189 (51), 110 (33), 95 (28).

Reference Example 23

Methyl 4'-fluoro-3-hydroxy-5-(propan-2-yl)biphenyl-2-carboxylate (Compound (37)):

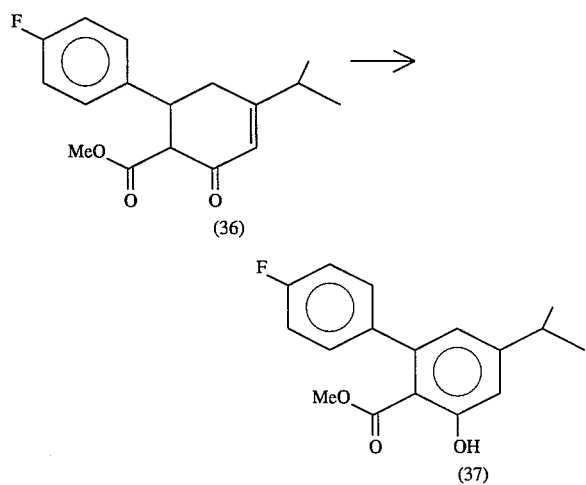

3.03 g (10.5 mmol) of methyl 6-(4-fluoro-phenyl)-2-oxo-4-(propan-2-yl)-3-cyclohexene-1-carboxylate (Compound (36)) synthesized in Reference Example 22, 1.50 ml (10.0 mmol) of isophorone, and 603 mg of 10% Pd—C were added to 25 ml of diethylene glycol dimethyl ether.

This reaction mixture was then refluxed, with a nitrogen gas being bubbled therethrough, for 2 hours.

The reaction mixture was diluted with ethyl acetate, and filtered through Celite, and concentrated.

The residue was chromatographed on silica gel and eluted with dichloromethane, whereby methyl 4'-fluoro-3-hydroxy-5-(propan-2-yl)biphenyl-2-carboxylate (Compound (37)) was obtained in the form of a colorless oil in a yield of 1.84 g (60.1%).

$^1$HNMR (300 MHz, CDCl$_3$) δ1.25 (d, J=6.9 Hz, 6H), 2.88 (hept, J=6.9 Hz, 1H), 3.50 (s, 3H), 6.63 (d with fine coupling, 1H), 6.88 (d with fine coupling, 1H), 7.00–7.10 (m, 2H), 7.15–7.23 (m, 2H), 10.82 (s, 1H)ppm.

IR (liquid film): 2964, 1668, 1614 cm$^{-1}$.

Mass (m/z, %): 288 (M$^+$, 28), 256 (100), 213 (24), 183 (11).

Reference Example 24

Methyl 4'-fluoro-3-methoxy-5-(propan-2-yl)biphenyl-2-carboxylate (Compound (38)):

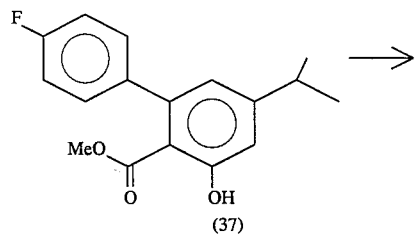

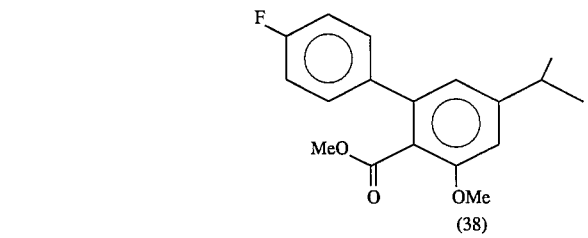

44.5 g (0.155 mol) of methyl 4'-fluoro-3-hydroxy-5-(propan-2-yl)biphenyl-2-carboxylate (Compound (37)) synthesized in Reference Example 23 was dissolved in 300 ml of DMF, and 10.6 ml (0.170 mmol) of methyl iodide and 63.9 g (0.462 mol) of potassium carbonate were successively added thereto. This reaction mixture was stirred in an atmosphere of argon at room temperature for 3 days.

The reaction mixture was then poured into water, and the mixture was extracted with ethyl acetate. The extract layer was washed with a saturated aqueous solution of sodium chloride, dried over magnesium sulfate, and concentrated. The residue was chromatographed on silica gel, and eluted with a mixed solvent of ethyl acetate and hexane (1:4), whereby methyl 4'-fluoro-3-methoxy-5-(propan-2-yl)biphenyl-2-carboxylate (Compound (38)) was obtained in a yield of 45.2 g (97.0%).

Melting points: 85.0°–86.0° C. (colorless needles, recrystallized from hexane)

$^1$HNMR (300 MHz, CDCl$_3$) δ1.28 (d, J=6.9 Hz, 6H), 2.94 (hept, J=6.9 Hz, 1H), 3.63 (s, 3H), 3.88 (s, 3H), 6.80 (s, 1H), 6.80 (s, 1H), 7.02–7.13 (m, 2H), 7.30–7.40 (m, 2H)ppm.

IR (KBr): 2964, 1732, 1608 cm$^{-1}$.

Mass (m/z, %): 302 (64), 287 (11), 271 (100), 183 (14).

Reference Example 25

Methyl 6-bromo-4'-fluoro-3-methoxy-5-(propan-2-yl)biphenyl-2-carboxylate (Compound (39)):

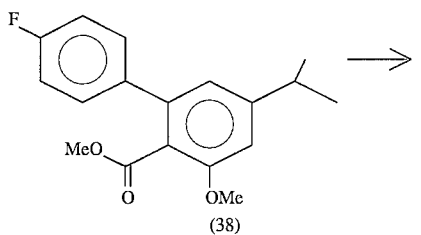

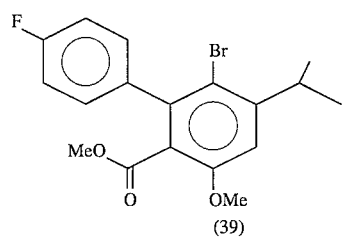

45.2 g (0.150 mol) of methyl 4'-fluoro-3-methoxy-5-(propan- 2-yl)biphenyl-2-carboxylate (Compound (38)) synthesized in Reference Example 24 was dissolved in a mixed solvent of 230 ml of THF and 23 ml of water. To this solution, 28.0 g (0.178 mol) of N-bromosuccinimide was added at 0° C. This reaction mixture was stirred in an atmosphere of argon at room temperature for 1 hour and 30 minutes.

The reaction mixture was poured into water, and the mixture was extracted with ethyl acetate. The extract layer was successively washed with a saturated aqueous solution of sodium thiosulfate, water, and a saturated aqueous solution of sodium chloride, dried over magnesium sulfate, and concentrated. The residue was crystallized from a mixed solvent of ethyl acetate and hexane, whereby methyl 6-bromo-4'-fluoro-3-methoxy-5-(propan-2-yl)biphenyl-2-carboxylate (Compound (39)) was obtained in a yield of 43.4 g (76.1%).

The filtrate obtained in the above crystallization was concentrated, chromatographed on silica gel, and eluted with a mixed solvent of dichloromethane and hexane (1:1), whereby methyl 6-bromo-4'-fluoro-3-methoxy-5-(propan-2-yl)biphenyl-2-carboxylate (Compound (39)) was further obtained in a yield of 2.45 g (4.3%).

Melting point 104.5°–105.5° C. (colorless columns, recrystallized from hexane)

$^1$HNMR (300 MHz, CDCl$_3$) δ1.28 (d, J=6.8 Hz, 6H), 3.50 (s, 3H), 3.50 (hept, J=6.8 Hz, 1H), 3.88 (s, 3H), 6.88 (s, 1H), 7.02–7.13 (m, 2H), 7.17–7.28 (m, 2H)ppm.

IR (KBr): 2964, 2952, 1736 cm$^{-1}$.

(m/z, %): 382 (M$^+$, 100), 380 (M$^+$, 100), 351 (83), 349 (87), 335 (38), 333 (38), 183 (35).

Reference Example 26

6-Bromo-4'-fluoro-3-methoxy-5-(propan-2-yl)biphenyl-2-methanol (Compound (40)):

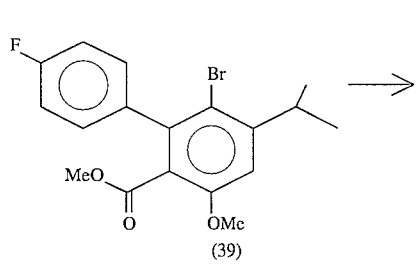

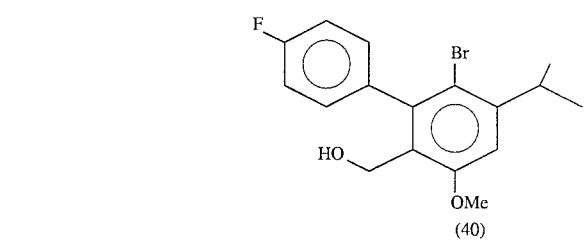

In an atmosphere of argon, 137 ml (0.241 mol) of a 25% hexane solution of diisobutylaluminum hydride was added, with stirring, at −78° C. to a solution of methyl 6-bromo-4'-fluoro-3-methoxy-5-(propan-2-yl)biphenyl-2-carboxylate (Compound (39)) prepared in Reference Example 25 in 300 ml of anhydrous toluene.

This reaction mixture was stirred for 50 minutes. With the addition of a small amount of methanol, the reaction mixture was poured into a mixed solvent of 1N hydrochloric acid and ethyl acetate at 0° C., and the mixture was further stirred overnight.

The ethyl acetate layer was successively washed with water and then with a saturated aqueous solution of sodium chloride, dried over magnesium sulfate, and concentrated.

The residue was chromatographed on silica gel and eluted with a mixed solvent of ethyl acetate and hexane (1:4), whereby 6-bromo-4'-fluoro-3-methoxy-5-(propan-2-yl)biphenyl-2-methanol (Compound (40)) was obtained in the form of a colorless oil in a quantitative yield.

$^1$HNMR (300 MHz, CDCl$_3$) δ1.28 (d, J=6.8 Hz, 6H), 2.23 (t, J=6.7 Hz, 1H), 3.48 (hept, J=6.8 Hz, 1H), 3.93 (s, 3H), 4.35 (d, J=6.7 Hz, 2H), 6.89 (s, 1H), 7.08–7.22 (m, 4H)ppm.

IR (liquid film): 3452, 2968, 1588 cm$^{-1}$.

Mass (m/z, %): 354 (M$^+$, 100), 352 (M$^+$, 100), 307 (14,), 305 (14), 273 (16), 255 (38), 230 (26), 196 (25), 183 (31).

Reference Example 27

6-Bromo-4'-fluoro-3-methoxy-5-(propan-2-yl)biphenyl-2-carbaldehyde (Compound (41)):

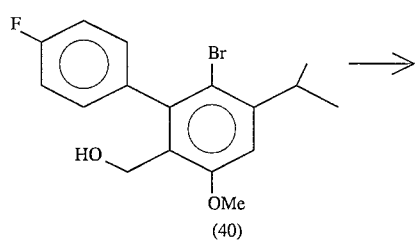

-continued

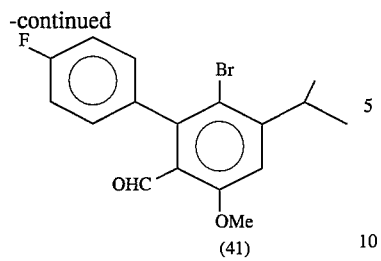
(41)

In an atmosphere of argon, 7.63 ml (54.7 mmol) of triethylamine, 9 ml of anhydrous THF and 7.59 g (48.3 mmol) of a sulfur trioxide pyridine complex were successively added to a solution of 5.04 g (14.3 mmol) of 6-bromo-4'-fluoro-3-methoxy-5-(propan-2-yl)biphenyl-2-methanol (Compound (40)) prepared in Reference Example 26 in 30 ml of anhydrous DMSO, and the mixture was stirred for 40 minutes.

To this reaction mixture, water was added, and the mixture was poured into diluted hydrochloric acid.

This mixture was extracted with ethyl acetate. The ethyl acetate layer was successively washed with an aqueous solution of sodium hydrogencarbonate, and then with a saturated aqueous solution of sodium chloride, dried over magnesium sulfate, and concentrated.

The residue was chromatographed on silica gel and eluted with a mixed solvent of ethyl acetate and hexane (1:3), whereby 6-bromo-4'-fluoro-3-methoxy-5-(propan-2-yl)biphenyl-2-carbaldehyde (Compound (41)) was obtained in a yield of 40.5 g (80.7%).

Melting point: 69.0°–70.0° C. (pale yellow particles, recrystallized from hexane)

$^1$HNMR (300 MHz, CDCl$_3$) δ1.31 (d, J=6.8 Hz, 6H), 3.53 (hept, J=6.8 Hz, 1H), 3.97 (s, 3H), 6.98 (s, 1H), 7.12 (s, 2H), 7.14 (s, 2H), 9.87 (s, 1H)ppm.

IR (KBr): 2968, 1690, 1580 cm$^{-1}$.

Mass (m/z, %): 352 (M$^+$, 98), 350 (M$^+$, 100), 271 (44), 183 (38).

EXAMPLE 11

2-Benzyloxy-6-bromo-4'-fluoro-3-methoxy-5-(propan-2-yl)biphenyl (Compound (43)):

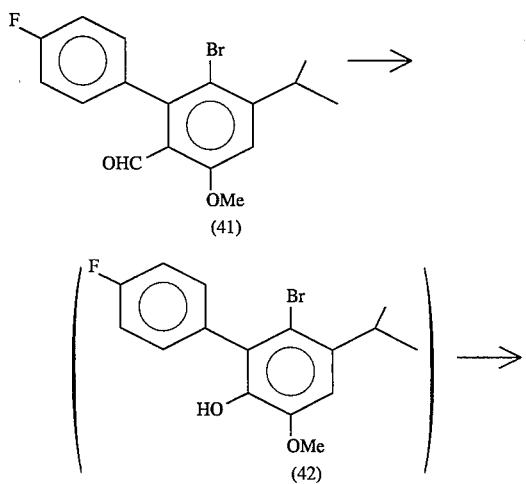

-continued

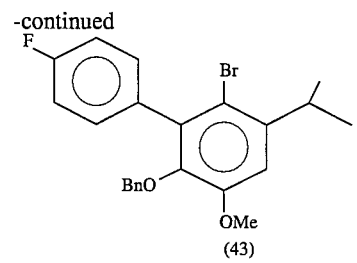
(43)

32.9 g (93.8 mmol) of 6-bromo-4'-fluoro-3-methoxy-5-(propan-2-yl)biphenyl-2-carbaldehyde (Compound (41)) synthesized in Reference Example 27 was dissolved in 200 ml of 1,2-dichloroethane, and this reaction mixture was stirred in an atmosphere of argon at room temperature.

To this reaction mixture, 27.8 g (0.113 mol) of m-chloroperbenzoic acid (70%) was added, with stirring, and the mixture was stirred at 0° C. for 35 minutes, and at room temperature for 40 minutes.

The reaction mixture was poured into an aqueous solution of sodium hydrogencarbonate, and the mixture was extracted with ethyl acetate. The extract layer was successively washed with a saturated aqueous solution of sodium chloride, an aqueous solution of sodium thiosulfate, and a saturated aqueous solution of sodium chloride, dried over magnesium sulfate, and concentrated.

To the residue, 150 ml of methanol was added. In an atmosphere of argon, the mixture was stirred at room temperature. To this solution, 8.57 ml (0.141 mol) of a 28% ammonia water was added, and the mixture was stirred at room temperature for 20 minutes, and at 0° C. for 10 minutes.

This reaction mixture was poured into water, and the mixture was extracted with ethyl acetate. The extract layer was successively washed with 1N hydrochloric acid and a saturated aqueous solution of sodium chloride, dried over magnesium sulfate, and concentrated, whereby a crude 6-bromo-4'-fluoro-3-methoxy-5-(propan-2-yl)biphenyl-2-ol (Compound (42)) was obtained in a yield of 30.3 g.

$^1$HNMR (300 MHz, CDCl$_3$) δ1.26 (d, J=6.8 Hz, 6H), 3.44 (hept, J=6.8 Hz, 1H), 3.94 (s, 3H), 5.51 (s, 1H), 6.83 (s, 1H), 7.10– 7.20 (m, 2H), 7.22–7.32 (m, 2H)ppm.

IR (liquid film): 3548, 2968, 1596 cm$^{-1}$.

Mass (m/z, %): 340 (M$^+$, 88), 338 (M$^+$, 92), 325 (100), 323 (98), 244 (28), 229 (19).

29.8 g (87.9 mmol) of crude Compound (42) was dissolved in 150 ml of DMF, with stirring at room temperature. To this solution, 12.6 ml (0.106 mol) of benzyl bromide and 36.4 g (0.264 mol) of potassium carbonate were successively added.

This reaction mixture was stirred in an atmosphere of argon at room temperature for 3 days.

The reaction mixture was then poured into water, and the mixture was extracted with ethyl acetate. The extract layer was washed with a saturated aqueous solution of sodium chloride, dried over magnesium sulfate, and concentrated.

The residue was crystallized from a mixed solvent of ethyl acetate and hexane, whereby 2-benzyloxy-6-bromo-4'-fluoro- 3-methoxy-5-(propan-2-yl)biphenyl (Compound (43)) was obtained in a yield of 27.6 g (73.2%).

The filtrate obtained in the above crystallization was concentrated, chromatographed on silica gel, and eluted with a mixed solvent of ethyl acetate and hexane (1:10), whereby Compound (43) was further obtained in a yield of 8.68 g (23.0%).

Melting point: 115.0°–116.5° C. (colorless columns, recrystallized from a mixed solvent of ethyl acetate and hexane)

¹HNMR (300 MHz, CDCl₃) δ1.28 (d, J=6.9 Hz, 6H), 3.46 (hept, J=6.9 Hz, 1H), 3.92 (s, 3H), 4.66 (s, 2H), 6.91 (s, 1H), 6.90–6.99 (m, 2H), 7.03–7.13 (m, 2H), 7.15–7.30 (m, 5H)ppm.

IR (KBr): 2956, 1600, 1574 cm⁻¹.

Mass (m/z, %): 430 (M⁺, 45), 428 (M⁺, 45), 297 (10), 295 (11), 258 (20), 243 (24), 216 (24), 91 (100).

EXAMPLE 12

6-Benzyloxy-4'-fluoro-5-methoxy-3-(propan-2-yl)biphenyl-2-carbaldehyde (Compound (44)):

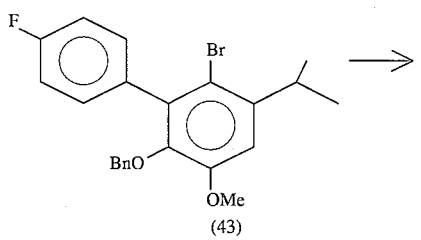

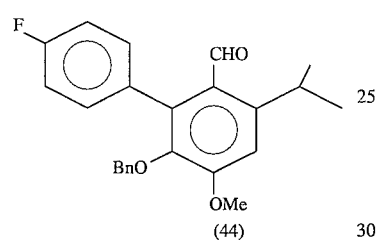

35.0 g (81.6 mmol) of 2-benzyloxy-6-bromo-4'-fluoro-3-methoxy-5-(propan-2-yl)biphenyl (Compound (43)) synthesized in Example 11 was dissolved in 150 ml of anhydrous THF, and this solution was stirred in an atmosphere of argon at −78° C.

With the addition of 54.8 ml (91.0 mmol) of a 1.66M hexane solution of butyllithium thereto, the reaction mixture was further stirred for 20 minutes.

To this reaction mixture, 15.1 ml (0.122 mol) of N-methylformanilide was added, and the reaction mixture was stirred for 1 hour and 30 minutes.

This reaction mixture was then poured into 1N hydrochloric acid, and the mixture was extracted with ethyl acetate.

The extract layer was successively washed with water, and then with a saturated aqueous solution of sodium chloride, dried over magnesium sulfate, and concentrated.

The residue was crystallized from a mixed solvent of ethyl acetate and hexane, whereby 6-benzyloxy-4'-fluoro-5-methoxy- 3-(propan-2-yl)biphenyl-2-carbaldehyde (Compound (44)) was obtained in a yield of 15.9 g (51.5%).

The filtrate obtained in the crystallization was concentrated, chromatographed on silica gel, and eluted with a mixed solvent of ethyl acetate and hexane (1:10), whereby Compound (44) was further obtained in a yield of 8.68 g (26.7%).

Melting points: 141.0°–142.0° C. (colorless needles, recrystallized from a mixed solvent of ethyl acetate and hexane)

¹HNMR (300 MHz, CDCl₃) δ1.29 (d, J=6.8 Hz, 6H), 4.00 (s, 3H), 4.07 (hept, J=6.8 Hz, 1H), 4.65 (s, 2H), 6.92–7.01 (m, 2H), 7.03 (s, 1H), 7.01–7.13 (m, 2H), 7.17–7.29 (m, 5H), 9.67 (s, 1H)ppm.

IR (KBr): 2972, 2944, 1682, 1598, 1580 cm⁻¹.

Mass (m/z, %): 378 (M⁺, 66), 287 (32), 269 (37), 91 (100).

Reference Example 28

(E)-3-[6-benzyloxy-4'-fluoro-5-methoxy-3-(propan-2-yl)biphenyl- 2-yl]-2-propenenitrile (Compound (45)):

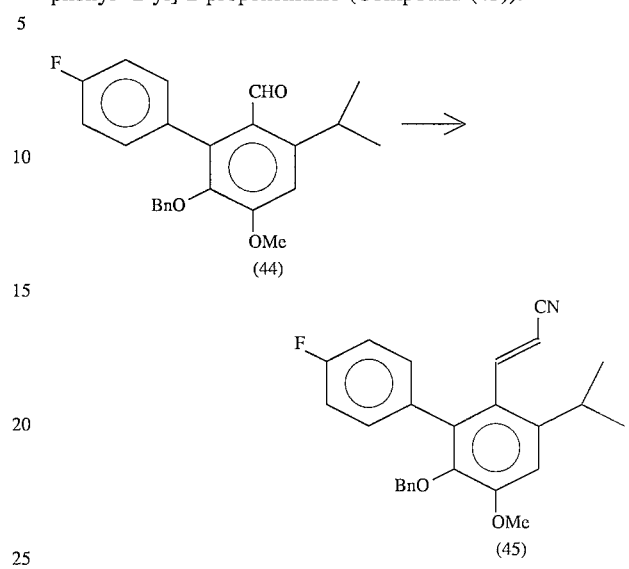

In an atmosphere of argon, 2.64 g (66.0 mmol) of a 60% sodium hydride was suspended in 100 ml of anhydrous THF. To this suspension, 10.7 ml (66.0 mmol) of diethyl cyanomethylphosphonate was added at 0° C.

To this reaction mixture, a solution of 23.7 g (62.8 mmol) of 6-benzyloxy-4'-fluoro-5-methoxy-3-(propan-2-yl)biphenyl-2-carbaldehyde (Compound (44)) synthesized in Example 12 in 180 ml of THF, was added dropwise with stirring over a period of 10 minutes. This reaction mixture was stirred was then stirred for 50 minutes.

The reaction mixture was then added to a saturated aqueous solution of ammonium chloride. This mixture was extracted with ethyl acetate.

The ethyl acetate extract layer was successively washed with water and then with a saturated aqueous solution of sodium chloride, dried over magnesium sulfate, and then concentrated. The residue was then crystallized from a mixed solvent of ethyl acetate and hexane, whereby (E)-3-[6-benzyloxy-4'-fluoro-5-methoxy-3-(propan- 2-yl)biphenyl-2-yl]-2-propenenitrile (Compound (45)) was obtained in a yield of 15.9 g (63.0%).

The filtrate obtained in the crystallization was concentrated, chromatographed on silica gel and eluted with a mixed solvent of ethyl acetate and hexane (1:4), whereby Compound (45) was further obtained in a yield of 4.50 g (17.9%).

Melting point 175.0°–175.5° C. (colorless needles, recrystallized from a mixed solvent of ethyl acetate and hexane)

¹HNMR (300 MHz, CDCl₃) δ1.28 (d, J=6.8 Hz, 6H), 3.20 (hept, J=6.8 Hz, 1H),3.96 (s, 3H), 4.62 (s, 2H), 4.90 (d, J=17.0 Hz, 1H), 6.92 (s, 1H), 6.90–6.98 (m, 2H), 7.03–7.15 (m, 4H), 7.18–7.25 (m, 3H), 7.31 (d, J=17.0 Hz, 1H)ppm.

IR (KBr) 2972, 2216, 1620, 1582 cm⁻¹.

Mass (m/z, %): 401 (M⁺, 52), 310 (10), 268 (40), 253 (16), 91 (100).

Reference Example 29

(E)-3-[6-benzyloxy-4'-fluoro-5-methoxy-3-(propan-2-yl)biphenyl-2-yl]-2-propenal (Compound (46)):

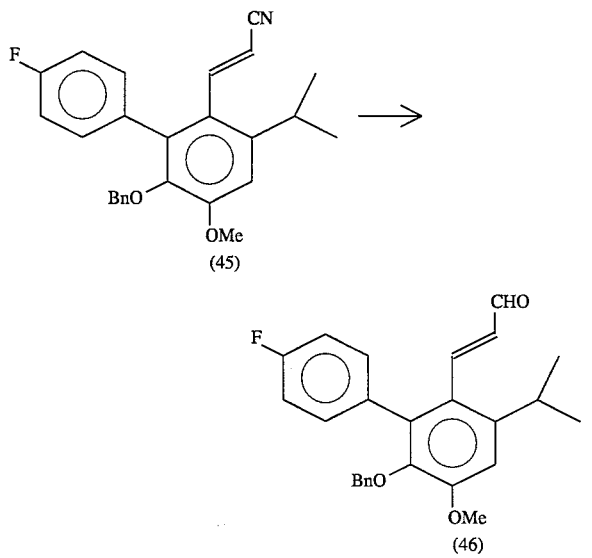

To a solution prepared by adding 34.5 ml (60.6 mmol) of a 25% hexane solution of diisobutylaluminum hydride to 50 ml of anhydrous toluene, a solution prepared by dissolving 22.1 g (55.1 mmol) of (E)-3-[6-benzyloxy-4'-fluoro-5-methoxy-3-(propan-2-yl)biphenyl-2-yl]-2-propenenitrile (Compound (45)) synthesized in Reference Example 28 in 250 ml of anhydrous toluene was added dropwise over a period of 50 minutes. After the dropwise addition of the toluene solution of Compound (45), the reaction mixture was stirred for 20 minutes.

To this reaction mixture, methanol was added until bubbles were not formed any longer in the reaction mixture.

The reaction mixture was then added to a 1N hydrochloric acid at room temperature. To this mixture, ethyl acetate was added, and the mixture was stirred for 2 hours and 40 minutes.

The ethyl acetate layer was separated, washed with water and then with a saturated aqueous solution of sodium chloride, and dried over magnesium sulfate and then concentrated.

The residue was then crystallized from a mixed solvent of ethyl acetate and hexane, whereby (E)-3-[6-benzyloxy-4'-fluoro-5-methoxy-3-(propan-2-yl)biphenyl-2-yl]-2-propenal (Compound (46)) was obtained in a yield of 18.8 g (84.3%).

The filtrate obtained in the crystallization was concentrated, chromatographed on silica gel and eluted with a mixed solvent of ethyl acetate and hexane (1:3), whereby Compound (46) was further obtained in a yield of 777 mg (3.5%).

Melting point: 129.5°–130.5° C. (colorless needles, recrystalllzed from a mixed solvent of ethyl acetate and hexane)

$^1$HNMR (300 MHz, CD$_3$OD) δ1.31 (d, J=6.8 Hz, 6H), 3.35 (hept, J=6.8 Hz, 1H), 3.99 (s, 3H), 4.67 (s, 2H), 5.71 (dd, J=16.2 and 7.7 Hz, 1H), 6.91–6.96 (m, 2H), 7.05–7.22 (m, 8H), 7.59 (d, J=16.2 Hz, 1H), 9.34 (d, J=7.7 Hz, 1H)ppm.

IR (KBr), 3064, 1688, 1582 cm$^{-1}$.

Mass (m/z, %): 404 (M$^+$, 27), 361 (100), 313 (16), 271 (26), 253 (17), 91 (72).

Reference Example 30

Ethyl (E)-7-[6-benzyloxy-4'-fluoro-5-methoxy-3-(propan-2-yl)biphenyl-2-yl]- 5-hydroxy-3-oxo-6-heptenoate (Compound (47)):

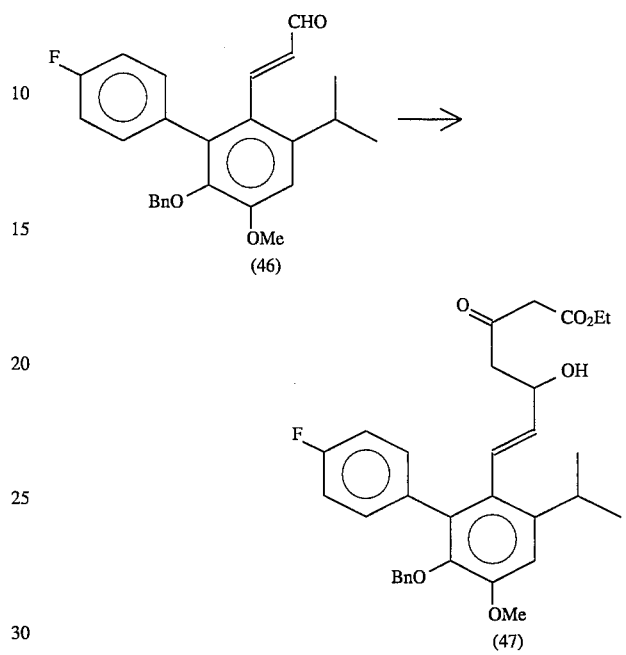

In a stream of argon, 7.94 g (62.3 mmol) of ethyl acetoacetate was added to a suspension prepared by dispersing 2.49 g (62.3 mmol) of sodium hydride (60%) in 80 ml of anhydrous THF, and the mixture was stirred for 35 minutes.

To this reaction mixture, 39.9 ml (62.3 mmol) of a 15% hexane solution of butyllithium was added, and the mixture was stirred for 30 minutes, and was then cooled to −78° C.

A THF solution of 19.4 g (47.9 mmol) of (E)-3-[6-benzyloxy- 4'-fluoro-5-methoxy-3-(propan-2-yl)biphenyl-2'-yl]-2-propenal (Compound (46)) synthesized in Reference Example 29, which was dissolved in 100 ml of anhydrous THF, was added dropwise to the above reaction mixture over a period of 25 minutes. After the dropwise addition of Compound 46, the reaction mixture was stirred for 2 hours.

The reaction mixture was added to 1N hydrochloric acid, and the mixture was then extracted with ethyl acetate. The extract layer was washed with water and then with a saturated aqueous solution of sodium chloride, dried over magnesium sulfate, and concentrated.

The residue was crystallized from a mixed solvent of ethyl acetate, hexane and dichloromethane, whereby ethyl (E)-7-[6-benzyloxy-4'-fluoro-5-methoxy-3-(propan-2-yl)biphenyl- 2-yl]-5-hydroxy-3-oxo-6-heptenoate (Compound (47)) was obtained in a yield of 2.97 g (11.6%).

The filtrate obtained in the crystallization was concentrated, chromatographed on silica gel and eluted with a mixed solvent of ethyl acetate and hexane (1:3), whereby Compound (47) was further obtained in a yield of 20.5 g (80.1%).

Melting point: 72.0°–73.0° C. (colorless needles, recrystallized from a mixed solvent of ethyl acetate, hexane, and dichloromethane)

¹HNMR (300 MHz, CDCl₃) δ1.23 (d, J=6.8 Hz, 3H), 1.24 (d, J=6.8 Hz, 3H), 1.28 (t, J=7.2 Hz, 3H), 2.32–2.48 (m, 2H), 3.21 (hept, J=6.8 Hz, 1H), 3.40 (s, 2H), 3.93 (s,3H), 4.20 (q, J=7.2 Hz, 2H), 4.44–4.52 (m, 1H), 4.64 (s, 2H), 5.15 (dd, J=16.1 and 6.2 Hz, 1H), 6.39 (dd, J=16.1 and 1.3 Hz, 1H), 6.88 (s, 1H), 6.93–7.01 (m, 2H), 7.01–7.09 (m, 2H), 7.10–7.17 (m, 2H), 7.17–7.26 (m, 3H)ppm.

IR (KBr): 3504, 2968, 2936, 1730, 1708, 1604 cm⁻¹.

Mass (m/z, %): 534 (M⁺, trace), 404 (26), 361 (100), 271 (28), 253 (19), 130 (13), 91 (74).

Reference Example 31

Ethyl (E)-7-[6-benzyloxy-4'-fluoro-5-methoxy-3-(propan-2-yl)biphenyl- 2-yl]-3,5-dihydroxy-6-heptenoate (Compound (48):

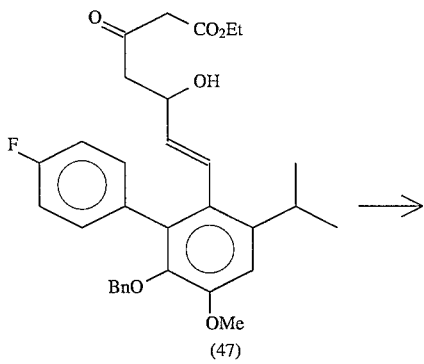

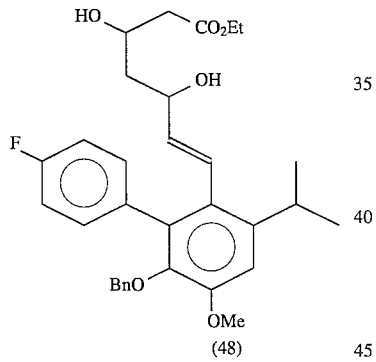

In an argon atmosphere, 56.6 ml (56.6 mmol) of a 1.0M tetrahydropyran solution of triethylborane was added to 222 mg (2.18 mmol) of pivalic acid was added, and the mixture was stirred at room temperature for 55 minutes.

To this mixture, 23.23 g (43.5 mmol) of ethyl (E)-7-[6-benzyloxy- 4'-fluoro-5-methoxy-3-(propan-2-yl)biphenyl-2-yl]- 5-hydroxy-3-oxo-6-heptenoate (Compound (47)) synthesized in Reference Example 30, with being dissolved in 150 ml of anhydrous THF, was added, and the mixture was stirred for 1 hour.

The reaction mixture was then cooled to −78° C., and 56.6 ml of methanol was added thereto. To this reaction mixture, 2.47 g (65.3 mmol) of sodium borohydride was added, with the entire amount being into several portions. The reaction mixture was then stirred for 1 hour and 20 minutes.

The reaction mixture was then gradually added to a mixed solution of 180 ml of a 30% aqueous solution of hydrogen peroxide and 180 ml of water at 0° C. The mixture was stirred overnight. The thus obtained reaction mixture was added to a saturated aqueous solution of ammonium chloride, and the mixture was then extracted with ethyl acetate.

The extract layer was successively washed with water, a saturated aqueous solution of sodium thiosulfate, water, and then a saturated aqueous solution of sodium chloride, dried over magnesium sulfate, and concentrated.

The residue was chromatographed on silica gel and eluted with a mixed solvent of ethyl acetate and hexane (1:1), whereby crude crystals were obtained. The thus obtained crude crystals were washed with hexane, whereby ethyl (E)-7-[6-benzyloxy-4'-fluoro-5-methoxy-3-(propan-2-yl)biphenyl- 2-yl]-3,5-dihydroxy-6-heptenoate (Compound (48)) was obtained in a yield of 20.6 g (88.4%).

The filtrate obtained when the crude crystals were washed with hexane, was concentrated, chromatographed on silica gel and eluted with a mixed solvent of ethyl acetate and hexane (1:1), whereby Compound (48) was also obtained in a yield of 960 mg (4.1%).

Melting point: 99.5°–100.5° C. (colorless fine particles, recrystallized from a mixed solvent of ethyl acetate and hexane)

¹HNMR (300 MHz, CDCl₃) δ1.23 (d, J=6.Hz, 3H), 1.24 (d, J=6.8 Hz, 3H), 1.29 (t, J=7.2 Hz, 3H), 1.15–1.30 (m, 1H), 1.33–1.50 (m, 1H), 2.35–2.47 (m, 2H), 2.74–2.77 (m, 1H), 3.24 (hept, J=6.8 Hz, 1H), 3.57–3.60 (m, 1H), 3.93 (s, 3H), 4.00–4.11 (m, 1H), 4.18 (q, J=7.2 Hz, 2H), 4.21–4.33 (m, 1H), 4.64 (s, 2H), 5.17 (dd, J=16.0 and 6.8 Hz, 1H), 6.36 (d, J=16.0 Hz, 1H), 6.89 (s, 1H), 6.91–7.06 (m, 4H), 7.10–7.17 (m, 2H), 7.18–7.24 (m, 3H)ppm.

IR (KBr): 3536, 3424, 2972, 1716, 1588 cm⁻¹.

Mass (m/z, %): 536 (M⁺,24), 518 (36), 500 (36), 402 (36), 269 (60), 91 (100).

Reference Example 32

Sodium (E)-7-[6-benzyloxy-4'-fluoro-5-methoxy-3-(propan-2-yl)biphenyl- 2-yl]-3,5-dihydroxy-6-heptenoate (Compound (49)):

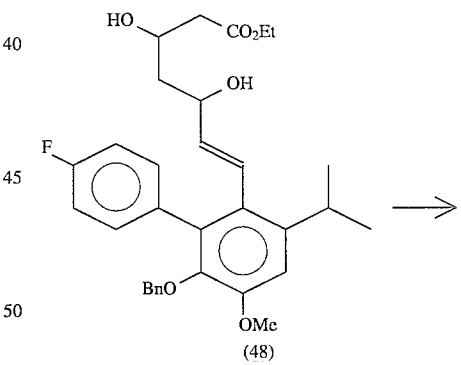

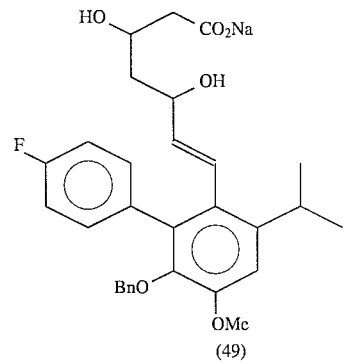

5.06 g (9.44 mmol) of ethyl (E)-7-[6-benzyloxy-4'-fluoro-5-methoxy-3-(propan-2-yl)biphenyl-2-yl]-3,5-dihydroxy-6-heptenoate (Compound (48)) synthesized in Reference Example 31 was dissolved in 50 ml of ethanol. To this solution, 4.72 ml (9.44 mmol) of a 2N aqueous solution of sodium hydroxide was added, and the mixture was stirred in an atmosphere of argon at room temperature for 1 hour and 30 minutes.

The reaction mixture was then concentrated, dissolved in water and subjected to freeze-drying, whereby sodium (E)-7-[6-benzyloxy-4'-fluoro-5-methoxy-3-(propan- 2-yl)biphenyl-2-yl]-3,5-dihydroxy-6-heptenoate (Compound (49)) was obtained in the form of a colorless amorphous solid in a yield of 4.82 g (96.3%).

$^1$HNMR (300 MHz, CD$_3$OD) δ1.25 (d, J=6.9 Hz, 3H), 1.15 (d, J=6.9 Hz, 3H), 1.20–1.40 (m, 1H), 1.45–1.61 (m, 1H), 2.17 (dd, J=15.4 and 7.9 Hz, 1H), 2.28 (dd, J=15.4 and 4.6 Hz, 1H), 3.37 (hept, J=6.9 Hz, 1H), 3.72–3.82 (m, 1H), 3.93 (s, 3H), 4.14–4.23 (m, 1H), 4.59–4.69 (m, 2H), 5.23 (dd, J=16.1 and 6.7 Hz, 1H), 6.32 (dd, J=16.1 and 1.0 Hz, 1H), 6.91–6.97 (m, 2H), 6.99 (s, 1H), 7.03–7.20 (m, 7H)ppm.

IR (KBr): 3416, 2964, 2872, 1580, 1512 cm$^{-1}$.

Mass (FAB-negative, m/z, %): 529 ([M–H]$^+$, trace), 507 (100).

Reference Example 33

5-Bromo-6-(4'-fluorophenyl)-2,3-dihydro-2,2'-dimethyl-4(propan- 2-yl)benzo[b]furan-7-carbaldehyde (Compound (51)):

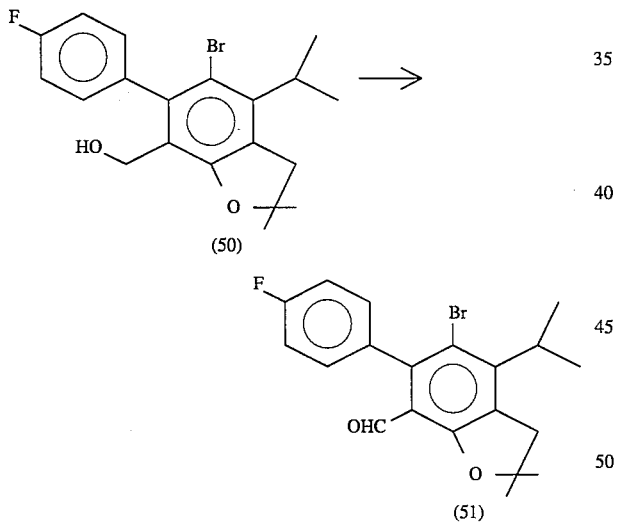

In an atmosphere of argon, 69 mg (0.176 mmol) of 5-bromo- 6-(4'-fluorophenyl)-2,3-dihydro-2,2-dimethyl-4-(propan- 2-yl)benzo[b]furan-7-methanol (Compound (50)) was dissolved in a mixed solvent of 1 ml of anhydrous THF and 3 ml of anhydrous DMSO, and 0.10 ml (0.70 mmol) of triethylamine and 97 mg (0.616 mmol) of a sulfur trioxide pyridine complex were successively added thereto.

This reaction mixture was stirred for 1 hour and 35 minutes, poured into 1N hydrochloric acid, and then extracted with ethyl acetate. The extract layer was successively washed with water, an aqueous solution of sodium hydrogencarbonate, and then with a saturated aqueous solution of sodium chloride, dried over magnesium sulfate, and concentrated.

The residue was crystallized from a mixed solvent of ethyl acetate and hexane, whereby 5-bromo-6-(4'-fluorophenyl)- 2,3-dihydro-2,2-dimethyl-4-(propan-2yl)benzo[b]furan- 7-carbaldehyde (Compound (51)) was obtained in a yield of 33 mg (48.0%).

The filtrate obtained in the crystallization was concentrated, chromatographed on silica gel and eluted with a mixed solvent of ethyl acetate and hexane (1:9), whereby Compound (51) was further obtained in a yield of 28 mg (40.7%).

Melting point: 136.0°–136.5° C. (colorless particles, recrystallized from a mixed solvent of ethyl acetate and hexane)

$^1$HNMR (300 MHz, CDCl$_3$) δ1.32 (d, J=7.1 Hz, 6H), 1.57 (s, 6H), 3.18 (s, 2H), 3.64–3.86 (m, 1H), 7.08–7.21 (m, 4H), 9.60 (s, 1H)ppm.

IR (KBr): 2976, 2932, 2876, 1694, 1604, 1580 cm$^{-1}$.

Mass (m/z, %): 392 (M$^+$, 100), 390 (M$^+$, 99), 377 (28), 375 (30), 296 (13), 268 (17), 253 (16), 196 (13), 183 (12), 149 (9).

EXAMPLE 13

5-Bromo-6-(4'-fluorophenyl)-2,3-dihydro-2,2-dimethyl-4-(propan- 2-yl)benzo[b]furan-7-ol (Compound (52)):

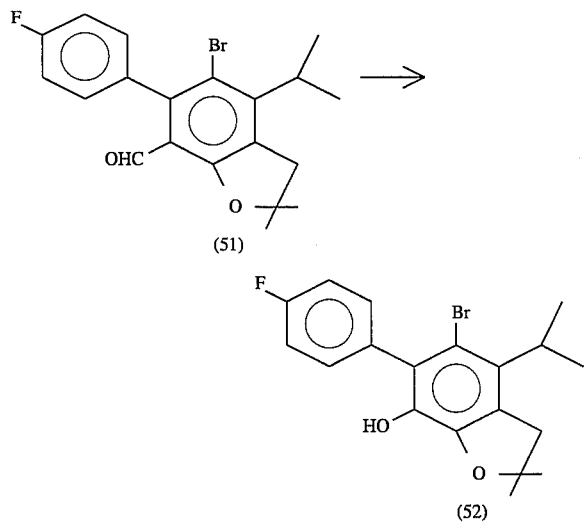

55 mg (0.141 mmol) of 5-bromo-6-(4'-fluorophenyl)-2,3-dihydro-2,2-dimethyl-4-(propan-2-yl)benzo[b]furan-7-carbaldehyde (Compound (51)) synthesized in Reference Example 33 was dissolved in 2 ml of 1,2-dichloroethane, and 42 mg (0.169 mmol) of m-chloroperbenzoic acid (70%) was added thereto.

This reaction mixture was stirred at room temperature for 35 minutes, and at room temperature for 7 hours and 30 minutes.

The reaction mixture was poured into water, and the mixture was extracted with ethyl acetate. The extract layer was successively washed with a diluted aqueous solution of sodium hydrogencarbonate, water, a saturated aqueous solution of sodium thiosulfate, water, and a saturated aqueous solution of sodium chloride, dried over magnesium sulfate, and concentrated.

The residue was dissolved in 3 ml of methanol, and 0.3 ml of a 28% ammonia water was added thereto. The mixture was stirred at room temperature for 1 hour.

This reaction mixture was poured into water, and the mixture was extracted with ethyl acetate. The extract layer was successively washed with 1N hydrochloric acid and a saturated aqueous solution of sodium chloride, dried over magnesium sulfate, and concentrated.

The residue was crystallized from hexane, whereby 5-bromo- 6-(4'-fluorophenyl)-2,3-dihydro-2,2-dimethyl-4-(propan- 2-yl)benzo[b]furan-7-ol (Compound (52)) was obtained in a yield of 21 mg (39.3%).

The filtrate obtained in the crystallization was concentrated, chromatographed on silica gel and eluted with a mixed solvent of hexane and dichloromethane (1:2), whereby Compound (52) was further obtained in a yield of 16 mg (29.9%).

Melting point: 158.0°–159.0° C. (colorless needles, recrystallized from a mixed solvent of ethyl acetate and hexane)

$^1$HNMR (300 MHz, CDCl$_3$) δ1.26 (d, J=7.2 Hz, 6H), 1.53 (s, 6H), 3.22 (s, 2H), 3.53–3.69 (m, 1H), 4.55 (s, 1H), 7.13–7.22 (m, 2H), 7.24–7.31 (m, 2H)ppm.

IR (KBr): 3484, 2972, 2932, 1628, 1602 cm$^{-1}$.

Mass (m/z, %): 380 (M$^+$, 100), 378 (M$^+$, 100), 365 (54), 363 (56), 284 (41), 256 (25), 242 (13), 183 (10), 149 (5).

EXAMPLE 14

7-Benzyloxy-5-bromo-6-(4-fluorophenyl)-2,3-dihydro-2,2-dimethyl- 4-(propan-2-yl)bezo[b]furan (Compound (53)):

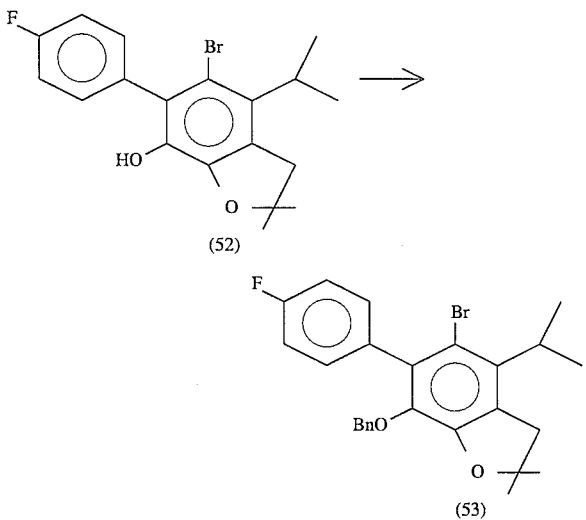

23 mg (0.061 mmol) of 5-bromo-6-(4'-fluorophenyl)-2,3-dihydro-2,2-dimethyl-4-(propan-2-yl)benzo[b]furan-7-ol (Compound (52)) synthesized in Example 13 was dissolved in 2 ml of DMF. To this solution, 0.01 ml (0.091 mmol) of benzyl bromide and 25 mg (0.183 mmol) of potassium carbonate were successively added.

This reaction mixture was stirred in an atmosphere of argon at room temperature for 4 hours and 30 minutes.

The reaction mixture was then poured into water, and the mixture was extracted with ethyl acetate. The extract layer was washed with water and a saturated aqueous solution of sodium chloride, dried over magnesium sulfate, and concentrated.

The residue was chromatographed on silica gel, eluted with a mixed solvent of hexane and ethyl acetate, and crystallized from a mixed solvent of ethyl acetate and hexane, whereby 7-benzyloxy-5-bromo-6-(4'-fluorophenyl)-2,3-dihydro-2,2-dimethyl-4-(propan-2-yl)bezo[b]furan (Compound (53)) was obtained in a yield of 19 mg (66.4%).

Melting point: 133.0°–133.5° C. (colorless particles, recrystallized from a mixed solvent of ethyl acetate and hexane)

$^1$HNMR (300 MHz, CDCl$_3$) δ1.28 (d, J=7.2 Hz, 6H), 1.54 (s, 6H), 3.19 (s, 2H), 3.55–3.73 (m, 1H), 4.82 (s, 2H), 6.94–7.02 (m, 2H), 7.02–7.16 (m, 4H), 7.18–7.25 (m, 3H)ppm.

IR (KBr): 2968, 2928, 2896, 1602 cm$^{-1}$.

Mass (m/z, %): 470 (M$^+$, 66), 468 (M$^+$, 65), 379 (19), 377 (18), 298 (100), 256 (82), 91 (67).

EXAMPLE 15

7-Benzyloxy-6-(4'-fluorophenyl)-2,3-dihydro-2,2-dimethyl-4-(propan- 2-yl)benzo[b]furan-5-carbaldehyde (Compound (54)):

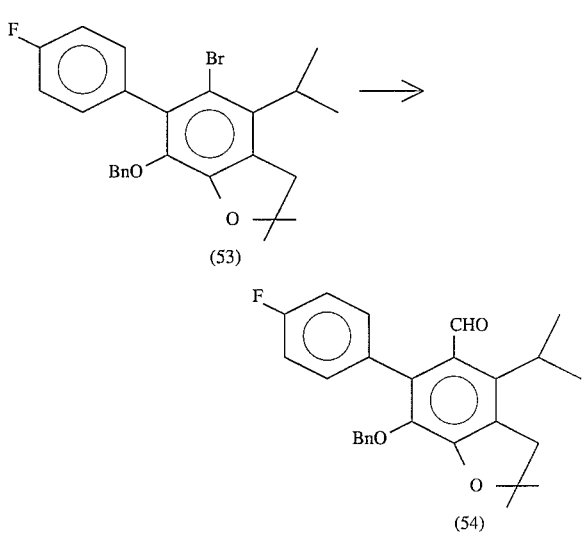

606 mg (24.9 mmol) of magnesium turnings was suspended in 5 ml of anhydrous THF. To this suspension, a solution of 0.54 ml (6.23 mmol) of 1,2-dibromoethane and 2.92 g (6.23 mmol) of 7-benzyloxy-5-bromo-6-(4'-fluorophenyl)- 2,3-dihydro-2,2-dimethyl-4-(propan-2-yl)bezo[b]furan (Compound (53)) synthesized in Example 14 in 10 ml of anhydrous THF was added dropwise at room temperature in a stream of argon over a period of 10 minutes.

This reaction mixture was stirred for 1 hour and 15 minutes, and 0.92 ml (7.48 mmol) of N-methylformanilide was added thereto. This reaction mixture was stirred for 2 hours and 50 minutes.

This reaction mixture was then poured into 1N hydrochloric acid, and the mixture was then extracted with ethyl acetate. The extract layer was successively washed with water, a saturated aqueous solution of sodium hydrogencarbonate, and a saturated aqueous solution of sodium chloride, dried over magnesium sulfate, and concentrated.

The residue was chromatographed on silica gel, eluted with a mixed solvent of ethyl acetate and hexane (1:6), and then concentrated.

The residue was again chromatographed on silica gel, and eluted with a mixed solvent of ethyl acetate and hexane (1:6), whereby 7-Benzyloxy-6-(4'-fluorophenyl)-2,3-dihydro-2,2-dimethyl-4-(propan- 2-yl)benzo[b]furan-5-carbaldehyde (Compound (54)) was obtained in a yield of 1.81 g (69.4%).

Melting point: 158.0°–159.0° C. (colorless particles, recrystallized from a mixed solvent of ethyl acetate and hexane)

¹HNMR (300 MHz, CDCl₃) δ1.28 (d, J=7.1Hz, 6H), 1.57 (s, 6H), 3.21 (s, 2H), 4.09 (hept, J=7.1 Hz, 1H), 4.81 (s, 2H), 6.94–7.01 (m, 2H), 7.01–7.10 (m, 2H), 7.10–7.25 (m, 5H)ppm IR (KBr): 2968, 2932, 2872, 1680, 1592 cm⁻¹.

Mass (m/z, %): 418 (M⁺, 100), 327 (93), 309 (33), 267 (18), 149 (43), 91 (78).

Reference Example 34

(E)-3-[7-benzyloxy-6-(4'-fluorophenyl)-2,3-dihydro-2,2-dimethyl- 4-(propan-2-yl)benzo[b]furan-5-yl]-2-propenenitrile (Compound (55)):

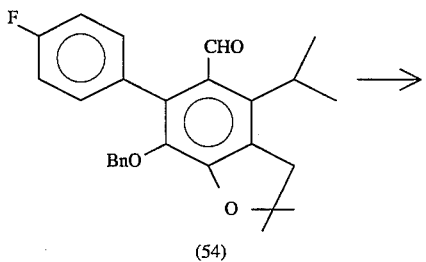

(54)

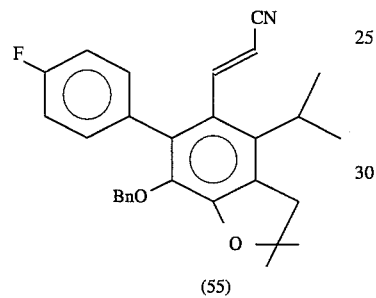

(55)

104 mg (2.61 mmol) of sodium hydride (60%) was suspended in 10 ml of anhydrous THF. To this suspension, at 0° C., 0.42 ml (2.61 mmol) of diethyl cyanomethyl phosphonate was added, and 1.04 g (2.49 mmol) of 7-benzyloxy- 6-(4'-fluorophenyl)-2,3-dihydro-2,2-dimethyl-4-(propan- 2-yl)benzo[b]furan-5-carbaldehyde (Compound (54)) synthesized in Example 15, which was dissolved in 5 ml of anhydrous THF, was then added and dissolved therein.

This mixture was stirred in an atmosphere of argon for 30 minutes and was then added to a 1N solution of hydrochloric acid.

This mixture was then extracted with ethyl acetate. The extract layer was successively washed with water, a saturated aqueous solution of sodium hydrogencarbonate, water, and then a saturated aqueous solution of sodium chloride, dried over magnesium sulfate, and concentrated.

The residue was crystallized from hexane, whereby (E)-3-[7-benzyloxy-6-(4'-fluorophenyl)-2,3-dihydro-2,2-dimethyl- 4-(propan-2-yl)benzo[b]furan-5-yl]-2-propenenitrile (Compound (55)) was obtained in a yield of 887 mg (80.8%).

The filtrate obtained in the crystallization was concentrated and chromatographed on silica gel and eluted with a mixed solvent of ethyl acetate and hexane (1:6), whereby Compound (55) was further obtained in a yield of 73 mg (6.6%).

Melting point: 162.0°–163.0° C. (colorless, fine particles, recrystallized from hexane)

¹HNMR (300 MHz, CDCl₃) δ1.27 (d, J=7.1 Hz, 6H), 1.55 (s, 6H), 3.17 (s, 2H), 3.21 (hept, J=7.1 Hz, 1H), 4.80 (s, 2H), 4.86 (d, J=16.9 Hz, 1H), 6.93–7.00 (m, 2H), 7.00–7.06 (m, 4H), 7.14–7.24 (m, 3H), 7.29 (d, J=16.9 Hz, 1H)ppm.

IR (KBr)m 2972, 2936, 1216, 1616 cm⁻¹.

Mass (m/z, %): 441 (M⁺, 350 (36), 308 (100), 291 (19), 91 (60).

Reference Example 35

(E)-3-[7-benzyloxy-6-(4'-fluorophenyl)-2,3-dihydro-2,2-dimethyl- 4-(propan-2-yl)benzo[b]furan-5-yl]-2-propenal (Compound (56)):

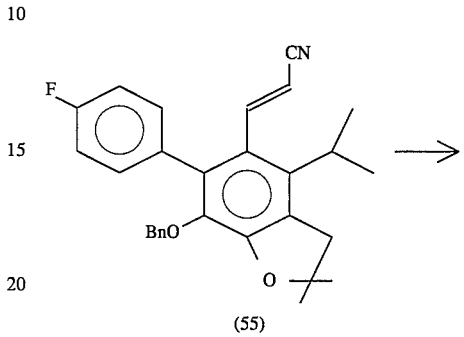

(55)

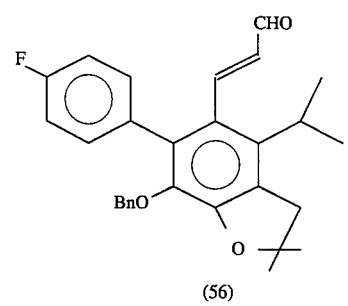

(56)

953 mg (2.16 mmol) of (E)-3-[7-benzyloxy-6-(4'-fluorophenyl)- 2,3-dihydro-2,2-dimethyl-4-(propan-2-yl)benzo [b]furan- 5-yl]-2-propenenitrile (Compound (55)) synthesized in Reference Example 34 was dissolved in 25 ml of anhydrous toluene. To this solution, 1.35 ml (2.38 mmol) of a 25% hexane solution of diisobutylaluminum hydride was added at −78° C.

This mixture was then stirred in an atmosphere of argon for 1 hour and 30 minutes, and was then added to a 1N hydrochloric acid. This mixture was stirred, with the addition of ethyl acetate thereto, at room temperature overnight.

The ethyl acetate layer of the mixture was separated and successively washed with a 1N hydrochloric acid, a saturated aqueous solution of sodium hydrogencarbonate, and a saturated aqueous solution of sodium chloride, dried over magnesium sulfate, and concentrated.

The residue was chromatographed on silica gel and eluted with a mixed solvent of dichloromethane and hexane (2:1), whereby (E)-3-[7-benzyloxy-6-(4'-fluorophenyl)- 2,3-dihydro-2,2-dimethyl-4-(propan-2-yl)benzo[b]furan-5-yl]-2-propenal (Compound (56)) was obtained in a yield of mg (78.5%).

Melting point: 142.0°–143.5° C. (colorless, fine particles, recrystallized from a mixed solvent of ethyl acetate and hexane)

¹HNMR (300 MHz, CDCl₃) δ1.28 (d, J=7.1 Hz, 6H), 1.57 (s, 6H), 3.21 (s, 2H), 3.33 (hept, J=7.1 Hz, 1H), 4.82 (s, 2H), 5.85 (dd, J=16.2 and 7.8 Hz, 1H), 6.93–7.08 (m, 6H), 7.17–7.24 (m, 3H), 7.29 (d, J=16.2 Hz, 1H), 9.34 (d, J=7.8 Hz, 1H)ppm.

IR (KBr): 2976, 2936, 1674, 1622 cm⁻¹.

Mass (m/z, %): 444 (M⁺, 30), 401 (100), 353 (18), 311 (34), 293 (21), 267 (15), 91 (41).

Reference Example 36

Ethyl (E)-7-[7-benzyloxy-6-(4'-fluorophenyl)-2,3-dihydro-2,2-dimethyl-4-(propan-2-yl)benzo[b]furan-5-yl]-5-hydroxy-3-oxo-6-heptenoate (Compound (57)):

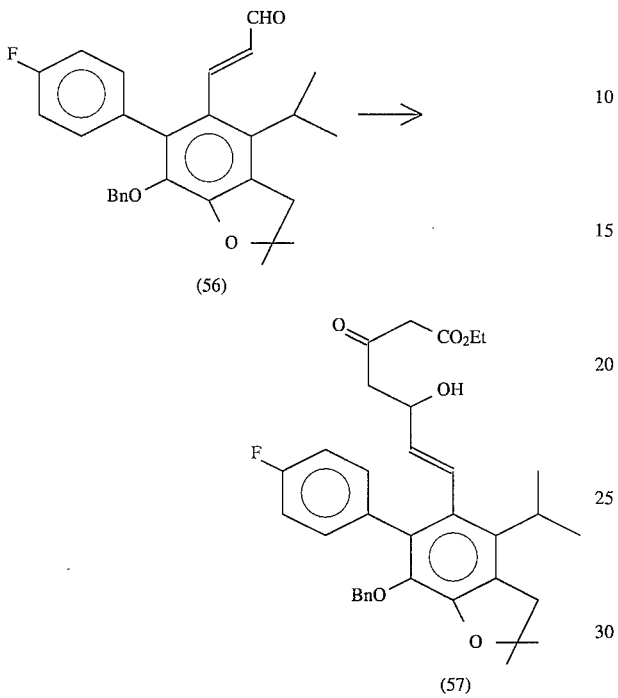

115 mg (2.88 mmol) of sodium hydride (60%) was suspended in 3 ml of anhydrous THF. To this solution, 0.367 ml (2.88 mmol) of ethyl acetoacetate was added in a stream of argon at 0° C. This reaction mixture was stirred for 40 minutes. with the addition of 1.84 ml (2.88 mmol) of a 15% hexane solution of butyllithium thereto, the reaction mixture was further stirred for 40 minutes, and was then cooled to −78° C.

To this reaction mixture, 852 mg (1.92 mmol) of (E)-3-[7-benzyloxy-6-(4'-fluorophenyl)-2,3-dihydro-2,2-dimethyl-4-(propan-2-yl)benzo[b]furan-5-yl]-2-propenal (Compound (56)) synthesized in Reference Example 35, which was dissolved in 5 ml of anhydrous THF, was added.

This mixture was then stirred for 50 minutes and was added to a 1N hydrochloric acid.

This mixture was then extracted with ethyl acetate. The extract layer was successively washed with a saturated aqueous solution of sodium hydrogencarbonate, and then with a saturated aqueous solution of sodium chloride, dried over magnesium sulfate, and concentrated.

The residue was chromatographed on silica gel and eluted with a mixed solvent of ethyl acetate and hexane (1:3), whereby ethyl (E)-7-[7-benzyloxy-6-(4'-fluorophenyl)- 2,3-dihydro-2,2-dimethyl-4-(propan-2-yl)benzo[b]furan- 5-yl]-5-hydroxy-3-oxo-6-heptenoate (Compound (57)) was obtained in a yield of 978 mg (88.7%).

Melting point: 99.5°–101.0° C. (colorless particles, recrystallized from hexane)

$^1$HNMR (300 MHz, CDCl$_3$) δ1.22 (d, J=7.1 Hz, 3H), 1.23 (d, J=7.1 Hz, 3H), 1.28 (t, J=7.2 Hz, 3H), 1.54 (s, 6H), 2.25–2.42 (m, 2H), 3.16 (s, 2H), 3.24 (hept, J=7.1 Hz, 1H), 3.38 (s, 2H), 4.20 (q, J=7.2 Hz, 2H), 4.40–4.50 (m, 1H), 4.81 (s, 2H), 5.08 (dd, J=16.0 and 6.4 Hz, 1H), 6.36 (dd, J=16.0 and 1.2 Hz, 1H), 6.94–7.07 (m, 6H), 7.17–7.23 (m, 3H)ppm.

IR (KBr): 3492, 2976, 2936, 1734, 1716, 1602 cm$^{-1}$.
Mass (m/z, %): 574 (M$^+$, 9), 556 (6), 401 (100), 311 (25), 293 (16), 267 (10), 91 (28).

Reference Example 37

Ethyl (E)-7-[7-benzyloxy-6-(4'-fluorophenyl)-2,3-dihydro-2,2-dimethyl-4-(propan-2-yl)benzo[b]furan-5-yl]-3,5-dihydroxy-6-heptenoate (Compound (58)):

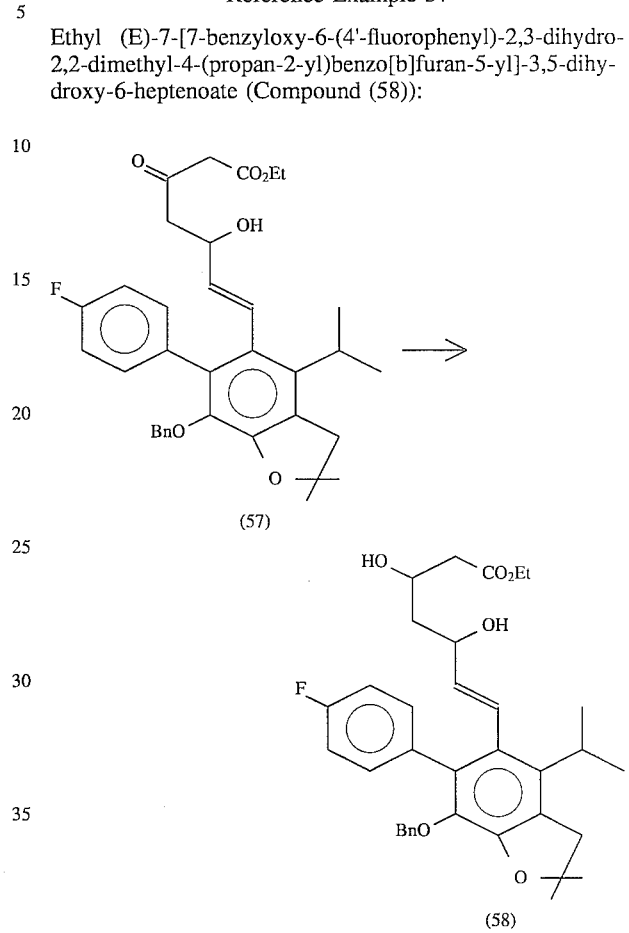

1.99 ml (1.99 mmol) of a 1.0M THF solution of triethylborane was added to 17 mg (0.167 mmol) of pivalic acid. This mixture was stirred in an atmosphere of argon at room temperature for 1 hour.

To this mixture, 924 mg (1.61 mmol) of ethyl (E)-7-[7-benzyloxy- 6-(4'-fluorophenyl)-2,3-dihydro-2,2-dimethyl-4-(propan-2-yl)benzo[b]furan-5-yl]-5-hydroxy-3-oxo-6-heptenoate (Compound (57)) synthesized in Reference Example 36, which was dissolved in 10 ml of anhydrous THF, was added, and the mixture was stirred for 55 minutes. This reaction mixture was then cooled to −78° C., and 2.5 ml of methanol, and then 94 mg (2.49 mmol) of sodium borohydride were added thereto.

This mixture was stirred for 1 hour and 45 minutes, and poured into a solution of 7.0 ml of a 30% hydrogen peroxide, and 14 ml of water at 0° C.

This mixture was then extracted with ethyl acetate. The extract layer was successively washed with water, a saturated aqueous solution of sodium thiosulfate, and then with a saturated aqueous solution of sodium chloride, dried over magnesium sulfate, and concentrated.

The residue was chromatographed on silica gel and eluted with a mixed solvent of ethyl acetate and hexane (1:1), whereby ethyl (E)-7-[7-benzyloxy-6-(4'-fluorophenyl)- 2,3-dihydro-2,2-dimethyl-4-(propan-2-yl)benzo[b]furan- 5-yl]-3,5-dihydroxy-6-heptenoate (Compound (58)) was obtained in a yield of 859 mg (89.8%).

Melting point: 120.5°–121.5° C. (colorless particles, recrystallized from a mixed solvent of ethyl acetate and hexane)

$^1$HNMR (300 MHz, CDCl$_3$) δ1.22 (d, J=7.1 Hz, 3H), 1.23 (d, J=7.1 Hz, 3H), 1.10–1.43 (m, 2H), 1.28 (t, J=7.2 Hz, 1H), 1.54 (s, 6H), 2.30–2.46 (m, 2H), 2.65 (s with fine coupling, 1H), 3.16 (s, 2H), 3.28 (hept, J=7.1 Hz, 1H), 3.57 (s with fine coupling, 1H), 3.98–4.10 (m, 1H), 4.18 (q, J=7.2 Hz, 2H), 4.18–4.30 (m, 1H), 4.81 (s, 2H), 5.10 (dd, J=16.0 and 6.6 Hz, 1H), 6.33 (dd, J=16.0 and 1.0 Hz, 1H), 6.90–7.08 (m, 6H), 7.16–7.24 (m, 3H)ppm.

IR (KBr): 3456, 2976, 2936, 1730, 1604 cm$^{-1}$.

Mass (m/z, %): 576 (M$^+$, 100), 558 (61), 485 (23), 467 (27), 442 (33), 311 (67), 269 (25), 91 (42).

Reference Example 38

Sodium (E)-7-[7-benzyloxy-6-(4'-fluorophenyl)-2,3-dihydro- 2,2-dimethyl-4-(propan-2-yl)benzo[b]furan-5-yl]- 3,5-dihydroxy-6-heptenoate (Compound (59)):

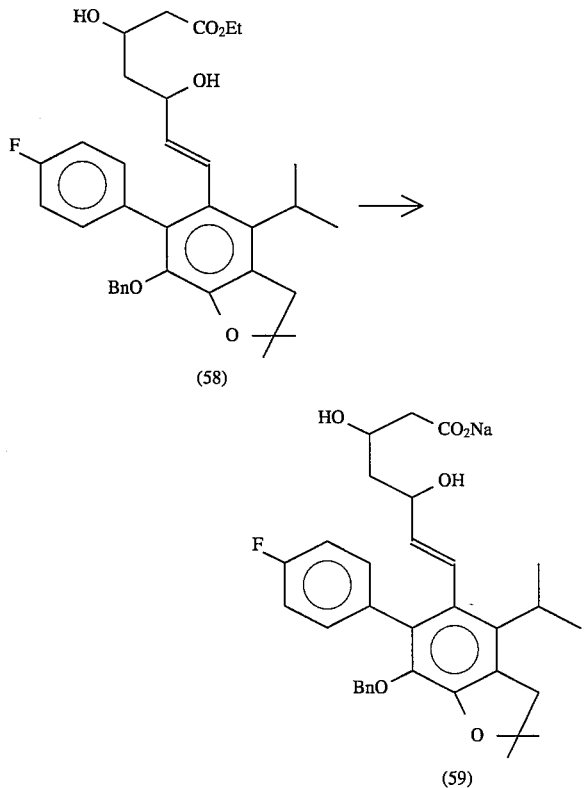

53 mg (0.092 mmol) of ethyl (E)-7-[7-benzyloxy-6- (4'-fluorophenyl)-2,3-dihydro-2,2-dimethyl-4-(propan-2-yl) benzo[b]furan- 5-yl]-3,5-dihydroxy-6-heptenoate (Compound (58)) synthesized in Reference Example 37 was dissolved in 1 ml of ethanol. To this solution, 0.092 ml (0.092 mmol) of a 1N aqueous solution of sodium hydroxide was added, and the mixture was stirred in an atmosphere of argon at room temperature for 1 hour and 50 minutes.

The reaction mixture was then concentrated, dissolved in water and subjected to freeze-drying, whereby sodium (E)-7-[7-benzyloxy-6-(4'-fluorophenyl)- 2,3-dihydro-2,2-dimethyl-4-(propan-2-yl)benzo[b]furan-5-yl]- 3,5-dihydroxy-6-heptenoate (Compound (59)) was obtained in the form of a colorless, amorphous solid in a quantitative yield.

$^1$HNMR (300 MHz, CD$_3$OD) δ1.17–1.38 (m, 1H), 1.25 (d, J=7.2 Hz, 6H), 1.42–1.53 (m, 1H), 1.53 (s, 6H), 2.15 (dd, J=15.4 and 7.8 Hz, 1H), 2.27 (dd, J=15.4 and 4.4 Hz, 1H), 3.21 (s, 2H), 3.43 (hept, J=7.2 Hz, 1H), 3.68–3.80 (m, 1H), 4.10–4.19 (m, 1H), 4.77 (s, 2H), 5.16 (dd, J=16.0 and 6.6 Hz, 1H), 6.29 (d with fine coupling, J=16.0 Hz, 1H), 6.94–7.10 (m, 6H), 7.14–7.24 (m, 3H)ppm.

IR (KBr): 3448, 2976, 1580, 1514 cm$^{-1}$.

Mass (FAB-negative, m/z, %): 569 ([M–H]$^-$, 8), 547 (100).

EXAMPLE 16

2-chloromethyl-4'-fluoro-5,6-dimethoxy-3-(propan-2 -yl)biphenyl (Compound (60)):

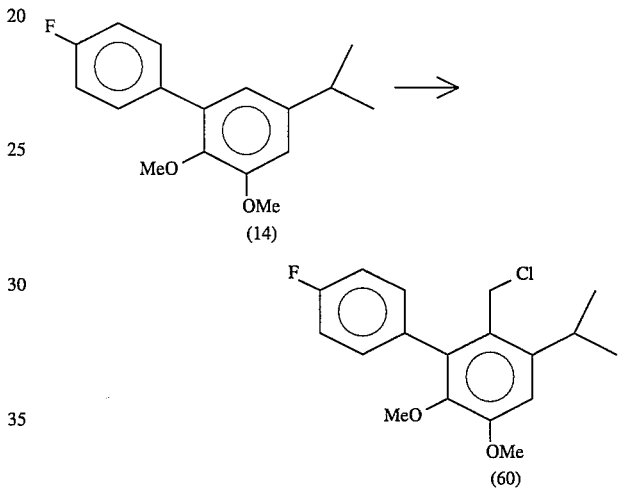

5.48 g (20.0 mmol) of 4'-fluoro-2,3-dimethoxy-5 -(propan-2-yl)biphenyl (Compound (14)) synthesized in Example 2 was dissolved in a mixture of 20 ml of concentrated hydrochloric acid and 30 ml of 1,4-dioxane.

To this solution, 1.2 g (36.0 mmol) of paraformaldehyde (90%) and 545 mg (4 mmol) of zinc chloride were added, and the mixture was refluxed for 5 hours.

The reaction mixture was then poured into water, and the mixture was extracted with toluene. The extract layer was successively washed with water and a saturated aqueous solution of sodium chloride, dried over magnesium sulfate, and concentrated, whereby crude 2-chloromethyl-4'-fluoro-5,6-dimethoxy-3-(propan-2-yl)biphenyl (Compound (60)) was obtained in a quantitative yield.

Melting point: 105.0°–106.0° C. (colorless columns, recrystallized from a mixed solvent of ethyl acetate and hexane)

$^1$HNMR (300 MHz, CDCl$_3$) δ1.32 (d, J=6.8 Hz, 6H), 3.35 (hept, J=6.8 Hz, 1H), 3.48 (s, 3H), 3.92 (s, 3H), 4.35 (s, 2H), 6.90 (s, 1H), 7.08–7.18 (m, 2H), 7.29–7.37 (m, 2H)ppm.

IR (KBr): 2972, 2936, 1606, 1584 cm$^{-1}$.

Mass (m/z, %): 324 (M$^+$, 34), 322 (M$^+$, 100), 287 (30), 286 (75), 273 (23), 272 (72), 271 (35), 257 (23), 245 (93), 230 (55).

EXAMPLE 17

4'-fluoro-5,6-dimethoxy-3-(propan-2-yl)biphenyl-2-carbaldehyde (Compound (30)) and 4'-fluoro-5,6-dimethoxy-3-(propan-2-yl)biphenyl-2-methanol (Compound (61)):

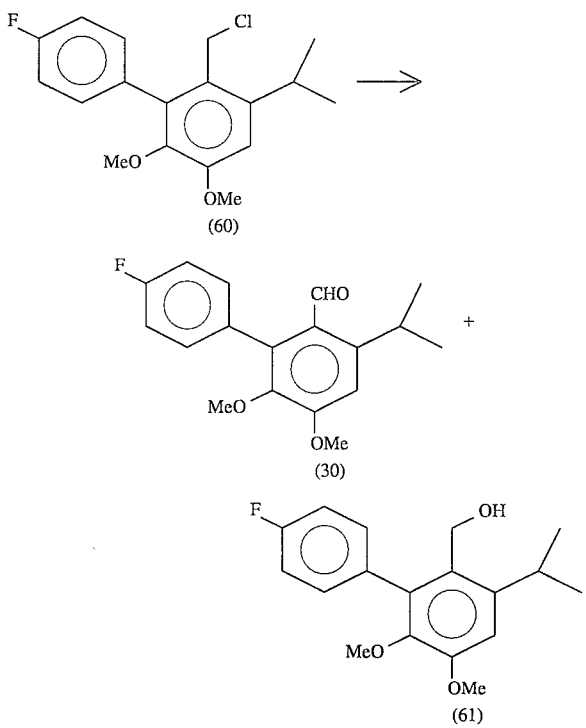

6.59 g of crude 2-chloromethyl-4'-fluoro-5,6-dimethoxy-3-(propan-2-yl)biphenyl (Compound (60)) synthesized in Example 16 and 3.36 g (40.0 mmol) of sodium hydrogencarbonate were added to 21.5 ml of anhydrous DMSO. The mixture was heated to 120° C. for 2 hours in an atmosphere of argon.

This reaction mixture was then poured into water, and the mixture was extracted with ethyl acetate. The extract layer was successively washed with water and a saturated aqueous solution of sodium chloride, dried over magnesium sulfate, and concentrated.

The residue was chromatographed on silica gel, and eluted with a mixed solvent of hexane and ethyl acetate (6:1), whereby 4'-fluoro-5,6-dimethoxy-3-(propan-2-yl)biphenyl-2-carbaldehyde (Compound (30)) was obtained in a yield of 4.40 g (73.5%), and 4'-fluoro-5,6-dimethoxy-3-(propan-2-yl)biphenyl-2-methanol (Compound (61)) was obtained in a yield of 1.06 g (17.5%).

The analysis data of the thus obtained Compound (30) was the same as that of Compound (30) obtained in Example 10.

Compound (61)

Melting point: 106.5°–108.0° C. (colorless needles, recrystallized from a mixed solvent of ethyl acetate and hexane)

$^1$HNMR (300 MHz, CDCl$_3$) δ1.31 (d, J=6.9 Hz, 6H), 3.40 (hept, J=6.9 Hz, 1H), 3.48 (s, 3H), 3.92 (S, 3H), 4.37 (s, 2H), 6.91 (s, 1H), 7.06–7.16 (m, 2H), 7.24–7.34 (m, 2H)ppm.

IR (KBr): 3440, 2968, 2940, 1606, 1586 cm$^{-1}$.

Mass (m/z, %): 304 (M$^+$, 100), 286 (64), 271 (38), 245 (21), 230 (28).

EXAMPLE 18

4'-fluoro-5,6-dimethoxy-3-(propan-2-yl)biphenyl-2-carbaldehyde (Compound (30)):

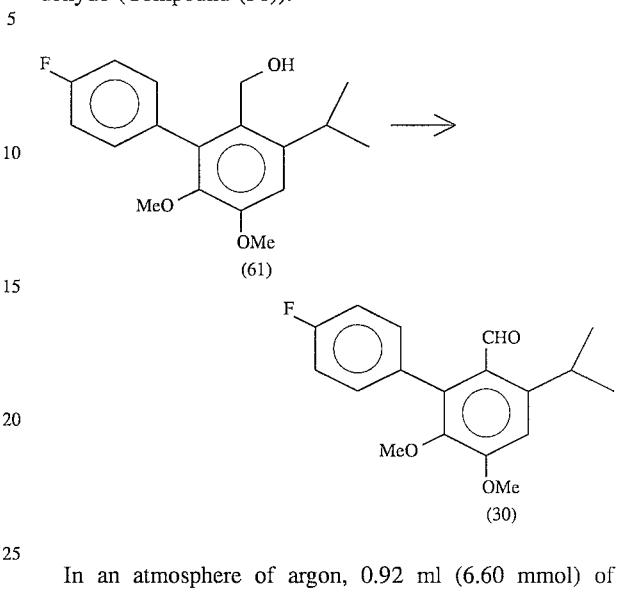

In an atmosphere of argon, 0.92 ml (6.60 mmol) of triethylamine and 785 mg (4.93 mmol) of a sulfur trioxide pyridine complex were successively added, with stirring, to a solution of 500 mg (1.64 mmol) of 4'-fluoro-5,6-dimethoxy-3-(propan-2-yl)biphenyl-2-methanol (Compound (61)) synthesized in Example 17 in 5 ml of anhydrous DMSO, and the mixture was stirred at room temperature for 1 hour.

The reaction mixture was then poured into diluted hydrochloric acid, and the mixture was extracted with ethyl acetate. The extract layer was washed with a saturated aqueous solution of sodium chloride, dried over magnesium sulfate, and concentrated.

The residue was chromatographed on silica gel and eluted with a mixed solvent of dichloromethane and hexane (2:1), whereby 4'-fluoro-5,6-dimethoxy-3-(propan-2-yl)-biphenyl-2-carbaldehyde (Compound (30)) was obtained in a yield of 380 mg (76.5%).

The analysis data of the thus obtained Compound (30) was the same as that of Compound (30) obtained in Example 10.

EXAMPLE 19

5-chloro-4'-fluoro-6-hydroxy-3-(propan-2-yl)biphenyl-2-carbaldehyde (Compound (63)):

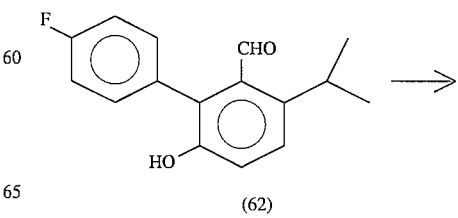

73

[Structure (63): biphenyl with F, CHO, isopropyl, HO, Cl substituents]

0.35 ml (4.36 mmol) of sulfuryl chloride was added to a solution of 862 mg (3.34 mmol) of 4'-fluoro-2-formyl-3-(propan-2-yl)biphenyl-6-ol (Compound (62)) in 10 ml of dichloromethane, and the mixture was refluxed [or 2 hours and 20 minutes.

The reaction mixture was then poured into a saturated aqueous solution of sodium hydrogencarbonate, and the mixture was extracted with ethyl acetate. The extract layer was washed with a saturated aqueous solution of sodium chloride, dried over magnesium sulfate, and concentrated.

The residue was chromatographed on silica gel and eluted with a mixed solvent o[hexane and dichloromethane (1:1), whereby 5-chloro-4'-fluoro-6-hydroxy-3-(propan-2-yl)biphenyl-2-carbaldehyde (Compound (63)) was obtained in a yield of 412 mg (42.2%).

Melting point 140°–141° C. (colorless plates, recrystallized from a mixed solvent of hexane and dichloromethane)

$^1$HNMR (300 MHz, CDCl$_3$) δ1.25 (d, J=6.8 Hz, 6H), 3.79 (hept, J=6.8 Hz, 1H), 5.42 (s, 1H), 7.14–7.23 (m, 2H), 7.26–7.34 (m, 2H), 7.44 (s, 1H), 9.74 (s, 1H)ppm.

IR (KBr): 3292, 2972, 2876, 2780, 1682, 1514 cm$^{-1}$.

EXAMPLE 20

5-chloro-4'-fluoro-6-methoxy-3-(propan-2-yl)biphenyl-2-carbaldehyde (Compound (64)):

[Structure (63) → Structure (64) with MeO and OMe groups]

In an atmosphere of argon, 0.2 ml (3.21 mmol) of methyl iodide was added with stirring to a solution of a mixture of 536 mg (1.83 mmol) of 5-chloro-4'-fluoro-6-hydroxy-3-(propan-2-yl)biphenyl-2-carbaldehyde (Compound (63)) synthesized in Example 19 and 303 mg (2.2 mmol) of potassium carbonate in 6 ml of DMF, and the mixture was stirred for 40 minutes.

74

The reaction mixture was then poured into a saturated aqueous solution of ammonium chloride, and the mixture was extracted with ethyl acetate. The extract layer was washed with a saturated aqueous solution of sodium chloride, dried over magnesium sulfate, and concentrated.

The residue was chromatographed on silica gel and eluted with a mixed solvent of hexane and ethyl acetate (8:1), whereby 5-chloro-4'-fluoro-6-methoxy-3-(propan-2-yl)biphenyl-2-carbaldehyde (Compound (64)) was obtained in a yield of 542 mg (96.6%).

Melting point: 120°–122° C. (colorless particles, recrystallized from hexane)

$^1$HNMR (300 MHz, CDCl$_3$) δ1.26 (d, J=6.8 Hz, 6H), 3.45 (s, 3H), 3.81 (hept, J=6.8 Hz, 1H), 7.11–7.20 (m, 2H), 7.26–7.35 (m, 2H), 7.48 (s, 1H), 9.71 (s, 1H)ppm.

IR (KBr): 2972, 2944, 2876, 2780, 1694, 1512 cm$^{-1}$.

Mass (m/z, %): 308 (M$^+$, 35), 306 (M$^+$, 100), 293 (10), 291 (29), 277 (16), 276 (12), 275 (12), 273 (14), 271 (16).

Reference Example 39

[Determination of Inhibition of Sterol Synthesis]

Sodium (E)-7-[4'-fluoro-5,6-dimethoxy-3-(propan-2-yl) biphenyl-2-yl]-3,5-dihydroxy-6-heptenoate (Compound (19)) (0.3 mg/5 ml/kg) suspended in a 5% arabic gum solution was orally given to SD rats weighing 150 to 200 g. 5 hours later, $^{14}$C-acetic acid (100 μCi/kg) was intraperitoneally injected, and furthermore one hour later, liver was removed to determine the inhibitory activity of Compound (19) on the biosynthesis of sterol in accordance with the method described in European Journal of Biochemistry (Eur. J. Biochem.) Vol. 77, page 31 (1977).

The results are shown in Table 1 in comparison with pravastatin (Comparative Example 1) and simvastatin (Comparative Example 2).

TABLE 1

| Ref. Ex. | Comp. No. | Compound | Dose (mg/kg) | Inhibition of Sterol Synthesis (%) |
|---|---|---|---|---|
| 10 | 19 | Sodium (E)-7-[4'-fluoro-5,6-dimethoxy-3-(propan-2-yl)biphenyl-2-yl]-3,5-dihydroxy-6-heptenoate | 0.3 | 73 |
| Comp. Ex. 1 | | Pravastatin | 1 | 16 |
| | | | 0.3 | — |
| Comp. Ex. 2 | | Simvastatin | 1 | 41 |
| | | | 0.3 | 1 |

What is claimed is:

1. A method of producing a carboxylic acid ester derivative of formula (II),

[Structure (II): R$^4$-CH=CH-CH(OR$^1$)-CH$_2$-CH(OR$^2$)-CH$_2$-CO$_2$R$^3$]

wherein R$^1$ and R$^2$ are independently a protective group for hydroxyl group, or R$^1$ and R$^2$ integrally constitute a protective group for hydroxyl groups; R$^3$ is an alkyl group having 1 to 12 carbon atoms, or an aryl group; and R$^4$ is a substituted aryl group, a substituted heterocyclic group, a substituted vinyl group, or a substituted cycloalkenyl group, comprising the steps of:

allowing a heptanoate derivative of formula (III),

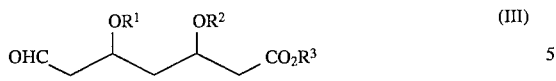

wherein $R^1$, $R^2$ and $R^3$ are respectively the same as defined in formula (II), to react with an organometallic reagent derived from a halogenated compound having formula (IV),

wherein $R^4$ is the same as defined in formula (II), and $X^1$ is a halogen atom, to obtain a carboxylic acid ester derivative of formula (I),

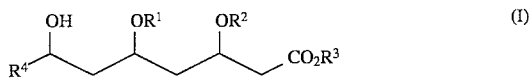

wherein $R^1$, $R^2$, $R^3$ and $R^4$ are respectively the same as defined in formula (II), and subjecting said carboxylic acid ester derivative of formula (I) to a dehydration reaction.

2. The method as claimed in claim 1, wherein said organometallic reagent comprises a metal component selected from the group consisting of an alkali metal and an alkaline earth metal.

3. The method as claimed in claim 2, wherein said organometallic reagent is an organic lithium compound.

4. The method as claimed in claim 2, wherein said organometallic reagent is an organic magnesium halide compound.

5. The method as claimed in claim 1, wherein said dehydration reaction is carried out in the presence of an agent selected from the group consisting of a halogenating agent, a sulfonating agent and an esterification agent.

6. The method as claimed in claim 1, wherein said dehydration reaction is carried out in the presence of a halogenating agent and a base.

7. The method as claimed in claim 1, wherein said protective group for hydroxyl group, represented by $R^1$ or $R^2$, is selected from the group consisting of an alkyl group having 1 to 6 carbon atoms, an alkenyl group having 2 to 6 carbon atoms, a heterocyclic group, a substituted silyl group, an acyl group, a substituted oxycarbonyl group, and a substituted carbamoyl group; and said protective group for hydroxyl groups, formed by $R^1$ and $R^2$ together, is selected from the group consisting of methylene group, an alkylidene group having 2 to 10 carbon atoms and carbonyl group.

8. The method as claimed in claim 7, wherein said protective group for hydroxyl group, represented by $R^1$ or $R^2$, is a substituted silyl group.

9. The method as claimed in claim 7, wherein said protective group for hydroxyl groups, formed by $R^1$ and $R^2$ together, is an alkylidene group having 2 to 10 carbon atoms.

10. The method as claimed in claim 9, wherein said alkylidene group is selected from the group consisting of isopropylidene group and cyclohexylidene group.

11. The method as claimed in claim 1, wherein said alkyl group represented by $R^3$ is selected from the group consisting of methyl group, ethyl group, n-propyl group, isopropyl group, n-butyl group, sec-butyl group, and t-butyl group.

* * * * *

UNITED STATES PATENT AND TRADEMARK OFFICE
CERTIFICATE OF CORRECTION

PATENT NO. : 5,481,009

DATED : JANUARY 2, 1996

INVENTOR(S) : MASAKATSU MATSUMOTO ET AL

It is certified that error appears in the above-identified patent and that said Letters Patent is hereby corrected as shown below:

```
Column 2, line 23, "Witrig" should read --Wittig--;
          line 45, "utilising" should read --utilizing--.
Column 3, line 37, "scheme" should read --scheme:--;
          line 64, "eater" should read --ester--.
Column 4, line 11, "R³" should read --R¹--.
Column 6, line 57, "1 to carbon atoms" should read --1 to 6
                   carbon atoms--.
Column 7, line 5, "R³ should read --R⁵--;
          line 13, "R³" should read --R⁵--;
          line 17, "R³ " should read --R⁵--;
          line 28, "R³" should read --R⁵--.
Column 8, line 5, "rang" should read --ring--;
          line 7, "carbon which" should read --carbon atoms
                   which--.
Column 10, line 21, "agent such anhydrous" should read --agent
                    such as anhydrous--.
Column 11, line 44, "1et" should read --1st--.
Column 12, line 25, "R³" should read --R⁵--;
           line 39, "R¹" should read --R⁵--;
           line 60, "(VX-c)" should read --(VI-c).
```

UNITED STATES PATENT AND TRADEMARK OFFICE
CERTIFICATE OF CORRECTION

PATENT NO. : 5,481,009

DATED : JANUARY 2, 1996

INVENTOR(S) : MASAKATSU MATSUMOTO ET AL

It is certified that error appears in the above-identified patent and that said Letters Patent is hereby corrected as shown below:

```
Column 14, line 9,  "(DHE)" should read --(DME)--;
           line 32, "bentoyl" should read --benzoyl--;
           line 47, "end" should read --and--.
Column 15, line 60, "Gartermann reaction, Gettermann-Koch"
                    should read --Gatterman reaction,
                    Gatterman-Koch--;
           line 61, "Vilemeier" should read --Vilsmeir--.
Column 16, line 14, "R³" should read --R⁵--.
Column 19, line 65, "(TMF)" should read --(THF)--.
Column 20, line 57, "400 ml a" should read --400 ml of a--.
Column 24, line 9,  "exact" should read --extract--;
           line 67, "faltered" should read --filtered--.
Column 25, line 55, "pHI" should read --pH2--.
Column 27, line 35, "2 hour" should read --2 hours--;
           line 50, "hexene" should read --hexane--;
Column 31, line 55, "Melting 77.0°" should read --Melting
                    point 77.0°--.
Column 33, line 33, "hexene" should read --hexane--.
Column 35, line 19, "TMF" should read --THF--.
```

UNITED STATES PATENT AND TRADEMARK OFFICE
CERTIFICATE OF CORRECTION

PATENT NO. : 5,481,009
DATED : JANUARY 2, 1996
INVENTOR(S) : MASAKATSU MATSUMOTO ET AL

It is certified that error appears in the above-identified patent and that said Letters Patent is hereby corrected as shown below:

```
Column 36, line 60, "Was" should read --was--.
Column 41, line 30, "hetenoate" should read --heptanoate--.
Column 42, line 31, "hetenoate" should read --heptanoate--.
Column 45, line 16, "19.6" should read --19.6g--.
Column 45, line 55, "(33)" should read --(33))--.
Column 48, line 39, "(79.16)" should read --(79.1%)--.
Column 55, line 58, "Melting points:" should read
                    --Melting point:--.
Column 56, line 37, "was stirred was then" should read
                    --was then stirred--.
Column 57, line 28, "dilsobutylaluminum" should read
                    --diisobutylaluminum--.
Column 61, line 29, "2,2'-" should read --2.2- --.
Column 63, line 25, "(4-fluorophenyl)" should read
                    --(4'-fluorophenyl)--.
```

UNITED STATES PATENT AND TRADEMARK OFFICE
CERTIFICATE OF CORRECTION

PATENT NO. : 5,481,009

DATED : JANUARY 2, 1996

INVENTOR(S) : MASAKATSU MATSUMOTO ET AL

It is certified that error appears in the above-identified patent and that said Letters Patent is hereby corrected as shown below:

```
Column 63, line 66,   "bezo[b]furan" should read
                      --benzo[b]furan--.
Column 64, line 42,   "benzo[b]furan" should read
                      --benzo[b]furan--.
Column 66, line 55,   "yield of mg" should read --yield
                      of 753 mg--.
Column 73, line 16,   "or 2 hours" should read --for 2 hours--;
           line 24,   "o[hexane" should read --of hexane--.
Column 74, line 45,   TABLE 1, under Compound "5.6-dimethoxy"
                      should read --5,6-dimethoxy--.
Column 76, line 5,    "1" should read "2".
```

Signed and Sealed this

Eighteenth Day of February, 1997

BRUCE LEHMAN

Attest:

*Attesting Officer*

*Commissioner of Patents and Trademarks*